United States Patent
Kowalewski

(10) Patent No.: US 11,135,580 B1
(45) Date of Patent: Oct. 5, 2021

(54) DEVICE, KIT AND METHODS FOR CREATING PLATELET RICH PLASMA

(71) Applicant: PRP TECHNOLOGIES INC., Calgary (CA)

(72) Inventor: Ryszard Kowalewski, Calgary (CA)

(73) Assignee: PRP TECHNOLOGIES INC, Calgary (CA)

( * ) Notice: Subject to any disclaimer, the term of this patent is extended or adjusted under 35 U.S.C. 154(b) by 0 days.

(21) Appl. No.: 17/144,442

(22) Filed: Jan. 8, 2021

Related U.S. Application Data

(63) Continuation of application No. 17/258,864, filed as application No. PCT/US2020/042129 on Jul. 15, 2020.

(51) Int. Cl.
| | |
|---|---|
| *B01L 3/00* | (2006.01) |
| *B01D 21/26* | (2006.01) |
| *A61M 1/02* | (2006.01) |
| *A61M 1/34* | (2006.01) |
| *A61K 35/16* | (2015.01) |

(52) U.S. Cl.
CPC .......... *B01L 3/50215* (2013.01); *A61K 35/16* (2013.01); *A61M 1/029* (2013.01); *A61M 1/3482* (2014.02); *A61M 1/3496* (2013.01); *B01D 21/26* (2013.01); *B01L 3/5021* (2013.01)

(58) Field of Classification Search
CPC .. A61M 1/3496; A61M 1/3482; A61M 1/029; A61K 35/16; B01D 21/26; B01L 3/5021; B01L 3/50215
See application file for complete search history.

(56) References Cited

U.S. PATENT DOCUMENTS

| | | | |
|---|---|---|---|
| 3,661,265 A | 5/1972 | Greenspan | |
| 6,516,953 B1 * | 2/2003 | DiCesare | B01D 21/0003 210/516 |
| 9,375,661 B2 * | 6/2016 | Chapman | B01L 3/50215 |
| 10,512,659 B2 | 12/2019 | Tucker | |
| 2010/0025342 A1 | 2/2010 | Morimoto | |
| 2012/0226239 A1 | 9/2012 | Green | |
| 2018/0318830 A1 | 11/2018 | Kim | |
| 2021/0046402 A1 * | 2/2021 | Weinstock | B29C 45/0017 |

FOREIGN PATENT DOCUMENTS

| | | |
|---|---|---|
| WO | WO2005/087292 | 9/2005 |
| WO | WO 2005/087292 A1 * | 11/2005 |

* cited by examiner

*Primary Examiner* — John Kim
(74) *Attorney, Agent, or Firm* — Jonathan D. Feuchtwang

(57) ABSTRACT

A device for extracting plasma from a fluid collection tube comprising: a tubular barrel having sidewall surrounding a lumen which extends between proximal and distal ends thereof, the tubular barrel forming a tip at a distal end; a barrel seal movingly seated within the lumen of the tubular barrel, the barrel seal closing and sealing the proximal end of the tubular barrel; a tube seal having a proximal end, a distal end, and a lumen extending therebetween, the proximal end having a frustoconical or chamfered face, the tube seal having an outer diameter sized to sealingly engage with an inner surface of the fluid collection tube, and an inner diameter sized to sealingly engage with an outer surface of the tip of the tubular barrel, the tube seal mounted on the tubular barrel such that the tip of the tubular barrel extends into the tube seal lumen.

10 Claims, 62 Drawing Sheets

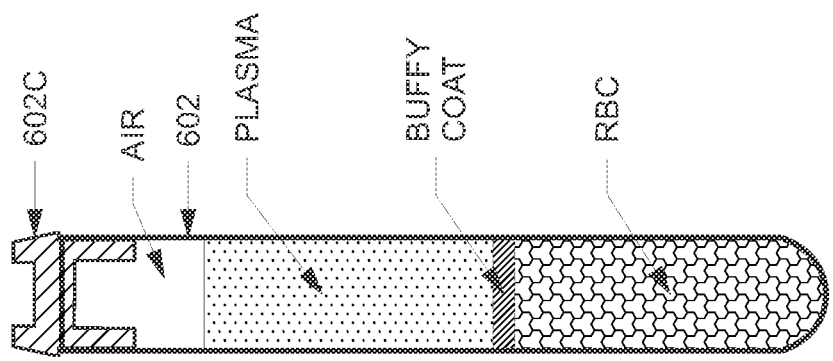
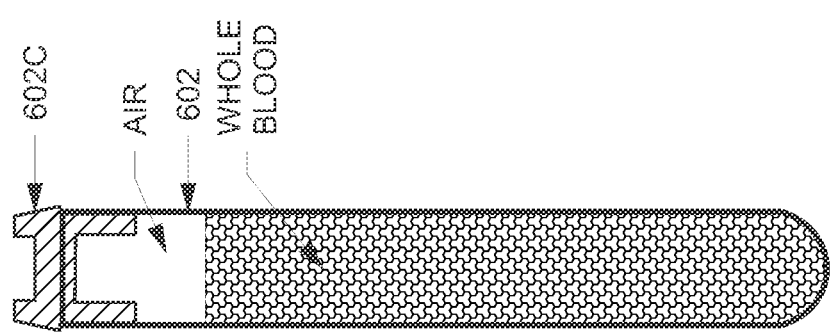
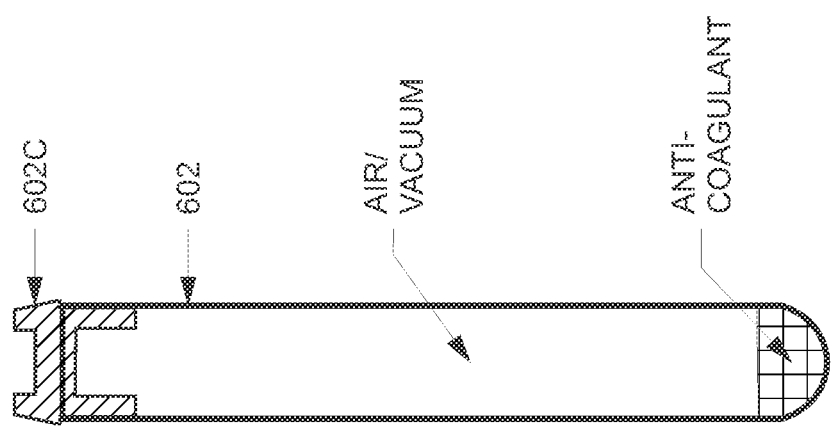

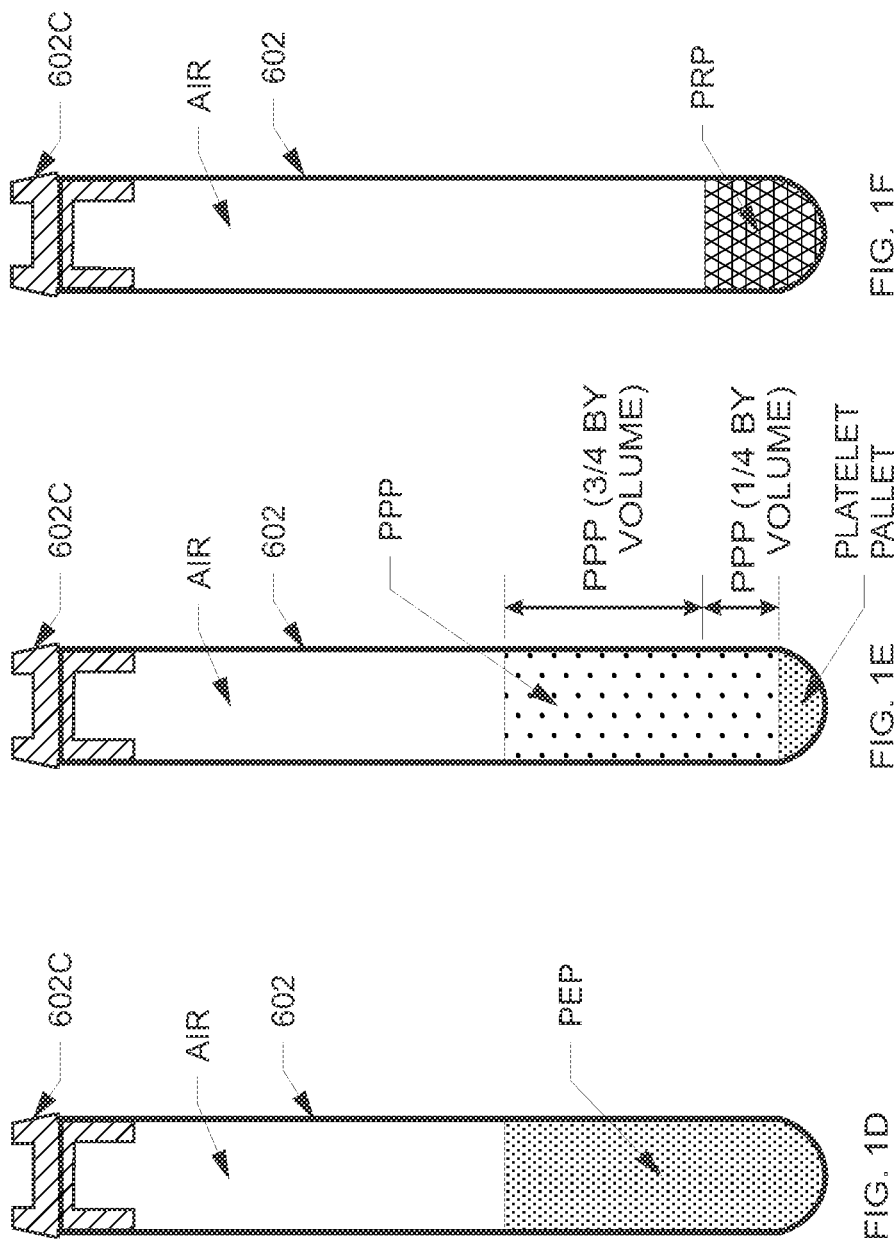

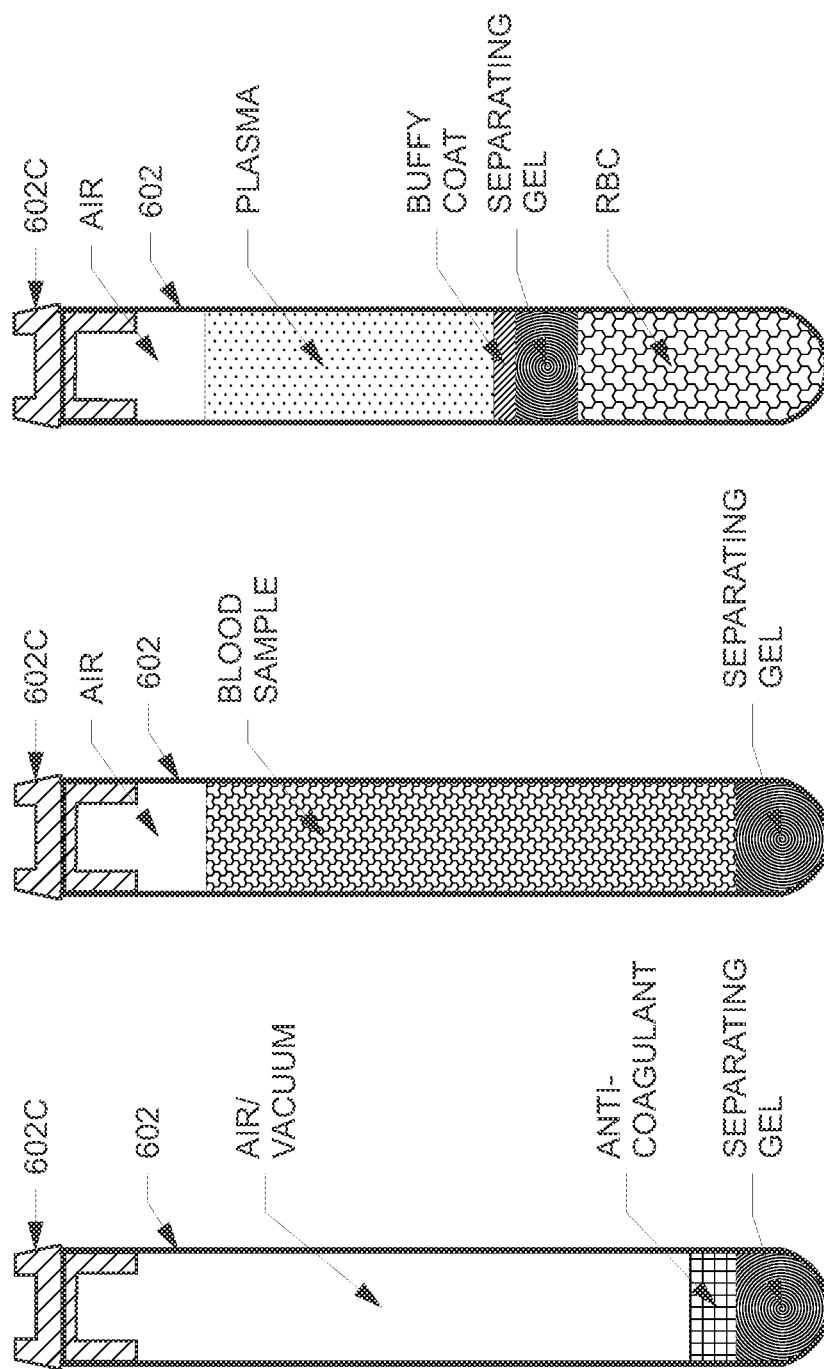

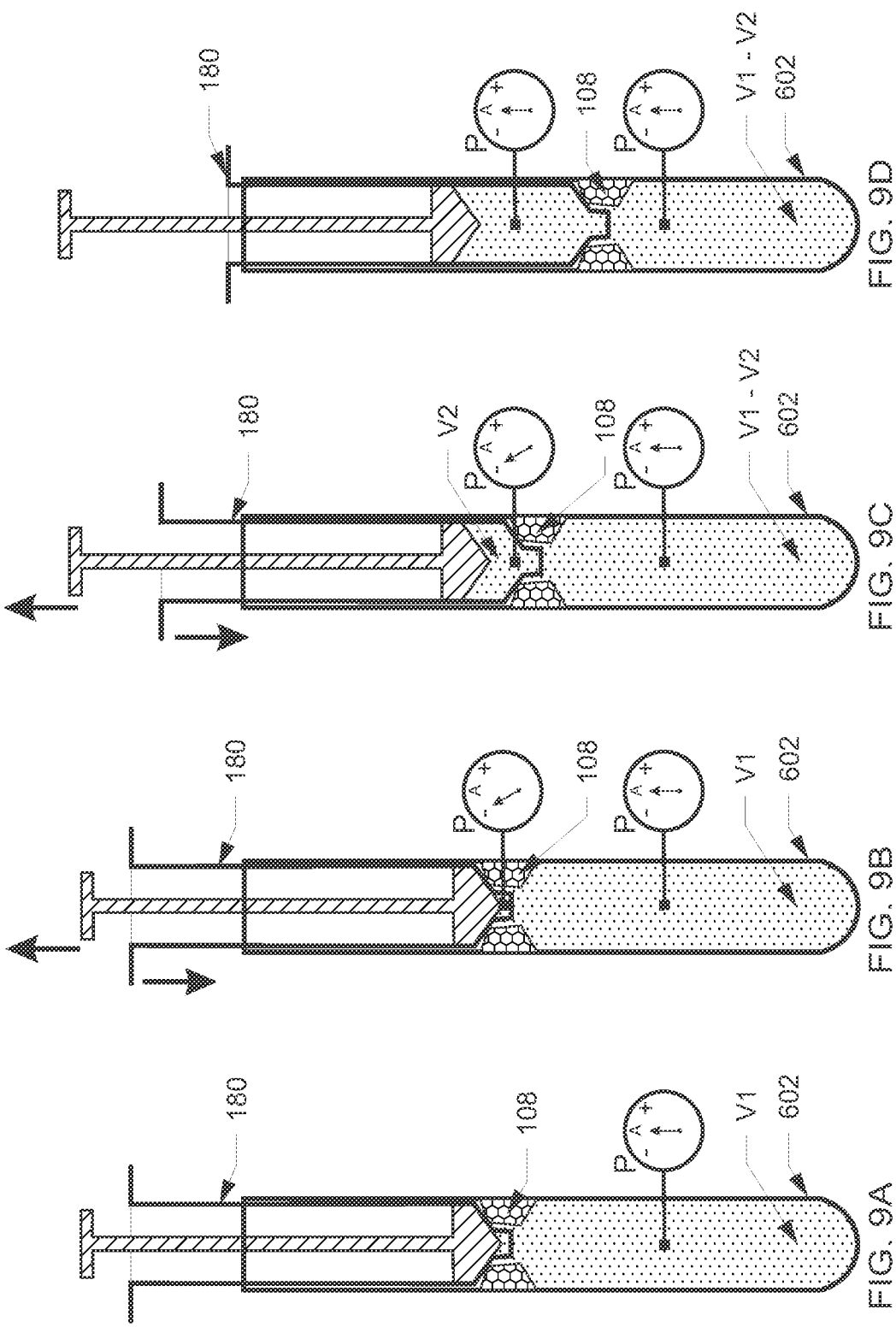

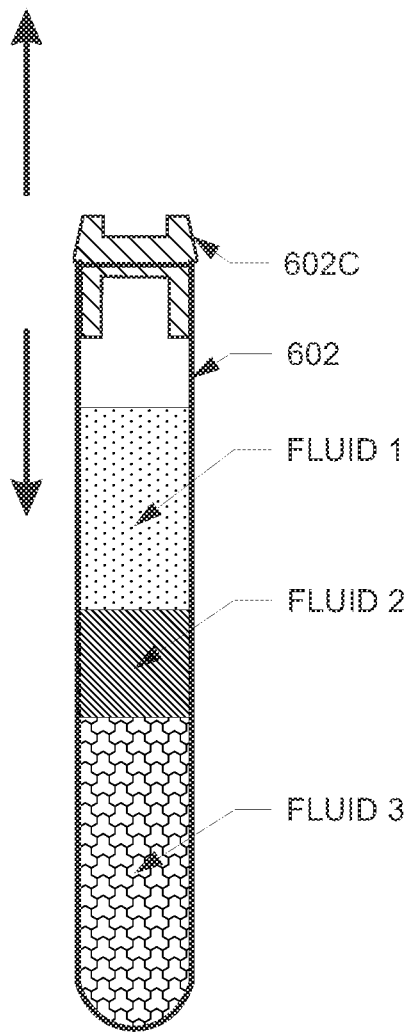
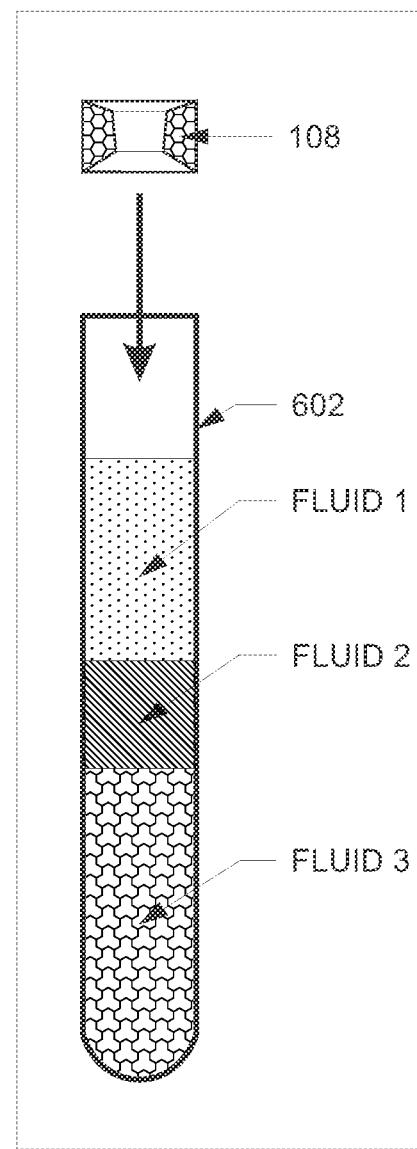
FIG. 10A                    FIG. 10B

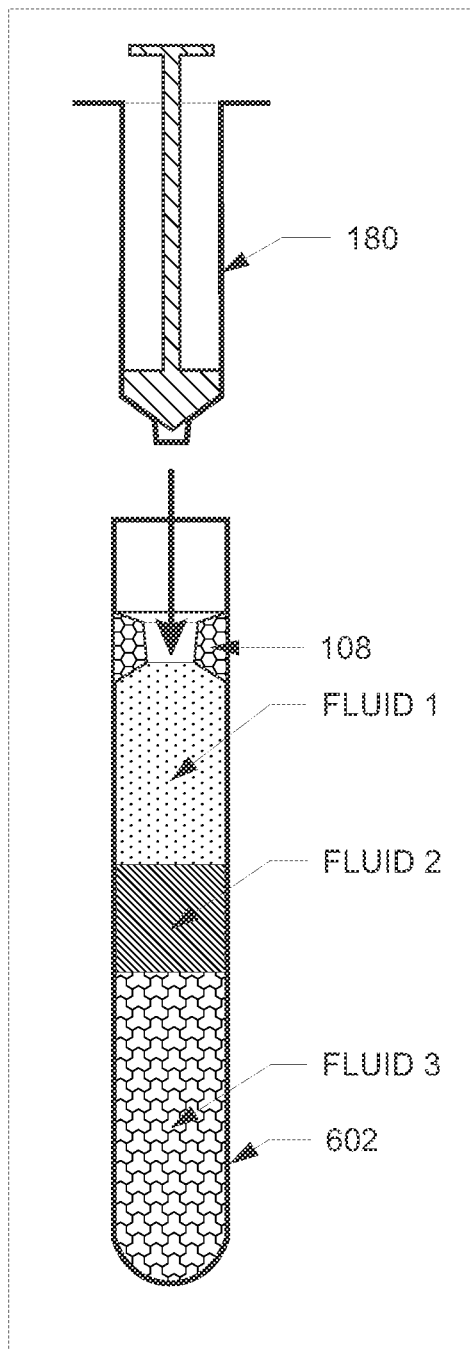
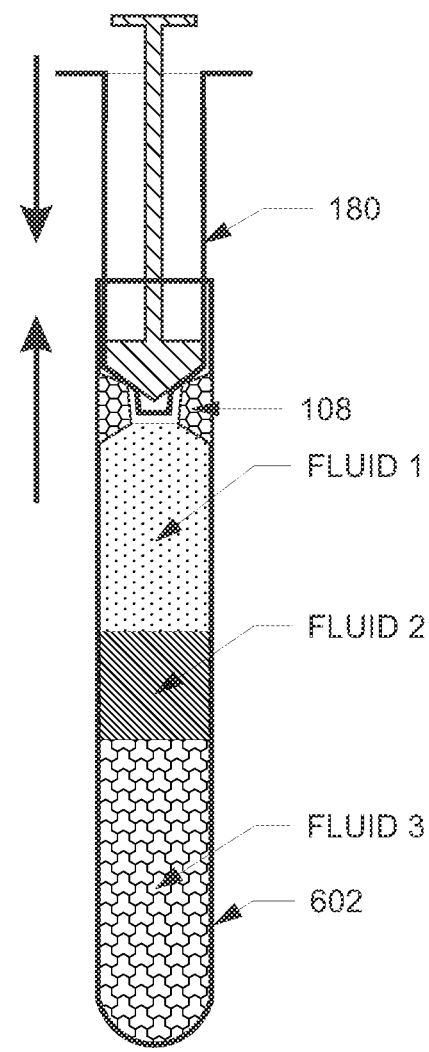
FIG. 10C
FIG. 10D

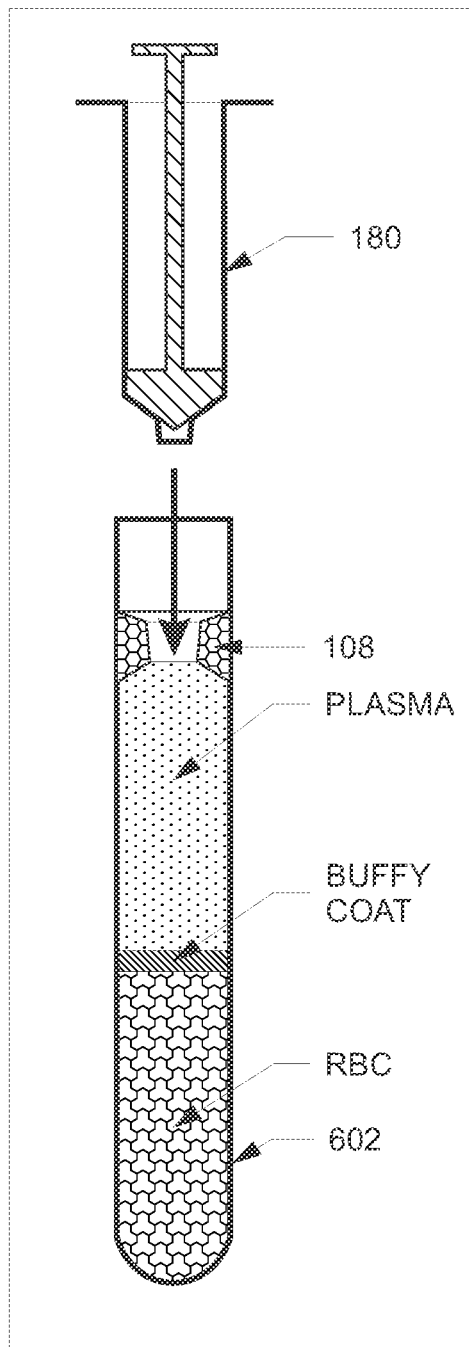
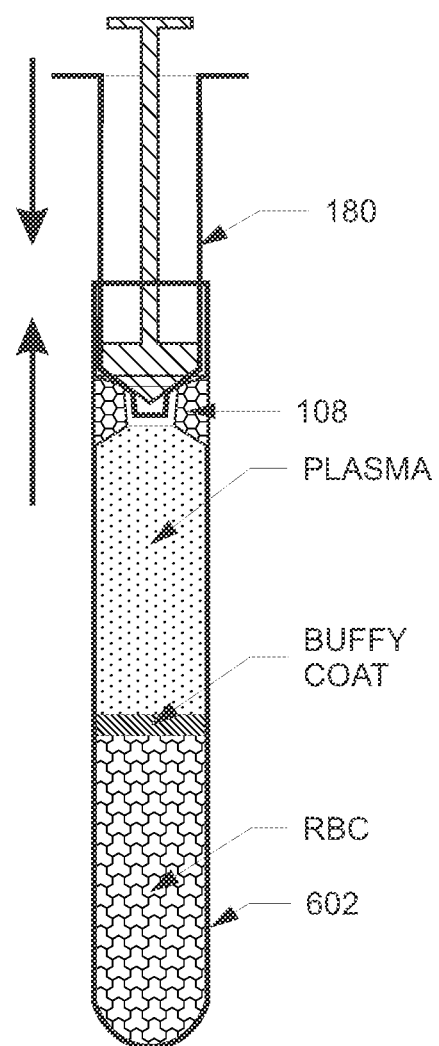
FIG. 11C
FIG. 11D

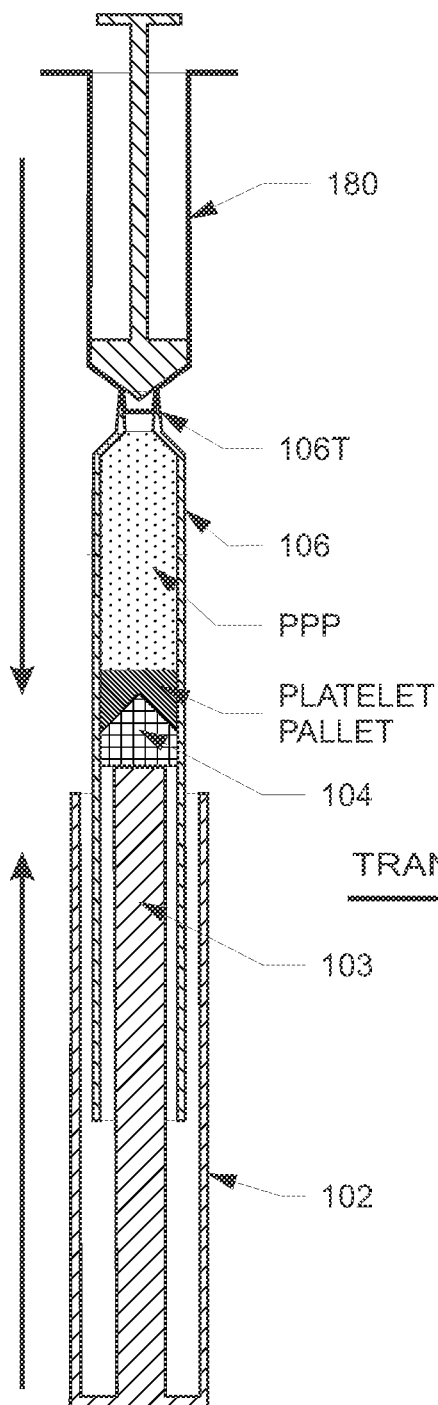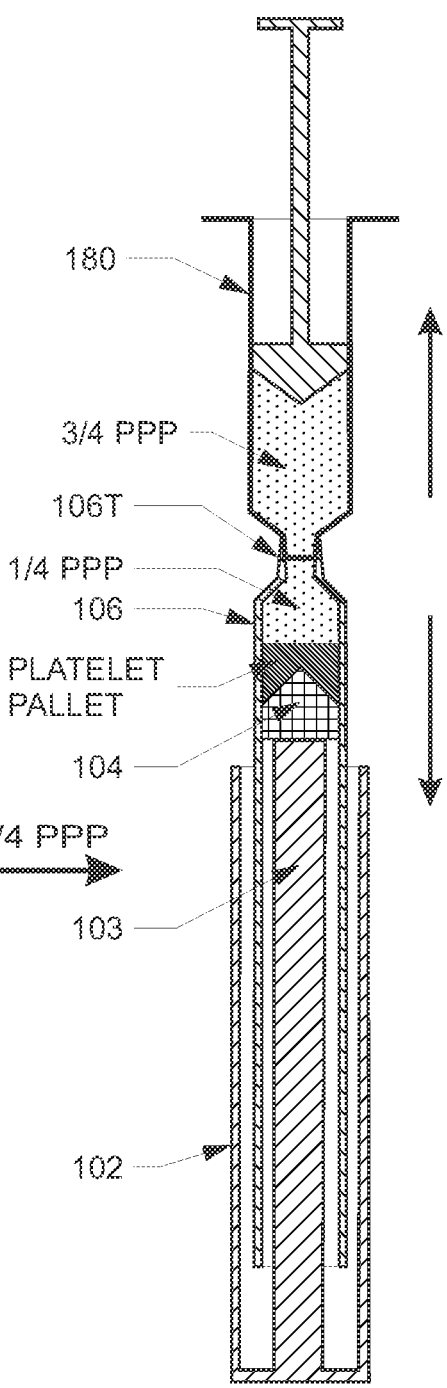
FIG. 18K-1        FIG. 18K-2

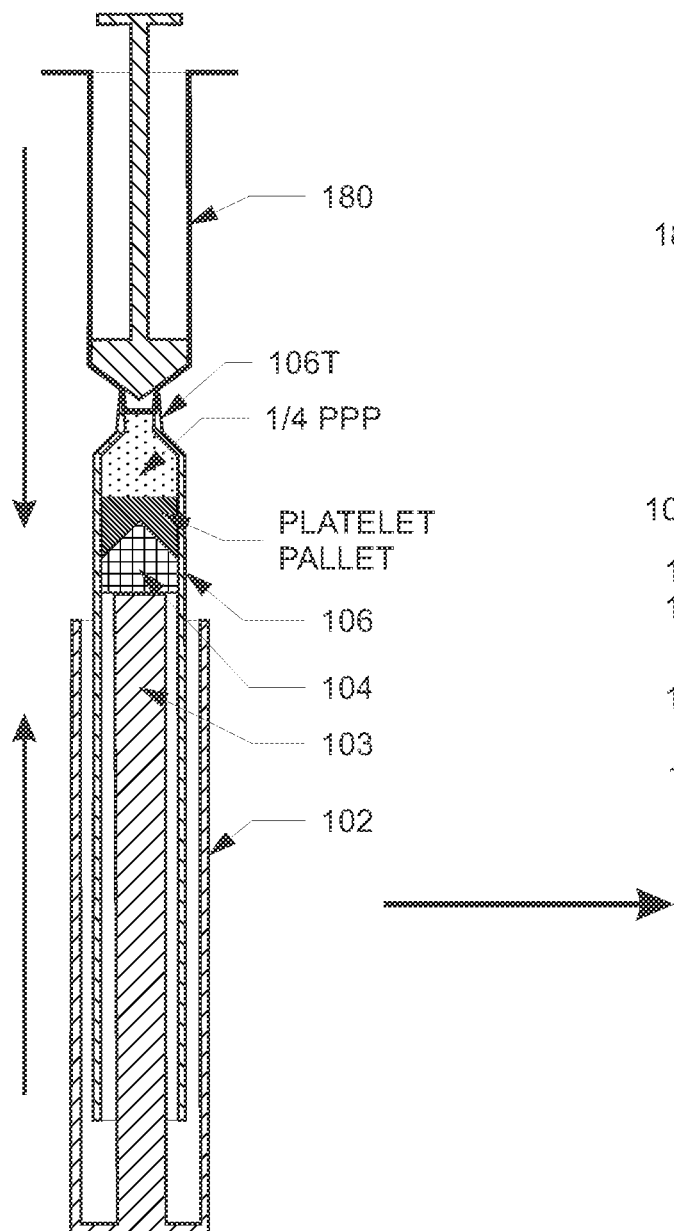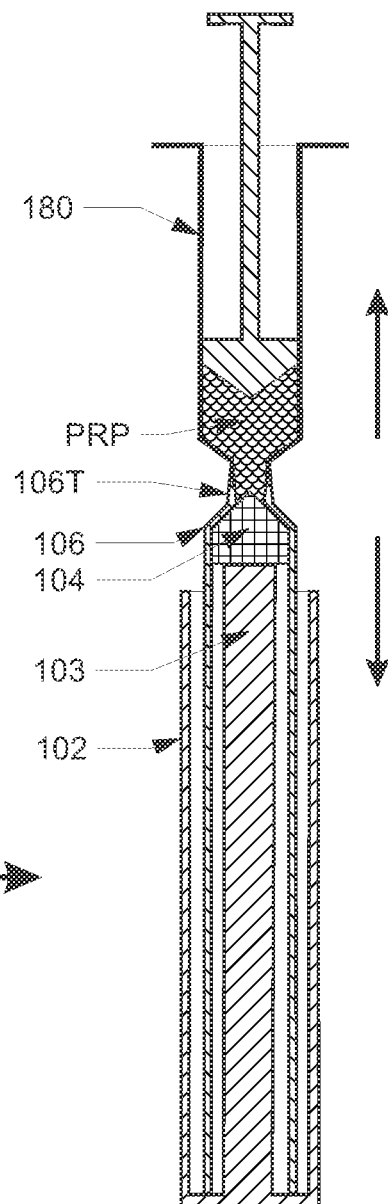
FIG. 18L-1                    FIG. 18L-2

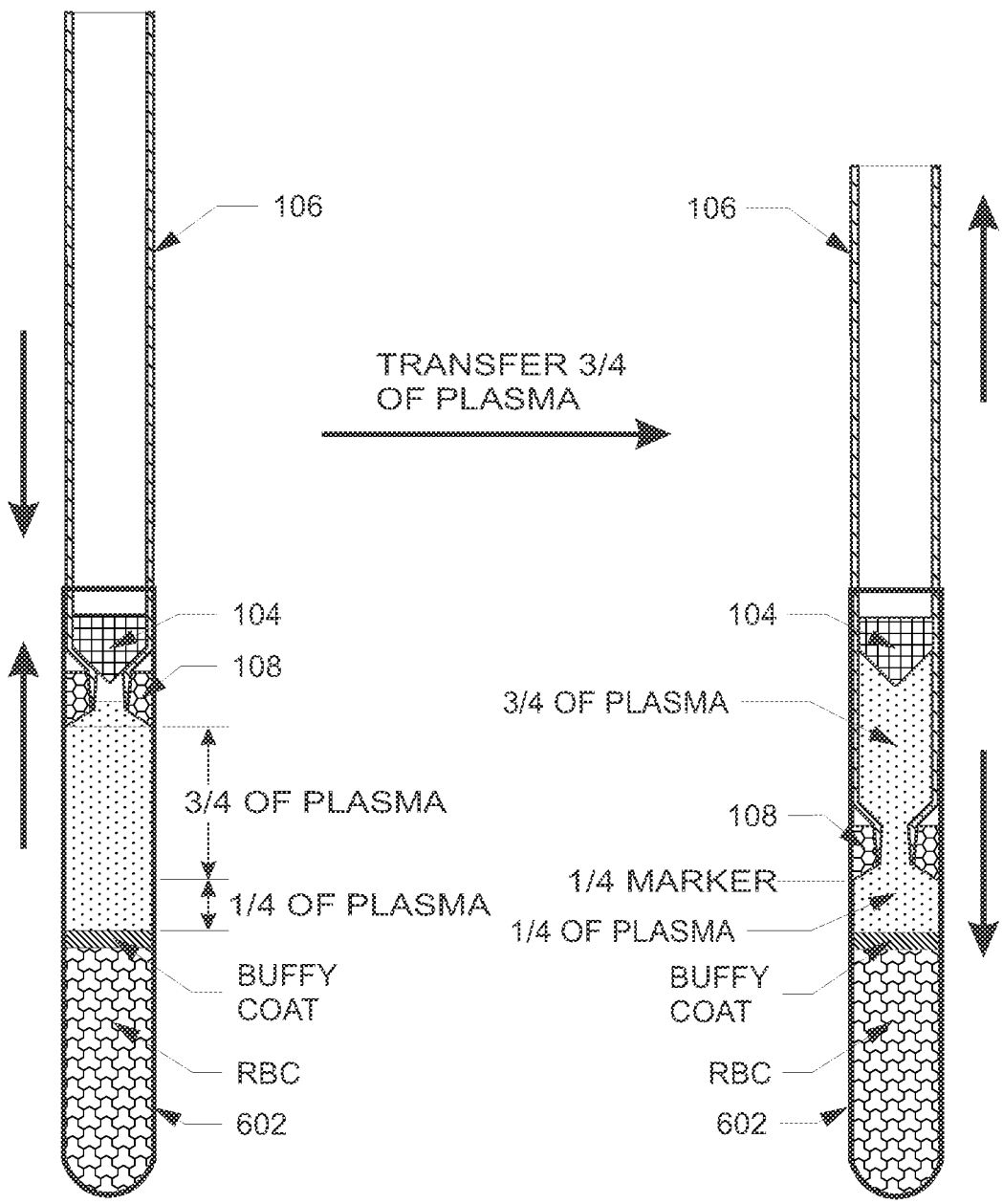

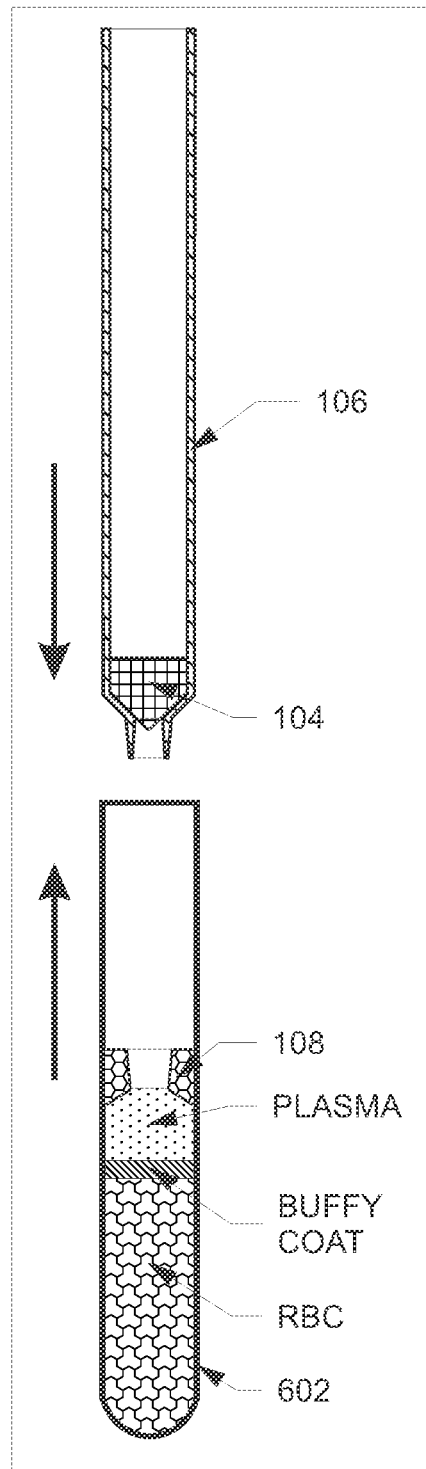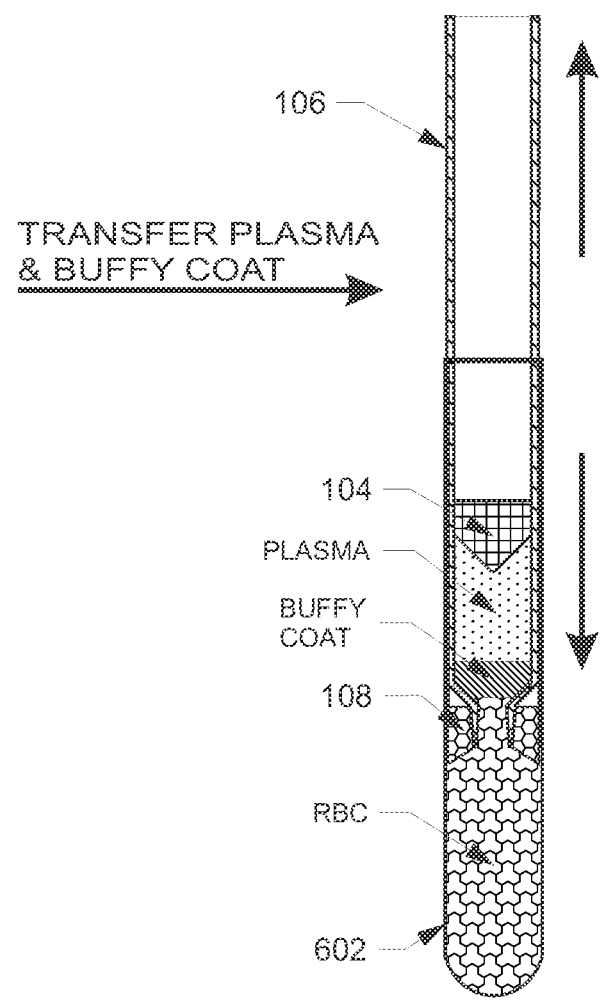
FIG. 19G-1
FIG. 19G-2

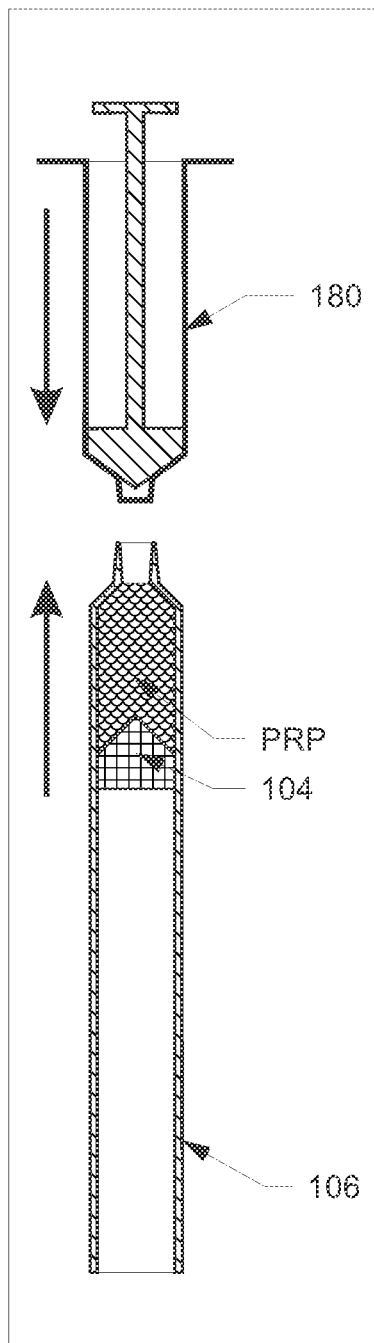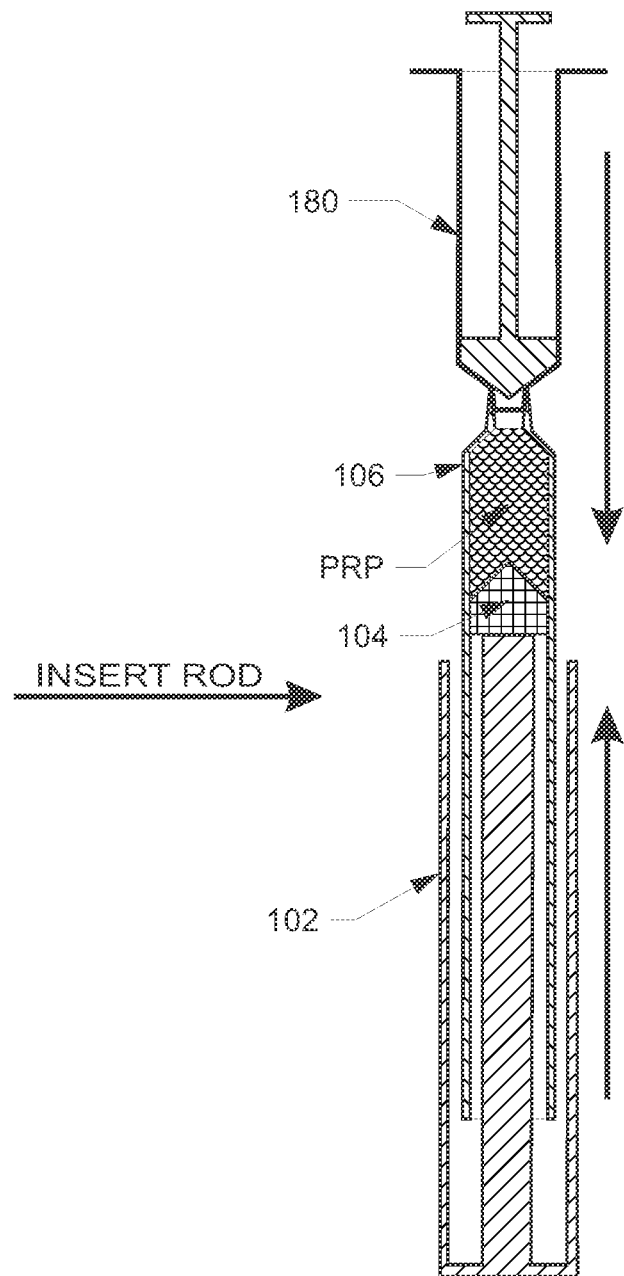
FIG. 19H-1
FIG. 19H-2

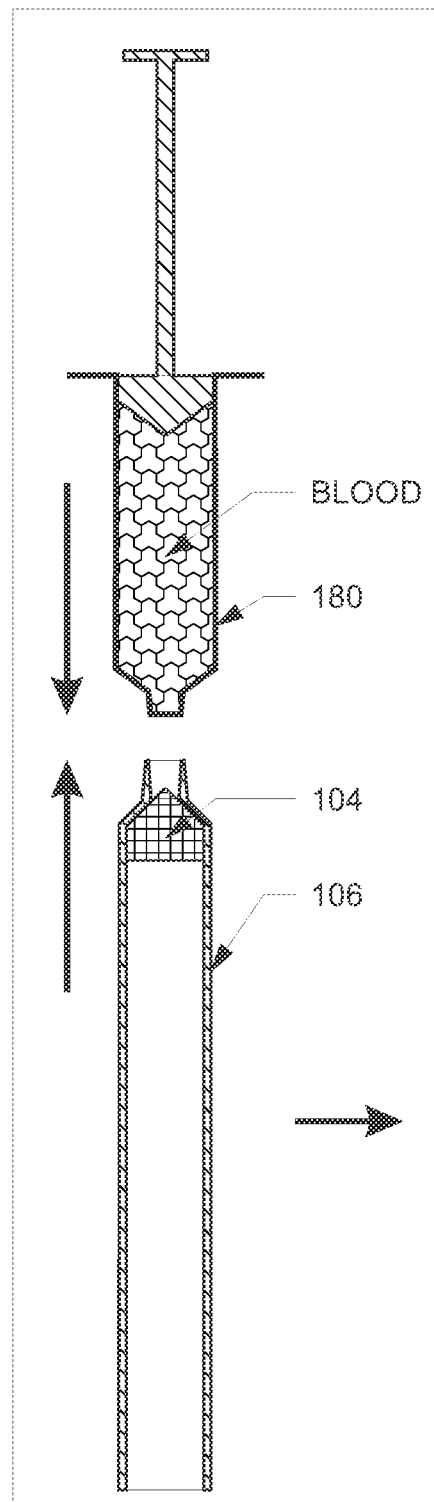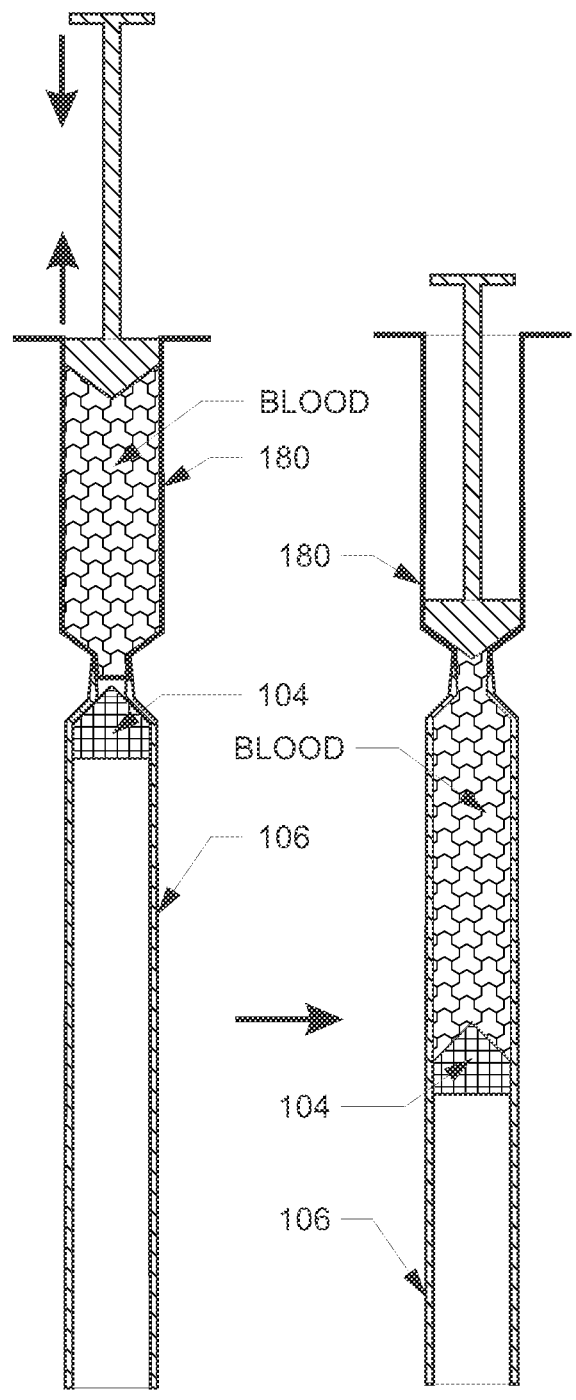
FIG. 20B-1  FIG. 20B-2  FIG. 20B-3

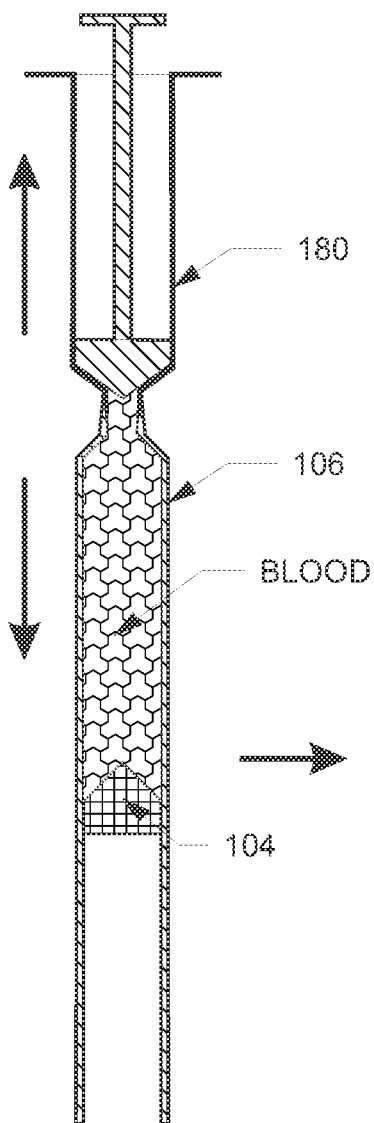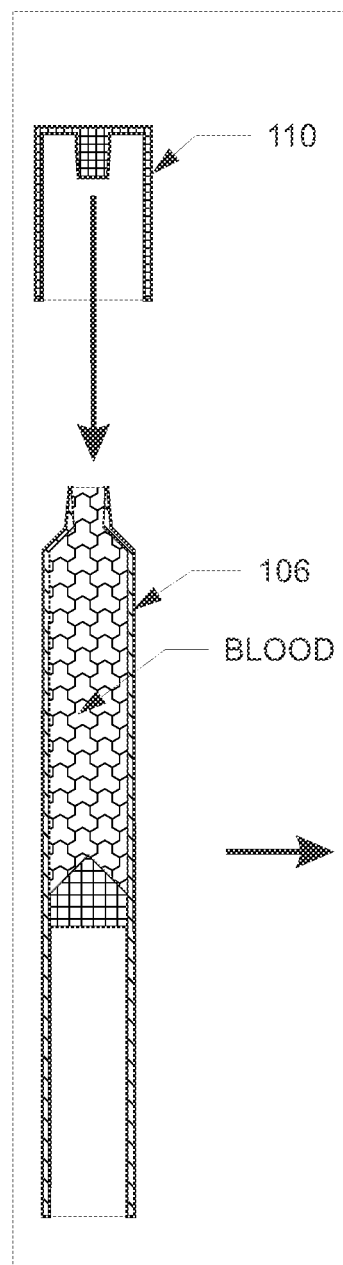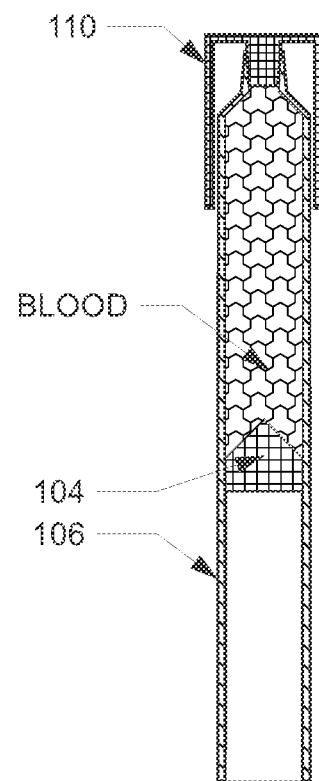
FIG. 20C-1    FIG. 20C-2    FIG. 20C-3

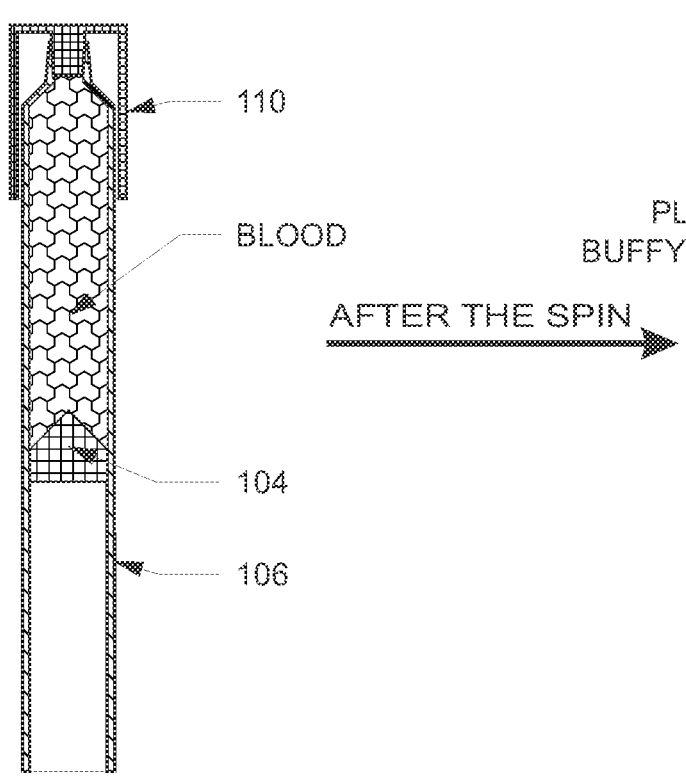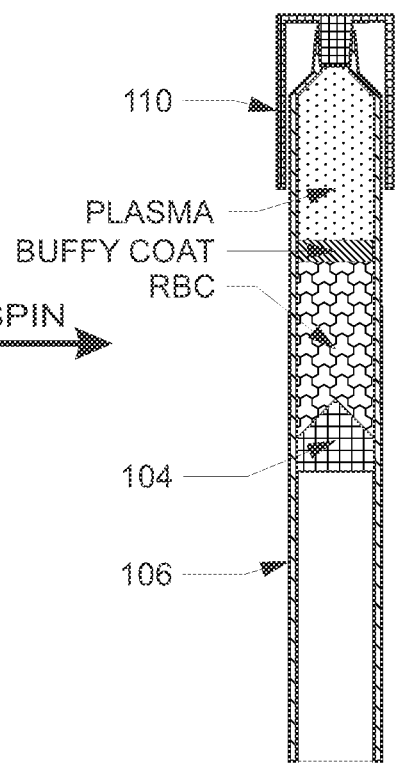
FIG. 20D-1  FIG. 20D-2

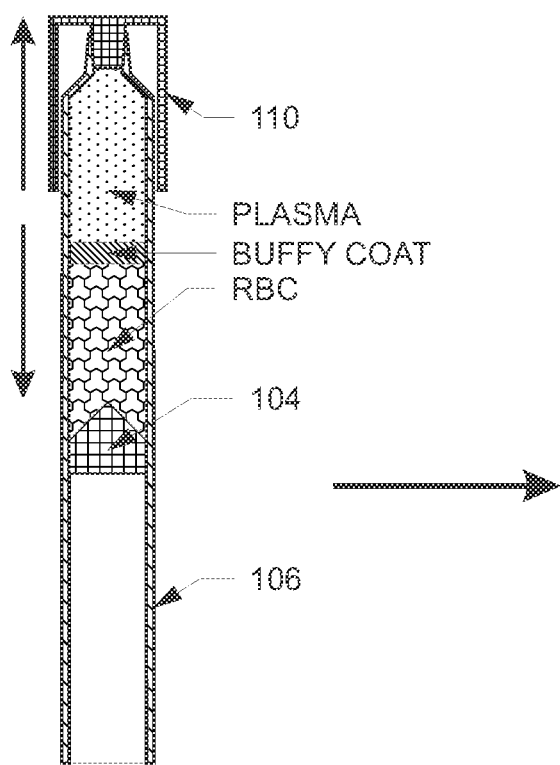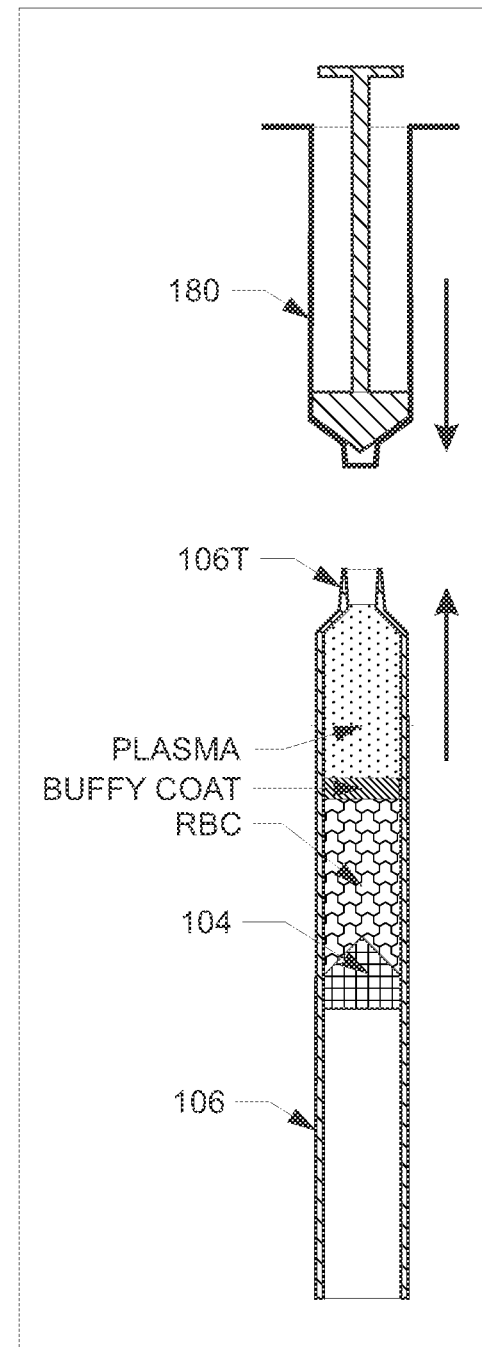
Figure 20E-1     Figure 20E-2

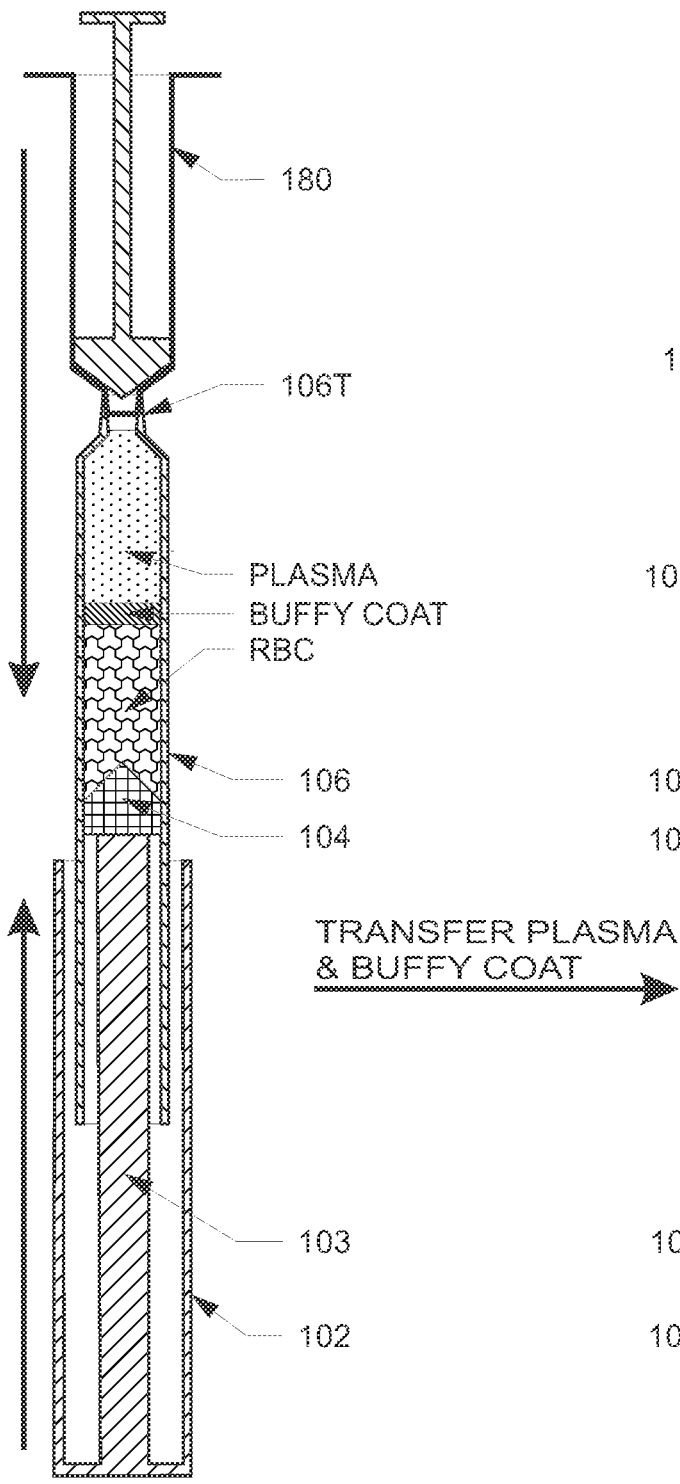
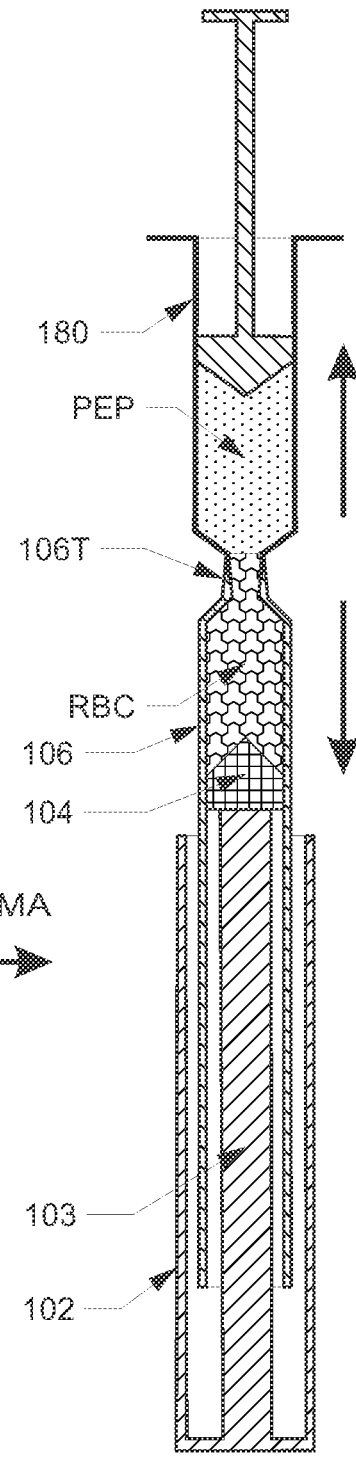
FIG. 20F-1
FIG. 20F-2
TRANSFER PLASMA & BUFFY COAT

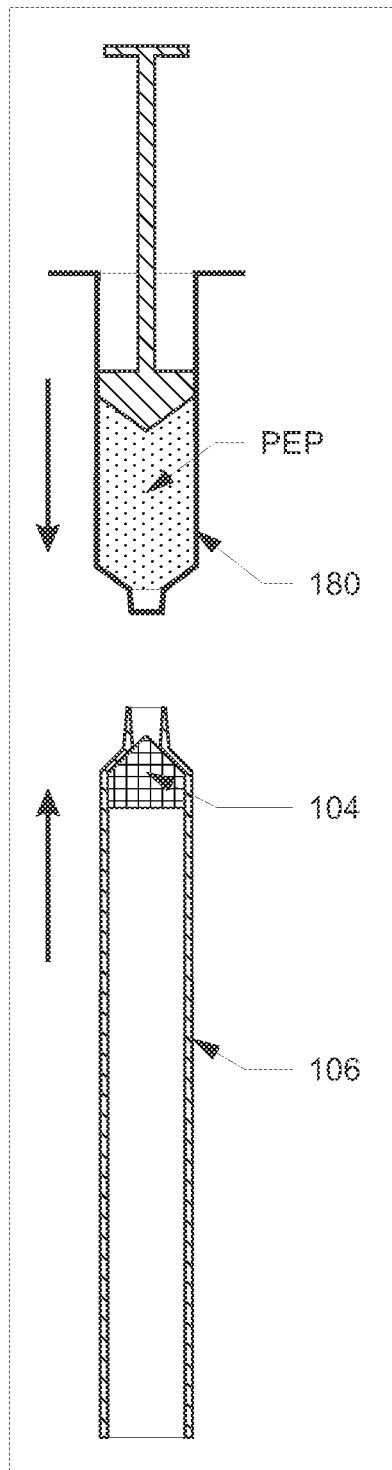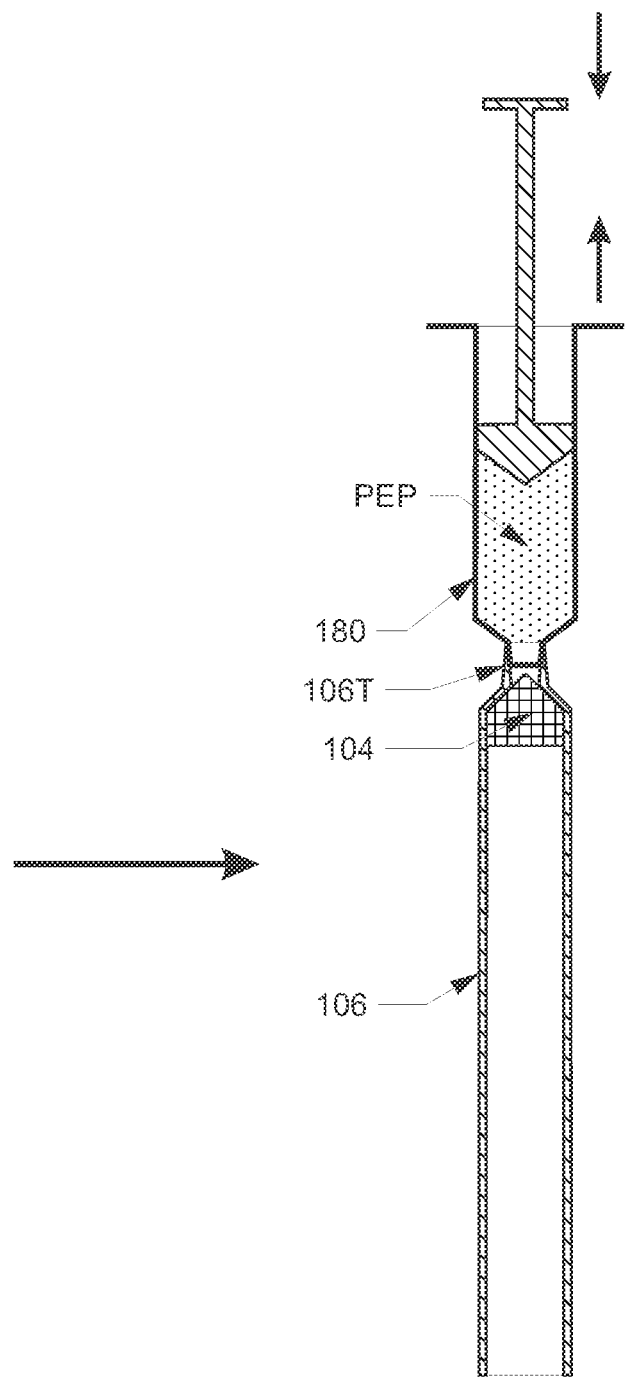
FIG. 20G-1　　　　　　　　FIG. 20G-2

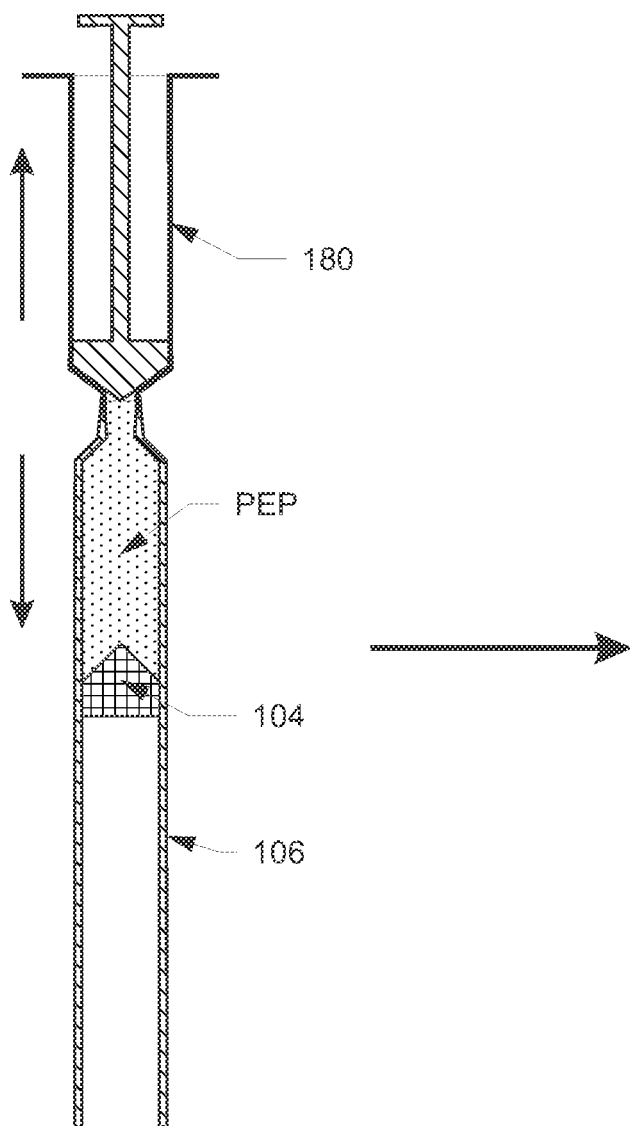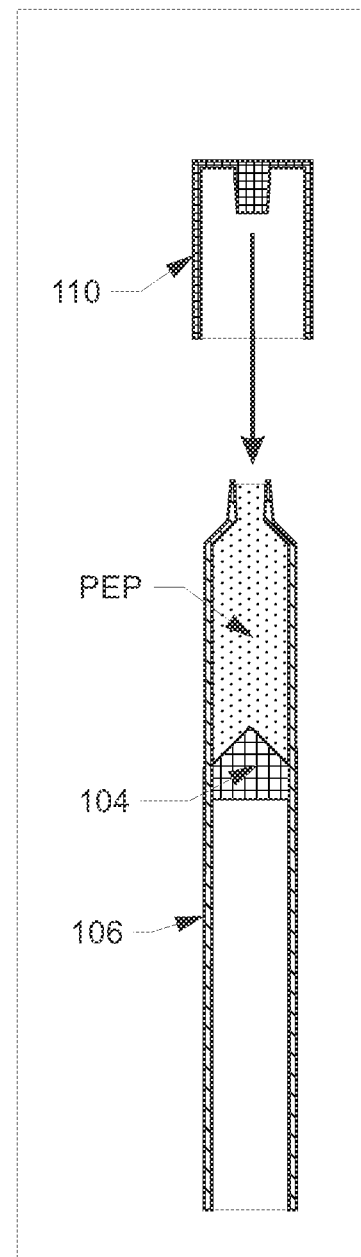
FIG. 20H-1          FIG. 20H-2

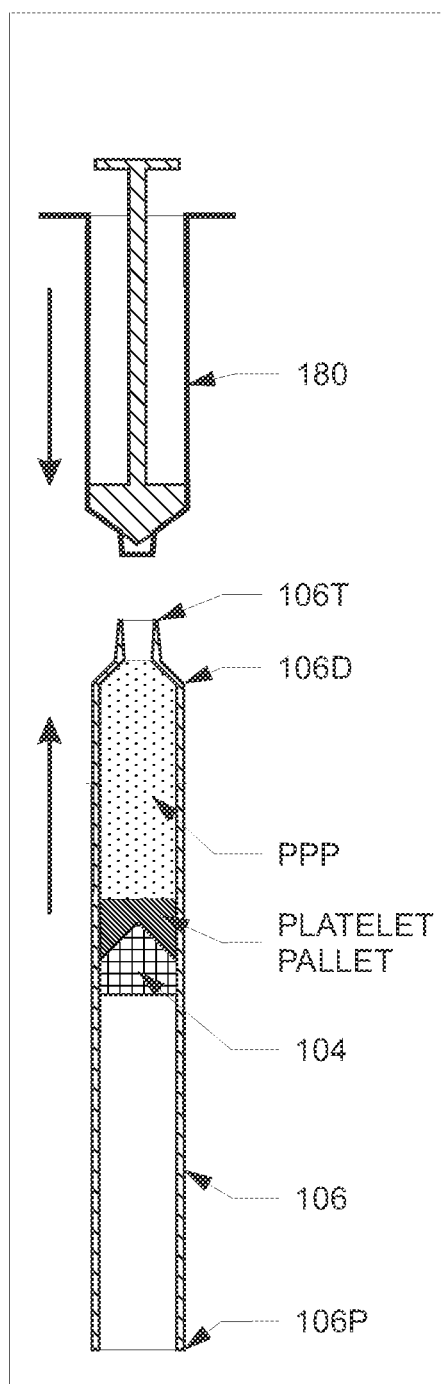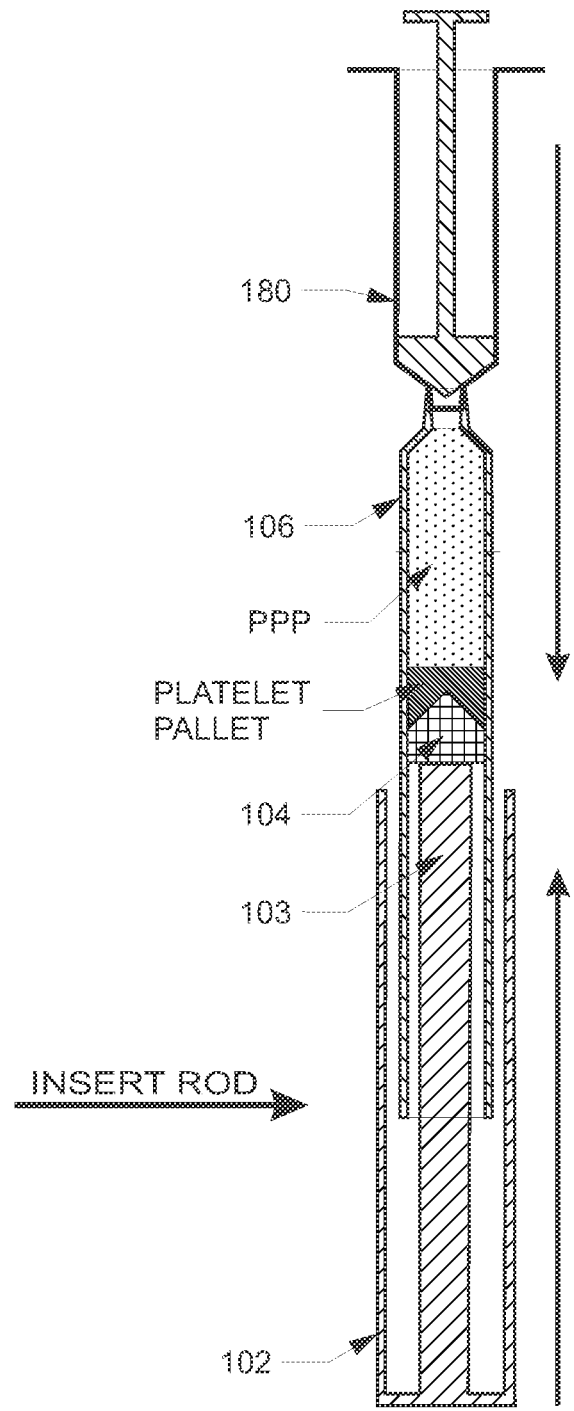
FIG. 20J-1
FIG. 20J-2

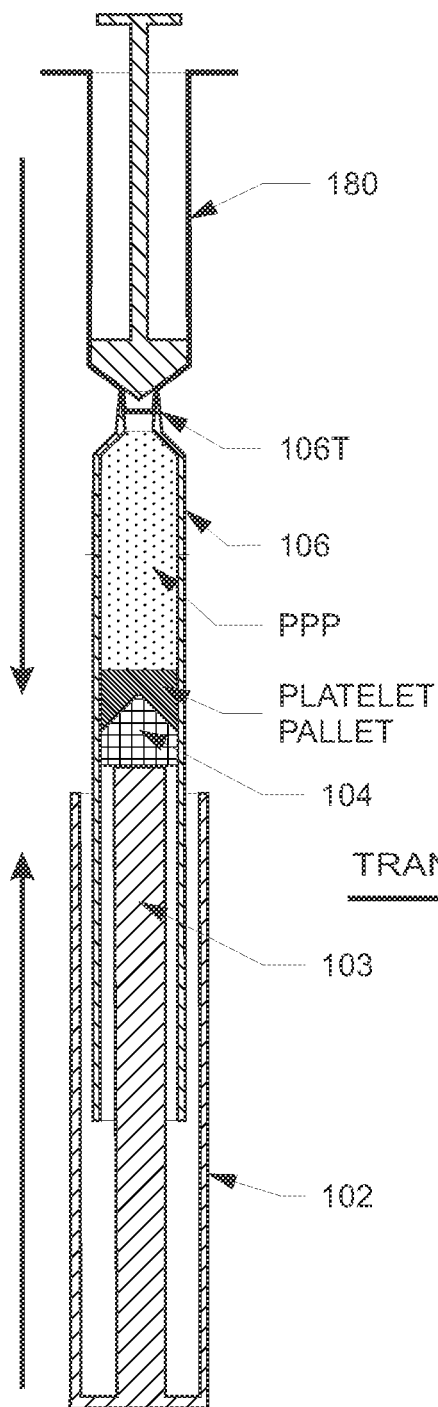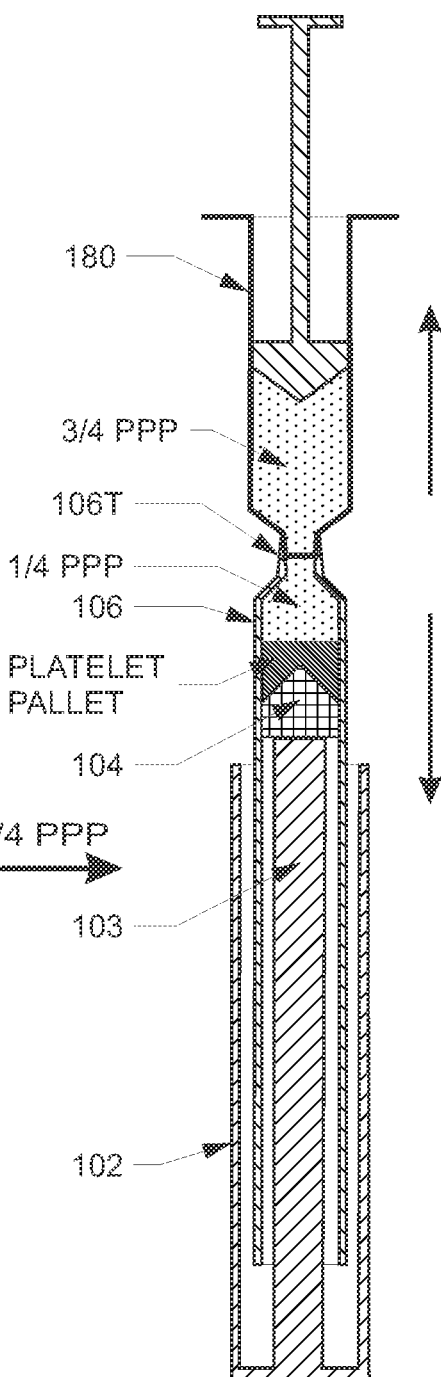
FIG. 20K-1    FIG. 20K-2

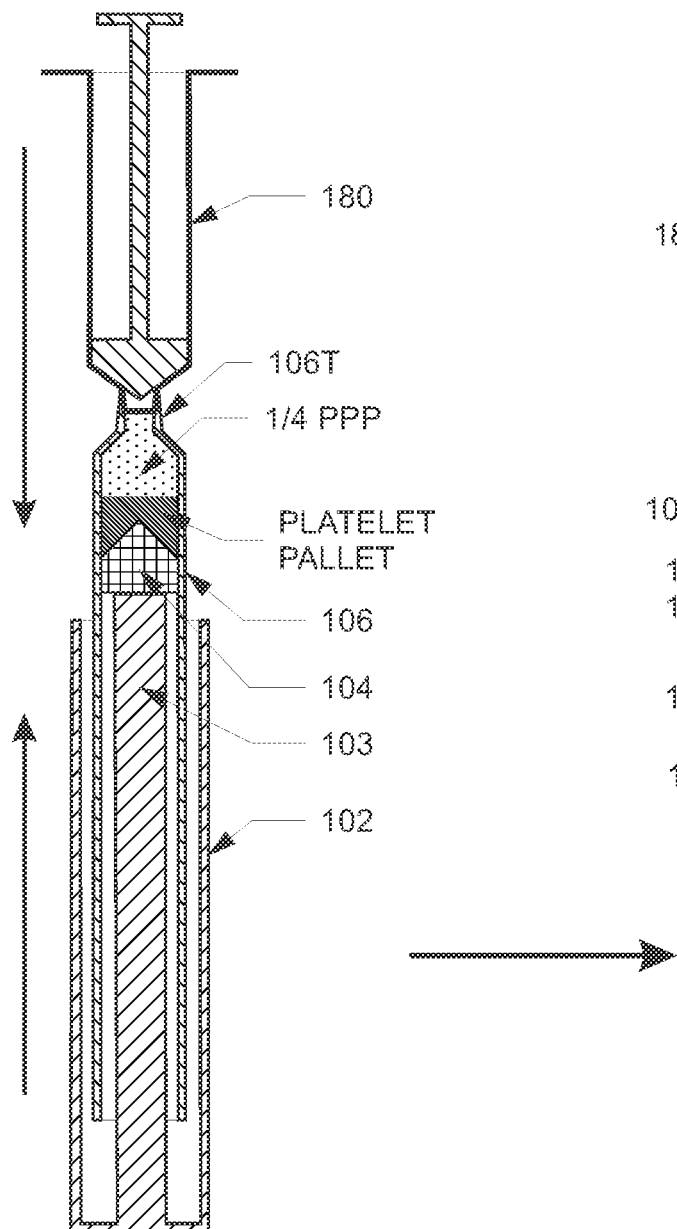
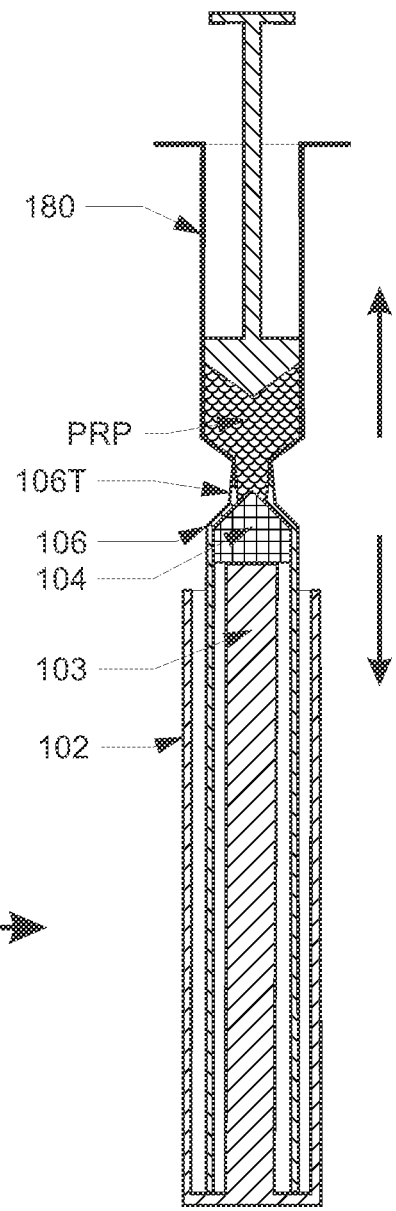
FIG. 20L-1
FIG. 20L-2

DEVICE, KIT AND METHODS FOR CREATING PLATELET RICH PLASMA

FIELD

The invention relates to a method of needless fluid transfer from specimen collection tubes into syringes. The invention and the method have applications in biological, pharmaceutical, and medical fields where extraction of fluids and separation of fluid fractions take place. A preparation of platelet rich plasma (PRP) and separation of platelet poor plasma (PPP) from whole blood are just some of many uses for the device that employ the method of transfer described herein.

BACKGROUND

Platelet Rich Plasma (PRP) is increasingly being used in various medical procedures as a catalyst for regeneration processes. PRP consists of blood plasma with concentrated platelets, which contain various growth factors and other cytokines that are known to stimulate regenerative processes of body tissues like bone, ligaments, skin, hair and much more. It is obtained from the patient's own blood after red blood cells (RBC) have been removed and the platelets are concentrated in a small volume of plasma to 4-8 times (or more) its normal count in blood.

Platelet Poor Plasma (PPP) is used in many laboratory tests (including detecting antibodies in patient blood) and is obtained by removing from whole blood all cellular elements (red blood cells, platelets, white blood cells etc.).

The central part in the process of PRP preparation is prompt separation of blood fractions. Undisturbed blood left alone will separate on its own, due to gravity forces into density layers, but usually a centrifuge is used to accelerate the process.

Generic Process

Traditionally PRP is obtained in several steps using a two-spin method. In the first step the patient's whole blood is drawn to a fluid collection tube. See, FIGS. 1A and 1B. Next, the tube undergoes a first spin cycle (hereinafter "first spin") in the centrifuge and the whole blood is separated into three broad fractions: red blood cells (RBC), buffy coat (leukocytes and platelets) and plasma. See, FIG. 1C.

In the next step, the buffy coat and plasma, collectively Platelet Enriched Plasma (PEP), which contains slightly concentrated platelets (up to two times normal blood count) are transferred to a second tube (FIG. 1D) for a second spin to further concentrate the platelets. After the second spin cycle (hereinafter "second spin") the PEP will separate into Platelet Pallet (PP) and plasma with very few (substantially no) platelets called Platelet Poor Plasma (PPP). See, FIG. 1E.

In the final step, about two-thirds to three-quarters (⅔-¾) of PPP is removed. It contains essentially no cellular elements and can be used in various laboratory tests. The remaining plasma is mixed with Platelet Pallet. The resulting mixture is called PRP with platelet concentration of 4-8 (or more) times normal blood count. See, FIG. 1F.

Prior Art Shortcomings

After the first spin in the above-described process, a syringe is used to aspirate the plasma and buffy coat through a needle, in order to transfer both into a second tube for a second spin. However, in order to reach the buffy coat located just above the RBC, a small diameter syringe and/or a long needle, are required. Most importantly, it is very difficult to aspirate all buffy coat (layered on top of RBC), without also aspirating a significant quantity of the undesired RBC.

Most commonly, commercial PRP tubes containing separating gel, are used to collect blood. See, FIGS. 2A and 2B. While this PRP preparation process is somewhat easier, it also is more costly. The separating gel acts as a semipermeable membrane. During centrifugation, RBC is forced to pass through the gel and collects beneath it, which leaves plasma and buffy coat physically separated above it. After centrifugation, the gel functions as a barrier, allowing the tube to be tilted or turned up-side down (to facilitate aspiration of the buffy coat and plasma), without causing the RBC to mix with the buffy coat and plasma. The mixture of buffy coat and plasma is called Platelets Enriched Plasma (PEP). In the next step, a syringe is used to aspirate the PEP through a needle, in order to transfer it into a second tube to undergo a second spin. See, FIGS. 2C and 2D.

Regardless of whether tubes with separating gel are used, after the first spin plasma and buffy coat (PEP) need to be transferred to another tube for a second spin, to further concentrate the platelets. Because of the relative complexity of those additional steps involved, the medical practitioners often choose to settle for PEP in their procedures, or in some cases proceed with the suboptimal PRP obtained by removing the excess plasma from the single spin.

Present Invention Benefits

The present invention addresses the shortcomings of the existing methods for transferring fluid density layers from specimen tubes into syringes. With respect to PRP preparation, it is a system which makes it possible to transfer a chosen layer of blood fraction after centrifugation, from a fluid collection tube to a syringe or a syringe-like receptacle, without the need for needles and without relying solely on negative pressure aspiration.

The present invention also eliminates the need for separating gel, because it allows a precise transfer of plasma and buffy coat to a syringe or syringe-like device, with minimal RBC contamination. This is possible because the transfer of the lightest density fluid, which has a tendency to stay on top of heavier density fluids, always takes place first, and the quantity being transferred can be easily controlled.

Eliminating the separating gel also eliminates the possibility of contaminating the plasma with gel particles; it also significantly reduces the cost to the operator as well as to the patient. Elimination of needles diminishes the risk of sample contamination and the risk of accidental needle poke that could lead to the transmission of infectious diseases (bacteria, viruses) to the operator.

In addition to eliminating the needles, the present invention also eliminates the need for a second fluid collection tube and for the transfer syringe (used to transfer the product of the first spin (PEP) from the first tube into the second tube to perform the second spin).

The core parts of the invention are a tube seal that eliminates the need for needles and renders the separating gel unnecessary, and a barrel that replaces both the transfer syringe and the second-spin tube.

SUMMARY OF INVENTION

Example 1: A device for extracting plasma from a fluid collection tube containing a sample of whole blood which has been centrifuged to form a red blood cell layer, a buffy coat layer and a plasma layer, the device comprising:

a tubular barrel having sidewall surrounding a lumen which extends between proximal and distal ends thereof, the tubular barrel forming a tip at a distal end;

a barrel seal movingly seated within the lumen of the tubular barrel, the barrel seal closing and sealing the proximal end of the tubular barrel;

a tube seal having a proximal end, a distal end, and a lumen extending therebetween, the proximal end having a frustoconical or chamfered face, the tube seal having an outer diameter sized to sealingly engage with an inner surface of the fluid collection tube, and an inner diameter sized to sealingly engage with an outer surface of the tip of the tubular barrel, the tube seal mounted on the tubular barrel such that the tip of the tubular barrel extends into the tube seal lumen;

wherein as the tubular barrel is advanced into the fluid collection tube, the tube seal engages with inner walls of the fluid collection tube and the outer surface of the tip of the tubular barrel, and the barrel seal is pushed proximally by plasma flowing from the fluid collection tube into the lumen of the tubular barrel.

Example 2: The tube seal of Example 1, wherein the tube seal is an elastomeric member having at least one sealing ring provided on the exterior surface thereof.

Example 3: The device of Examples 1-2, further comprising an elongate rod having an outer diameter which is smaller than a diameter of the lumen of the tubular barrel, the rod being removably inserted into the lumen of the tubular barrel.

Example 4: The device of Example 3, further comprising:

a tubular casing having a closed proximal end and an open distal end and a lumen extending between the closed proximal end and the open distal end;

a diameter of the rod being less than a diameter of the lumen of the tubular casing;

at least a portion of the rod coaxially received within the tubular casing, with a gap G defined between an inner surface of the tubular casing and an exterior surface of the rod;

a portion of the tubular barrel sidewall being coaxially received in the gap G.

Example 5: The device of Example 1, further comprising a barrel cap configured to sealingly engage with the tip of the tubular barrel and engaging an exterior surface of the tip and/or having a plug which fits into the lumen of the tip.

Example 6: A kit for extracting plasma from a fluid collection tube containing a centrifuged sample of whole blood which has been centrifuged to form a red blood cell layer, a buffy coat layer and a plasma layer, the kit comprising a tube seal having a lumen therethrough, the tube seal sized to movably engage with an inner surface of the fluid collection tube, the lumen of tube seal being sized to sealingly engage with a tip of a syringe-like device.

Example 7: The kit of Example 6, further comprising:

a tubular barrel having sidewall surrounding a lumen which extends between proximal and distal ends thereof, the tubular barrel forming a tip at a distal end; and a barrel seal movingly seated within the lumen of the tubular barrel, the barrel seal closing and sealing the proximal end of the tubular barrel;

wherein the tip of the tubular barrel sized to snugly fit into and sealingly engage with the lumen of the tube seal;

wherein as the tubular barrel is advanced into the fluid collection tube, the tube seal engages with the inner surface of the fluid collection tube and engages with an outer surface of the tip of the tubular barrel, and the barrel seal is pushed proximally by plasma flowing from the fluid collection tube into the lumen of the tubular barrel.

Example 8: The kit of Example 7, comprising an elongate rod having an outer diameter which is smaller than a diameter of the lumen of the tubular barrel, the elongate rod being removably inserted into the lumen of the tubular barrel.

Example 9: The kit of Example 8, further comprising a tubular casing having a closed proximal end and an open distal end and a lumen extending between the closed proximal end and the open distal end.

Example 10: The kit of Example 6-9, wherein the tube seal is removably mounted to the tip of the tubular barrel.

Example 11: The kit of Example 10, further comprising a barrel cap configured to sealingly engage with the tip of the tubular barrel and engaging an exterior surface of the tip and/or having a plug which fits into the lumen of the tip.

Example 12: A tube seal, comprising: an elastomeric member having a longitudinal axis, a proximal end, a distal end, and a lumen extending therebetween, the proximal end having a frustoconical or chamfered face, the elastomeric member having an outer diameter sized to sealingly engage with an inner surface of a fluid collection tube, the lumen of tube seal being sized to sealingly engage with a tip of a syringe-like device.

Example 13: The tube seal of Example 12, further comprising at least one sealing ring provided on the exterior surface of the elastomeric member.

Example 14: A method for creating for extracting plasma from a fluid collection tube containing a sample of whole blood which has been centrifuged to form a red blood cell layer, a buffy coat layer and a plasma layer, comprising the steps of:

providing a tubular barrel having sidewall surrounding a lumen which extends between proximal and distal ends thereof, the tubular barrel forming a tip at a distal end, a barrel seal movingly seated within the lumen of the tubular barrel, the barrel seal closing and sealing the proximal end of the tubular barrel, and a tube seal having a proximal end, a distal end, and a lumen extending therebetween, the proximal end having a frustoconical or chamfered face, the tube seal having an outer diameter sized to sealingly engage with an inner surface of the fluid collection tube, and an inner diameter sized to sealingly engage with an outer surface of the tip of the tubular barrel, the tip of the tubular barrel extending into the tube seal lumen;

inserting the distal end of the tubular barrel into the fluid collection tube such that the tube seal engages with an inner surface of the fluid collection tube;

as the tubular barrel is advanced into the fluid collection tube pushing the tube seal distally, plasma will flow through the tube seal lumen into the lumen of the tubular barrel and the barrel seal is pushed proximally by the plasma flowing into the tubular barrel, wherein the tubular barrel is advanced until red blood cells just start to enter into the tubular barrel, at which point the plasma and the buffy coat have been transferred to the tubular barrel;

the tubular barrel is withdrawn from the fluid collection tube, leaving the tube seal engaged within the fluid collection tube along with the remaining red blood cells; and the tubular barrel containing the plasma and buffy coat is centrifuged to separate the plasma into platelet poor plasma (PPP) and platelet pallet.

Example 15: The method of Example 14, comprising the steps of:

providing a first syringe having a first plunger movably mounted therein;

fluidically coupling a tip of the first syringe to the tip of the first tubular barrel; and transferring between ⅔ and ¾ of the platelet poor plasma from the tubular barrel to the attached syringe by advancing a distal end of a rod distally within the lumen of the tubular barrel toward the tip of the tubular barrel pushing the barrel seal distally with the rod and/or retracting the first syringe plunger.

Example 16: The method of Example 15, comprising the steps of:

disconnecting the syringe containing the platelet poor plasma from the tip of the tubular barrel, and discarding the syringe containing the platelet poor plasma;

providing a second syringe having a second plunger movably mounted therein;

connecting the second syringe to the tip of the tubular barrel; and transferring the platelet poor plasma and buffy coat back-and-forth between the tubular barrel and the second syringe thereby mixing the platelet poor plasma and the buffy coat to create platelet rich plasma (PRP).

Example 17: A method for creating PRP, comprising the steps:

providing a device according to Example 3;

inserting the distal end of the tubular barrel with the tube seal mounted thereon into the fluid collection tube;

advancing the tubular barrel and tube seal distally into the fluid collection tube, wherein plasma will flow proximally through the lumen of the tube seal into the tubular barrel pushing the barrel seal proximally, wherein the tubular barrel should be advanced until red blood cells just start to enter into the tube seal; and withdrawing the tubular barrel from the fluid collection tube leaving the tube seal in the fluid collection tube with the remaining red blood cells.

Example 18: The method of Example 17, further comprising the steps:

centrifuging the tubular barrel to separate the plasma and buffy coat into platelet poor plasma and platelet pallet;

providing a first syringe having a first plunger movably mounted therein;

fluidically coupling the first syringe to the tip of the tubular barrel;

inserting the rod into the proximal end of the tubular barrel, and advancing the rod distally within the lumen of the tubular barrel toward the tip pushing the barrel seal distally and transferring any residual air and ⅔-¾ of the platelet poor plasma to the first syringe, or instead of advancing the rod, retracting the plunger of the first syringe to transfer of air and platelet poor plasma;

disconnecting the first syringe with air and the platelet poor plasma from the tip of the tubular barrel;

providing a second syringe having a second plunger movably mounted therein; and fluidically coupling the second syringe with the tip of the tubular barrel, and transferring the platelet pallet and remaining plasma back-and-forth between the tubular barrel and the second syringe.

Example 19: The method of Example 17, wherein after step of inserting the distal end of the tubular barrel with the tube seal mounted thereon into the fluid collection tube, gently removing the tubular barrel with a twisting motion leaving the tube seal engaged with the lumen of the fluid collection tube, placing the proximal end of the tubular barrel in abutment with the tube seal and advancing the tubular barrel to push or advance the tube seal until it contacts the plasma, withdrawing the proximal end of the tubular barrel from the fluid collection tube, and placing the distal end of the tubular barrel in sealing engagement with the tube seal.

Example 20: A method for creating PRP, comprising the steps of:

providing a first syringe having a first plunger movably mounted therein, the first syringe containing a specimen of whole blood;

providing a first tubular barrel having sidewall surrounding a lumen which extends between proximal and distal ends thereof, the first tubular barrel forming a first tip at a distal end, a first barrel seal movingly seated within the lumen of the first tubular barrel, the first barrel seal closing and sealing the proximal end of the first tubular barrel;

fluidically coupling the first syringe to the tip of the first tubular barrel;

transferring the specimen of whole blood from the first syringe into the first tubular barrel by advancing the first plunger within the first syringe, wherein the first barrel seal is pushed toward the proximal end of the first tubular barrel by the blood entering the first tubular barrel;

disconnecting and discarding the first syringe;

centrifuging the first tubular barrel with the whole blood, separating the whole blood into a layer of red blood cells, buffy coat, and plasma;

providing a second syringe having a second plunger movably mounted therein;

fluidically coupling the second syringe to the tip of the first tubular barrel; and transferring the plasma and buffy coat from the first tubular barrel into the second syringe by retracting the second plunger within the second syringe or by advancing the first barrel seal within the first tubular barrel using a rod.

Example 21: The method of Example 20, comprising:

disconnecting and discarding the first tubular barrel;

providing a second tubular barrel having sidewall surrounding a lumen which extends between proximal and distal ends thereof, the second tubular barrel forming a second tip at a distal end, a second barrel seal movingly seated within the lumen of the tubular barrel, the second barrel seal closing and sealing the proximal end of the second tubular barrel;

fluidically coupling the second syringe to the tip of the second tubular barrel;

transferring the plasma and buffy coat from the second syringe into the second tubular barrel; and centrifuging the second tubular barrel to separate the plasma and buffy coat into its constituent platelet poor plasma and platelet pallet.

Example 22: The method of Example 21, comprising:

providing a third syringe having a third plunger movably mounted therein;

fluidically coupling the third syringe to the tip of the second tubular barrel; and transferring any residual air and ⅔-¾ of the platelet poor plasma into the third syringe by either advancing the distal end of the rod within the lumen of the second tubular barrel toward the tip or retracting the third plunger of the third syringe.

Example 23: The method of Example 22, comprising:

disconnecting and discarding the third syringe with the platelet poor plasma;

providing a fourth syringe having a fourth plunger movably mounted therein;

fluidically couple the fourth syringe with the tip of the second tubular barrel; and transferring the platelet pallet and remaining platelet poor plasma back-and-forth between the second tubular barrel and the fourth syringe to dislodge the platelet pallet from the fourth syringe and mix it with remaining plasma thereby creating plasma rich platelets.

Example 24: A method for creating PRP, comprising the steps of:

providing a fluid collection tube containing a sample of whole blood which has been centrifuged to separate the whole blood into layers of red blood cells, buffy coat, and plasma;

providing a first tubular barrel having sidewall surrounding a lumen which extends between proximal and distal ends thereof, the first tubular barrel forming a tip at a distal end, a first barrel seal movingly seated within the lumen of the first tubular barrel, the first barrel seal closing and sealing the proximal end of the tubular barrel;

inserting the tip of the first tubular barrel with a first tube seal mounted thereon into the fluid collection tube;

advancing the first tubular barrel within the fluid collection tube, wherein as the first tubular barrel is advanced distally into the fluid collection tube, plasma enters into the first tubular barrel and pushes the first barrel seal proximally, wherein the first tubular barrel is advanced until ¾ of the plasma has been transferred into the first tubular barrel, leaving the red blood cells, buffy coat, and ¼ of the plasma;

disconnecting and discarding the first tubular barrel with the plasma;

providing a second tubular barrel having sidewall surrounding a lumen which extends between proximal and distal ends thereof, the second tubular barrel forming a tip at a distal end, a second barrel seal movingly seated within the lumen of the second tubular barrel, the second barrel seal closing and sealing the proximal end of the second tubular barrel;

inserting the tip of the second tubular barrel into the fluid collection tube;

advancing the second tubular barrel such that the tip of the second tubular barrel sealingly engages with the first tube seal and continuing to advance the second tubular barrel distally into the fluid collection tube until all of the plasma and the buffy coat are transferred into the second tubular barrel, leaving the red blood cells;

removing the second tubular barrel from the fluid collection tube;

providing a second syringe having a second plunger movably mounted therein;

fluidically coupling the second syringe with the tip of the second tubular barrel; and transferring the plasma and buffy coat back-and-forth between the second tubular barrel and the second syringe to mix the buffy coat with remaining plasma thereby creating plasma rich platelets.

Example 25: A method for creating PRP, comprising the steps of:

providing a fluid collection tube containing a sample of whole blood which has been centrifuged to separate the whole blood into layers of red blood cells, buffy coat, and plasma;

providing a first syringe having a plunger movably mounted therein;

providing a first tube seal on a tip of the first syringe;

inserting the tip of the first syringe with the first tube seal mounted thereon into the fluid collection tube;

advancing the first syringe within the fluid collection tube, wherein as the first syringe is advanced distally into the fluid collection tube, plasma enters into the first syringe and pushes the first plunger proximally, wherein the first syringe is advanced until ¾ of the plasma has been transferred into the first syringe;

disconnecting and discarding the first syringe while leaving the first tube seal mounted within the fluid collection tube;

providing a second syringe having a second plunger movably mounted therein;

inserting a tip of the second syringe into the fluid collection tube;

advancing the second syringe until it sealingly engages with the first tube seal and continuing to advance the second syringe distally into the fluid collection tube until all of the plasma and the buffy coat are transferred into the second syringe; and disconnecting the second syringe from the fluid collection tube, and discarding the fluid collection tube.

Example 26: A method for transferring a first layer of fluid from a fluid specimen tube containing at least two layers of fluid where each fluid had a different specific gravity, using the device of Example 1, comprising the steps of:

providing a tubular barrel having sidewall surrounding a lumen which extends between proximal and distal ends thereof, the tubular barrel forming a tip at a distal end, a barrel seal movingly seated within the lumen of the tubular barrel, the barrel seal closing and sealing the proximal end of the tubular barrel, and a tube seal having a proximal end, a distal end, and a lumen extending therebetween, the proximal end having a frustoconical or chamfered face, the tube seal having an outer diameter sized to sealingly engage with an inner surface of the fluid collection tube, and an inner diameter sized to sealingly engage with an outer surface of the tip of the tubular barrel, the tip of the tubular barrel extending into the tube seal lumen;

inserting the distal end of the tubular barrel into the fluid collection tube such that the tube seal engages with an inner surface of the fluid collection tube;

as the tubular barrel is advanced into the fluid collection tube pushing the tube seal distally, fluid 1 will flow through the tube seal lumen into the lumen of the tubular barrel and the barrel seal is pushed proximally by the plasma flowing into the tubular barrel, wherein the tubular barrel is advanced until fluid 2 just starts to enter into the tubular barrel, at which point the fluid 1 has been transferred to the tubular barrel;

the tubular barrel is withdrawn from the fluid collection tube, leaving the tube seal engaged within the fluid collection tube along with fluid 2.

BRIEF DESCRIPTION OF DRAWINGS

FIG. 1A shows a fluid collection tube with anticoagulant;

FIG. 1B shows the fluid collection tube of FIG. 1A with a sample of whole blood;

FIG. 1C shows the fluid collection tube of FIG. 1B after it has been centrifuged FIG. 1D shows a fluid collection tube of FIG. 1C containing plasma and buffy coat after the red blood cells have been removed;

FIG. 1E shows the fluid collection tube of FIG. 1D after it has been centrifuged FIG. 1F shows the fluid collection tube of FIG. 1E after ¾ of the plasma has been removed leaving ¼ of the plasma and the platelet pallet (collectively PRP)

FIG. 2A depicts a fluid collection tube containing separating gel and anti-coagulant FIG. 2B depicts the fluid collection tube of FIG. 2A with a sample of whole blood FIG. 2C depicts the fluid collection tube of FIG. 2B after it has been centrifuged

FIGS. 9A-9D are drawings illustrating the principle of fluid transfer from tube to syringe due to pressure drop in the syringe;

FIGS. 10A-10F depict a method for transferring at least one layer fluid from a collection tube 602 containing two or more layers of fluid FIGS. 11A-11J are drawings illustrating an example method with tube and regular syringes;

FIGS. 18A-18H, 18I-1, 18I-2, 18J-1, 18J-2, 18K-1, 18K-2, 18L-1, 18L-2, and 18M are drawings illustrating an example method (with a tube and a barrel) of using device 100;

FIGS. 19A-19E, 19F-1, 19F-2, 19G-1, 19G-2, 19H-1, 19H-2, 19I-1, and 19I-2 are drawings illustrating an example method (with a tube and barrels) of using device 100; and FIGS. 20A, 20B-1, 20B-2, 20B-3, 20C-1, 20C-2, 20C-3, 20D-1, 20D-2, 20E-1, 20E-2, 20E-1, 20E-2, 20G-1, 20G-2, 20H-1, 20H-2, 20I-1, 20I-2, 20J-1, 20J-2, 20K-1, 20K-2, 20L-1, 20L-2, and 20M are drawings illustrating an example method (syringe and barrels) of using device 100.

DETAILED DESCRIPTION

Described herein is a tube seal and a barrel, which may be used to facilitate the removal of fluid layers having different density. The examples disclosed herein are described with reference to centrifuging whole blood in order to separate it into its constituent components, each of which has a different density. However, one of ordinary skill in the art will appreciate that the invention is not limited to the constituent layers of whole blood. For instance, the invention can be used in situations/applications when a particular fraction of fluid has to be removed and transferred from specimen tube to another syringe. For example, the invention may be used in the process of obtaining adipose derived tissue stromal vascular fraction (AD-tSVF) from body's fat aspirate, after emulsification and separation into density layers by centrifugation.

The Tube Seal

Figure 2D:
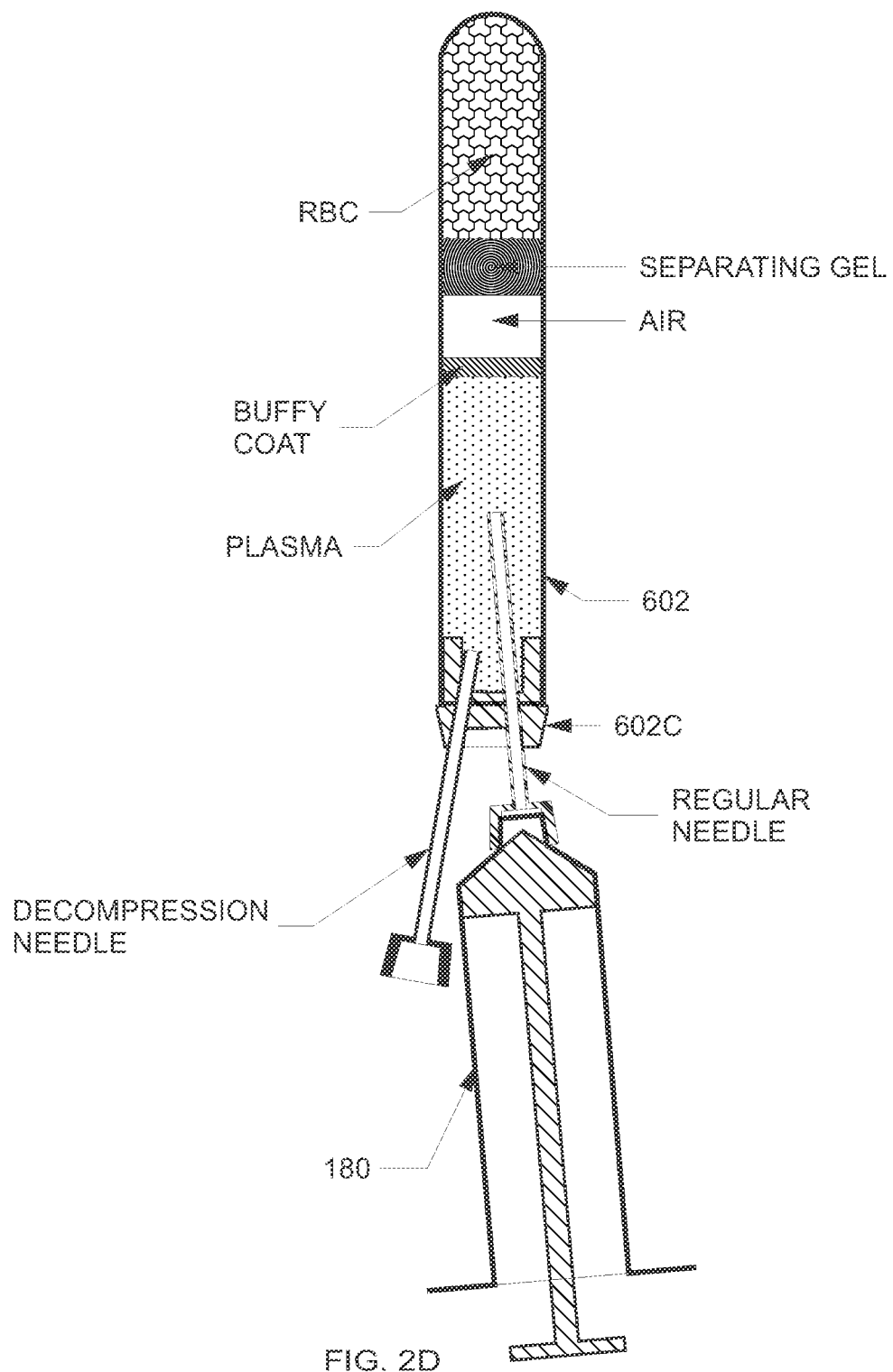
FIG. 2D shows a syringe attached to the fluid collection tube of FIG. 2C FIGS. 3A-3C are drawings illustrating examples of the tube seal in a fluid collection tube.
Figure 3C:
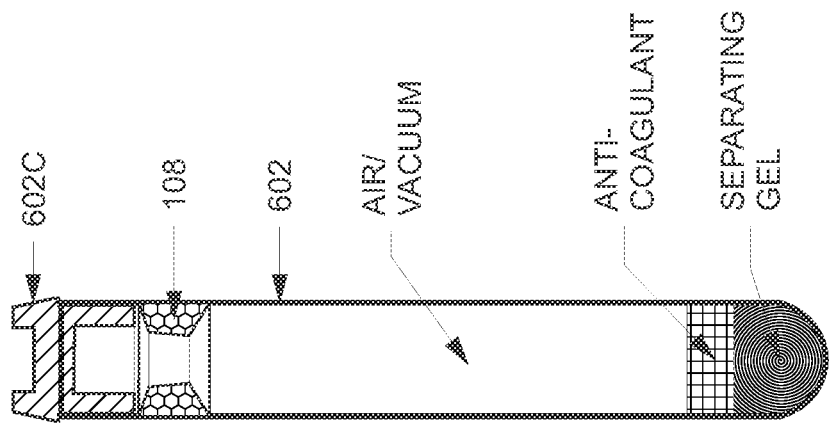
Figure 3B:
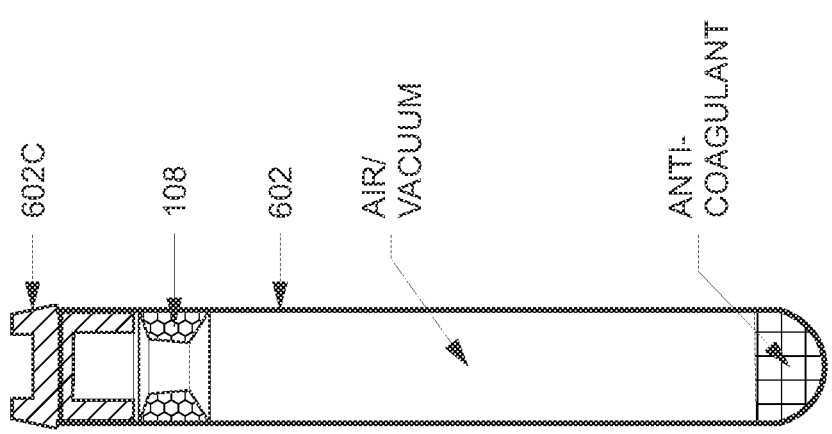
Figure 3A:
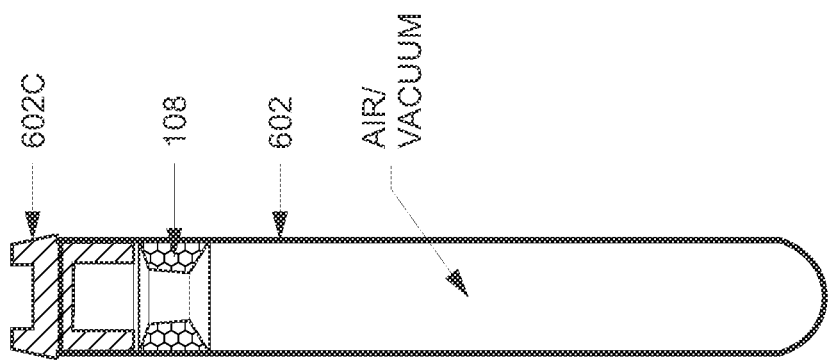

The tube seal may be sized to fit commercially available fluid collection tubes. FIG. 3A shows the tube seal 108 of the present invention inserted into a conventional fluid collection tube 602. FIG. 3B shows the tube seal 108 inserted into a conventional fluid collection tube 602 with an anticoagulant, FIG. 3C shows the tube seal 108 inserted into a conventional fluid collection tube 602 with both an anticoagulant and a separating gel.

Figure 4D:
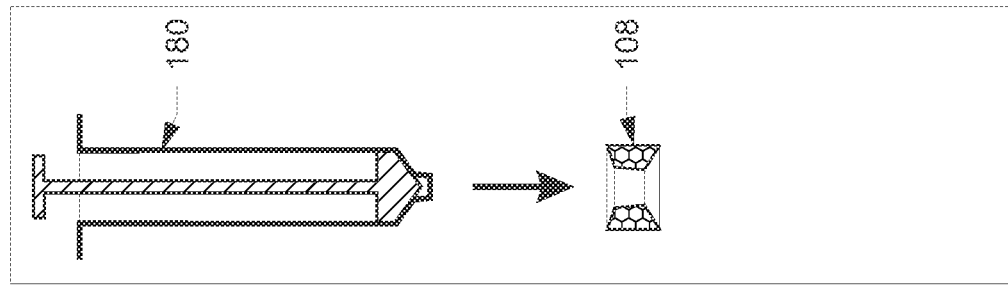
FIGS. 4A-4D show a needleless transfer method for transferring fluid from a fluid collection tube into a syringe using the tube seal
Figure 4C:
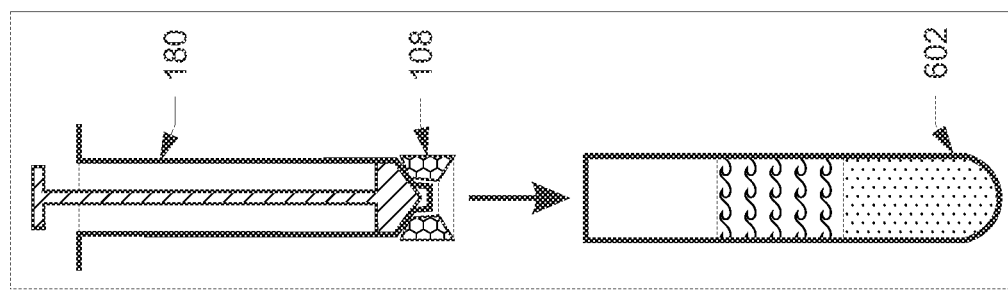
Figure 4B:
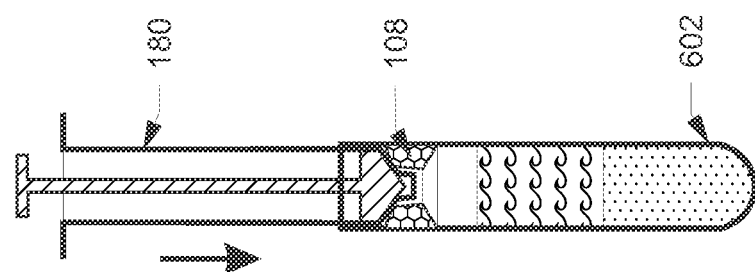
Figure 4A:
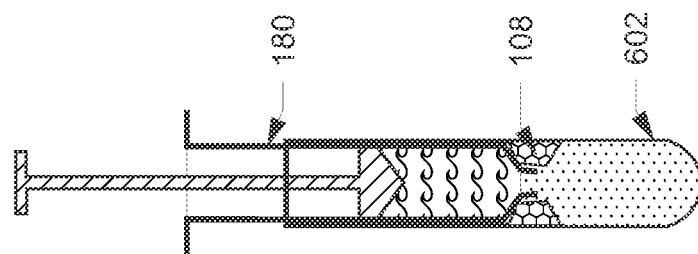

FIG. 4A shows how the tube seal 108 is mounted on a distal end of a conventional syringe 180.

FIG. 4B shows how the syringe 180 with the tube seal 108 is mounted on a distal end thereof is inserted into the mouth of a conventional fluid collection tube 602.

FIGS. 4C, 4D show the syringe 180 with the tube seal 108 is mounted on a distal end thereof is moved distally within the conventional fluid collection tube 602 until a portion of the fluid within the fluid collection tube 602 is transferred into the syringe 180.

In some examples it may be desirable to use a tube seal dispenser to insert the tube seal into the fluid collection tube 602 instead of manually placing the tube seal in the tube with one's hand, or mounting the tube seal on the distal end of the syringe 180. A method of using a dispenser to insert the tube seal into the fluid collection tube 602 using a dispenser is shown in FIGS. 5A-5D.

Figure 5D:
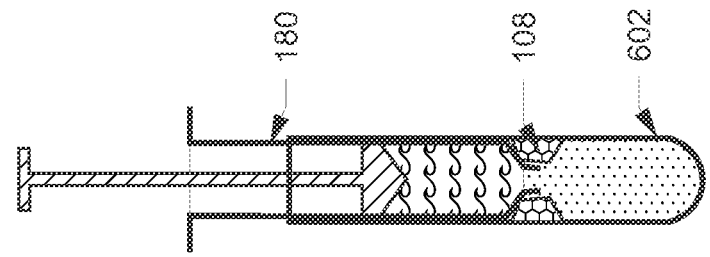
FIGS. 5A-5D show a method for inserting a tube seal into a fluid collection tube using a dispenser.
Figure 5C:
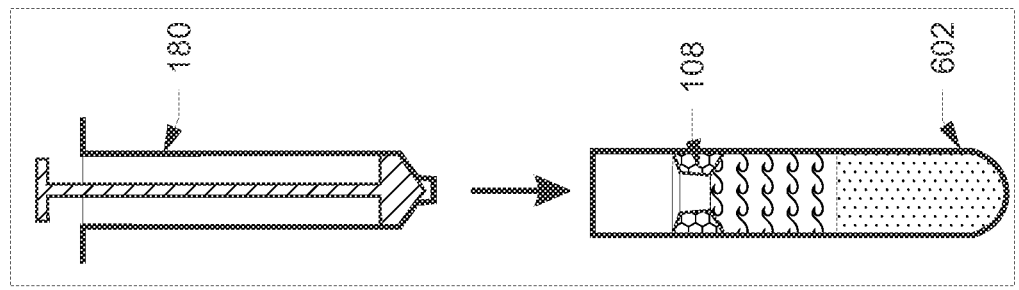
Figure 5B:
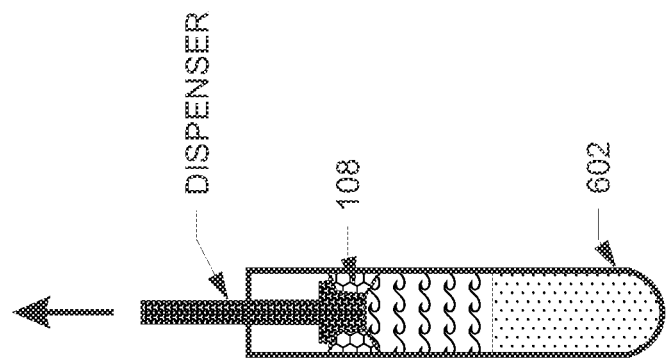
Figure 5A:
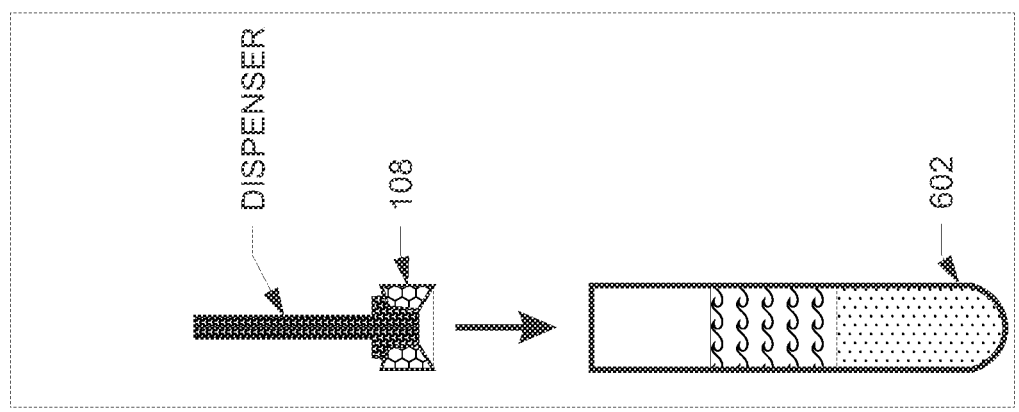

FIG. 5A shows how the tube seal 108 is mounted on a distal end of a dispenser rod.

FIG. 5B shows how the dispenser rod with the tube seal 108 mounted on a distal end thereof is inserted into the mouth of a conventional fluid collection tube 602.

FIGS. 5C, 5D show the syringe 180 is placed in abutment or engagement with the tube seal inside of the fluid collection tube 602, and how the syringe is moved distally within the conventional fluid collection tube 602 until a portion of the fluid within the fluid collection tube 602 is transferred into the syringe 180.

The tube seal 108 (FIGS. 7A, 7B) has a proximal end face 108P and a distal end face 108D. In some examples, the end face 108P, 108D may have a shape 108-2, 108-3 configured to compliment or mattingly engage the tapered end face of a conventional syringe. The tube seal 108 may be formed of resilient, elastomeric material such as rubber.

An outer surface of the tube seal 108 may have a shape which mirrors the shape of the inner surface of the fluid collection tube thereby ensuring sealing engagement therebetween. In some examples, one or more raised sealing rings 108S spanning the outer circumference (surface) of the tube seal may be provided. In the example shown in FIGS. 3A-3C, the fluid collection tube 602 and the tube seal 108 each have a circular cross-section; however, these components may have any complimentary shaped cross-section.

Figure 7B:
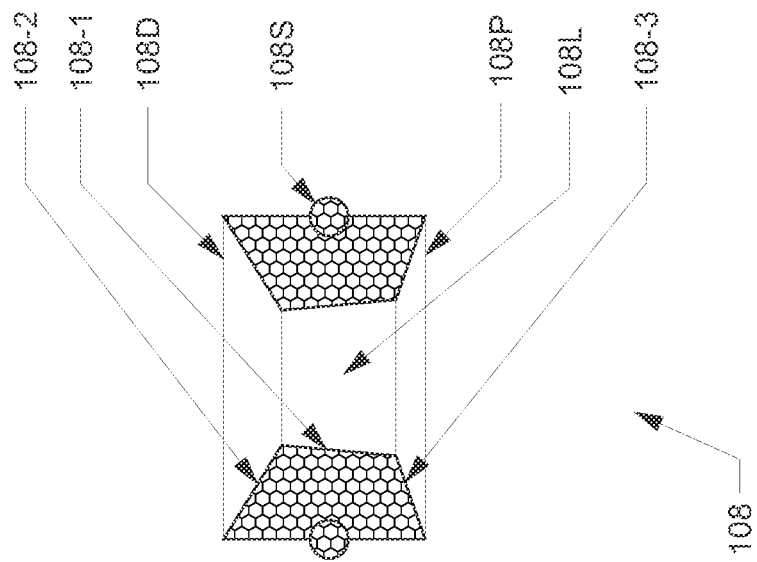
FIGS. 7A-7B are enlarged views of the tube seal.
Figure 7A:
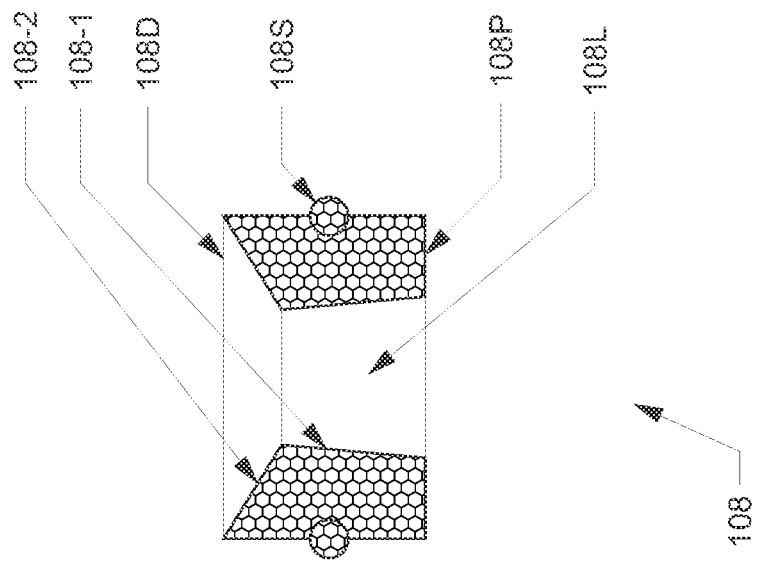

As best seen in FIGS. 7A, 7B, the tube seal 108 has a lumen 108L. In some examples, the lumen 108L has a dual taper with a first taper 108-1 extending from the proximal end face 108P towards the distal end face 108D and a second taper 108-2 extending from the distal end face 108D towards the proximal end face 108P. See, FIG. 7B. Additionally, the inner wall of the tube seal 108 which bounds or surrounds the lumen, may be tapered. In the example depicted in FIG. 7B, the inner wall is tapered such that the lumen 108L is wider at proximal end 108P than at distal end 108D. The inner wall may have a dual taper as desired. The tube seal 108 may be formed of an elastomeric material.

In some examples, the proximal end of the tube seal 108 is of a conical or funnel shape to direct any residual blood through the lumen 108L to the other side of the tube seal 108.

The tube seal 108 is sized to sealingly engage the inner surface of a fluid collection tube. An outer surface of the tube seal 108 may have a shape which mirrors the shape of the inner surface of the fluid collection tube thereby ensuring sealing engagement therebetween.

In some examples, the proximal end face 108P of the tube seal 108 may have a shape which compliments or mattingly engages the tapered end face of the barrel 106.

In some examples, the proximal end of the tube seal 108 is of a conical or funnel shape to direct any residual blood through the lumen 108L to the other side of the tube seal 108.

The tube seal 108 may be provided by itself or as part of a kit or assembly. The kit may include a fluid collection tube, cap for fluid collection tube, and tube seal. In some examples, the fluid collection tube will be prefilled with an anticoagulant. In some examples, the fluid collection tube will be prefilled with an anticoagulant and a separating gel. In some examples, the tube seal is preloaded into the fluid collection tube. In some examples, the kit may include a dispenser for introducing the tube seal into the tube. The tube seal may also be pre-mounted on the tip of a conventional syringe or any syringe-like device.

Throughout this disclosure, the term syringe should be understood to encompass any syringe or syringe-like device.

Figure 8D:
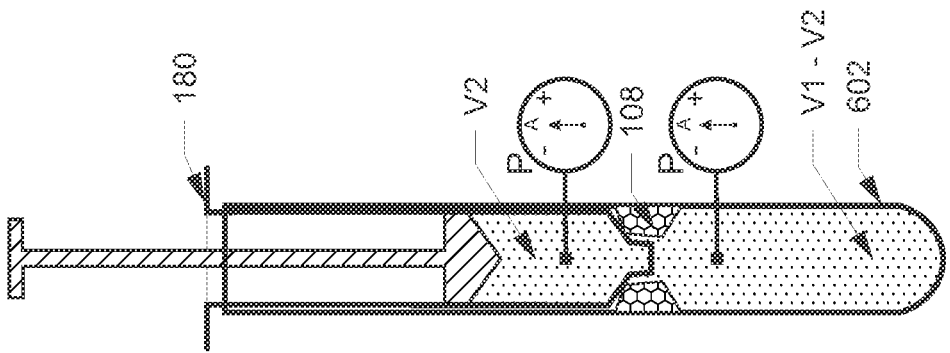
FIGS. 8A-8D are drawings illustrating the principle of fluid transfer from tube to syringe due to positive pressure build up in the tube.
Figure 8C:
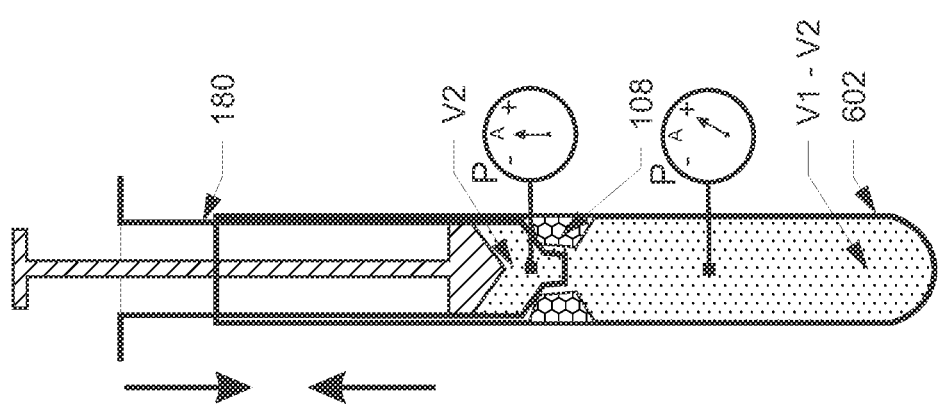
Figure 8B:
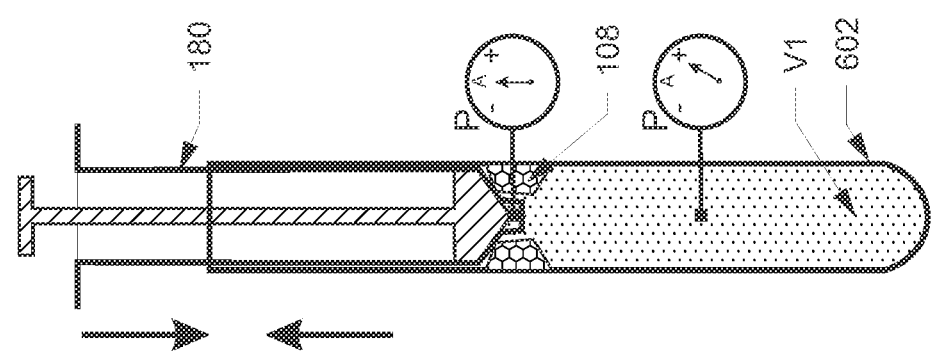
Figure 8A:
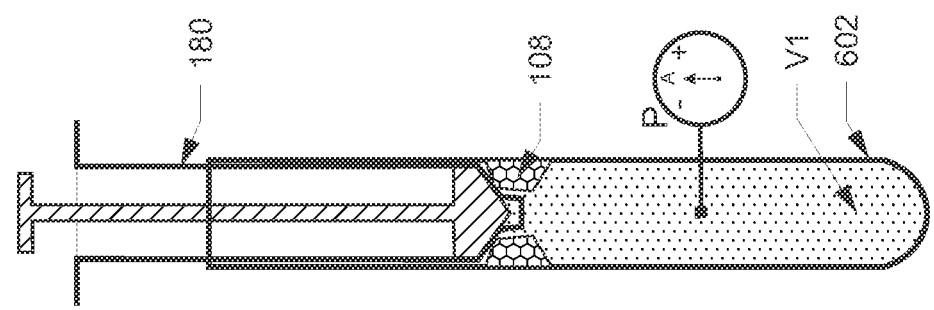

As will be explained below, the tube seal 108 may be used as a connector and adapter for transferring fluids between a fluid collection tube and a syringe, and provides a fluidic connection between the tube and the syringe. In some examples the tube seal facilitates fluid transfer from the tube to the syringe due to a pressure rise in the tube (caused by advancing the syringe distally and exerting a pressure against the tube seal) FIGS. 8A-8D. FIG. 8A shows a fluid collection tube 602 containing a volume V1 of fluid (at ambient pressure A), a tube seal 108 and a syringe 180. FIG. 8B shows the fluid collection tube 602 and the syringe 180 of FIG. 8A after the syringe 180 has been advanced distally into the fluid collection tube 602 thereby increasing the pressure of the volume of fluid V1 (in the moment before fluid is transferred into the syringe due to the pressure gradient therebetween). FIG. 8C shows the fluid collection tube 602 and syringe 180 of FIG. 8B after a volume V2 has been transferred from the fluid collection tube 602 to the syringe 180 due to the pressure gradient therebetween (in the moment before the pressure in the fluid collection tube 602 goes back to ambient. FIG. 8D shows the fluid collection tube 602 and syringe 180 of FIG. 8C after a volume V2 has been transferred to the fluid collection tube 602 to the syringe 180 due to the pressure gradient therebetween, after the pressure in the fluid collection tube 602 goes back to ambient.

In some examples the tube seal facilitates fluid transfer from the tube to the syringe due to a pressure drop in the connected syringe (caused by retracting the plunger proximally and creating suction in the syringe) FIG. 9A shows a fluid collection tube 602 containing a volume V1 of fluid (at ambient pressure A), a tube seal 108 and a syringe 180. FIG. 9B shows the fluid collection tube 602 and the syringe 180 of FIG. 9A after the plunger of syringe 180 has been retracted proximally thereby decreasing the pressure within the syringe 180 below ambient (in the moment before fluid is transferred into the syringe due to the pressure gradient therebetween). FIG. 9C shows the fluid collection tube 602 and syringe 180 of FIG. 9B after a volume V2 has been transferred from the fluid collection tube 602 to the syringe 180 due to the pressure gradient therebetween (in the moment before the pressure in the syringe 180 goes back to ambient. FIG. 9D shows the fluid collection tube 602 and syringe 180 of FIG. 9C after a volume V2 has been transferred to the fluid collection tube 602 to the syringe 180 due to the pressure gradient therebetween, after the pressure in the syringe 180 goes back to ambient.

Generic Process of Fluid Transfer

Turning now to FIGS. 10A-10F, a method for transferring at least one layer fluid from a collection tube 602 containing two or more layers of fluid, where each layer of fluid has a different specific gravity will be explained. The generic process used to transfer fluid from a fluid collection tube 602 to a syringe 180 utilizing the tube seal 108 will be explained.

In FIG. 10A, a fluid collection tube 602 containing a fluid specimen is centrifuged to separate the fluid specimen into its constituent components by density: layer 1, layer 2, and layer 3. One of ordinary skill in the art will appreciate that the method may be used with any number of different density fluid layers.

In FIG. 10B, cap 602C is removed from the fluid collection tube 602, and tube seal 108 is inserted into the mouth of the fluid collection tube 602. One of ordinary skill in the art will appreciate that the tube seal 108 may be inserted into the fluid collection tube 602 prior to the centrifuging step illustrated in FIG. 10A. Or the fluid collection tube 602 may be equipped or supplied with the tube seal already inside the tube prior to insertion of the fluid.

In FIGS. 10C, 10D, a syringe 180 (without a needle) is inserted into the mouth of the fluid collection tube 602 such that the distal tip of the syringe 180 is placed in sealing engagement with the tube seal 108.

Figure 10E:
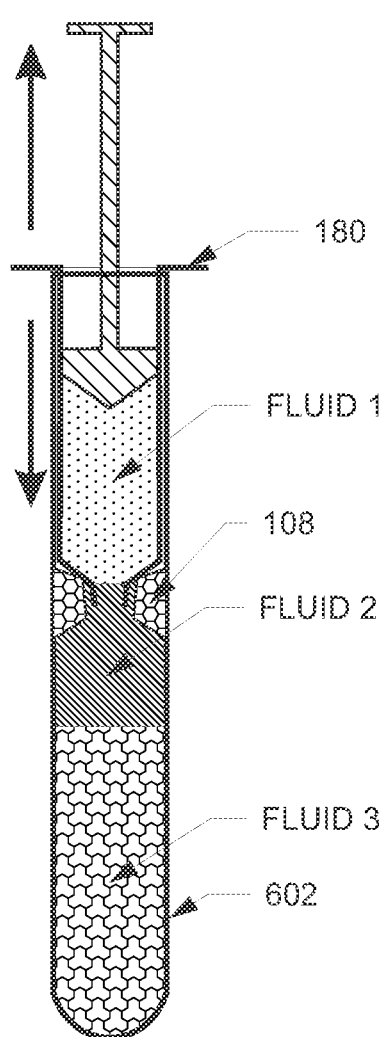

In FIG. 10E, as the syringe 180 is advanced distally into the fluid collection tube 602, fluid 1 is displaced from the fluid collection tube 602 into the syringe 180. The tube seal 108 seals the fluid collection tube 602 with the syringe, enabling the transfer of fluid. It should be appreciated that the plunger of the syringe 180 may be retracted instead of or in addition to advancing the syringe 180 distally into the fluid collection tube 602.

Figure 10F:
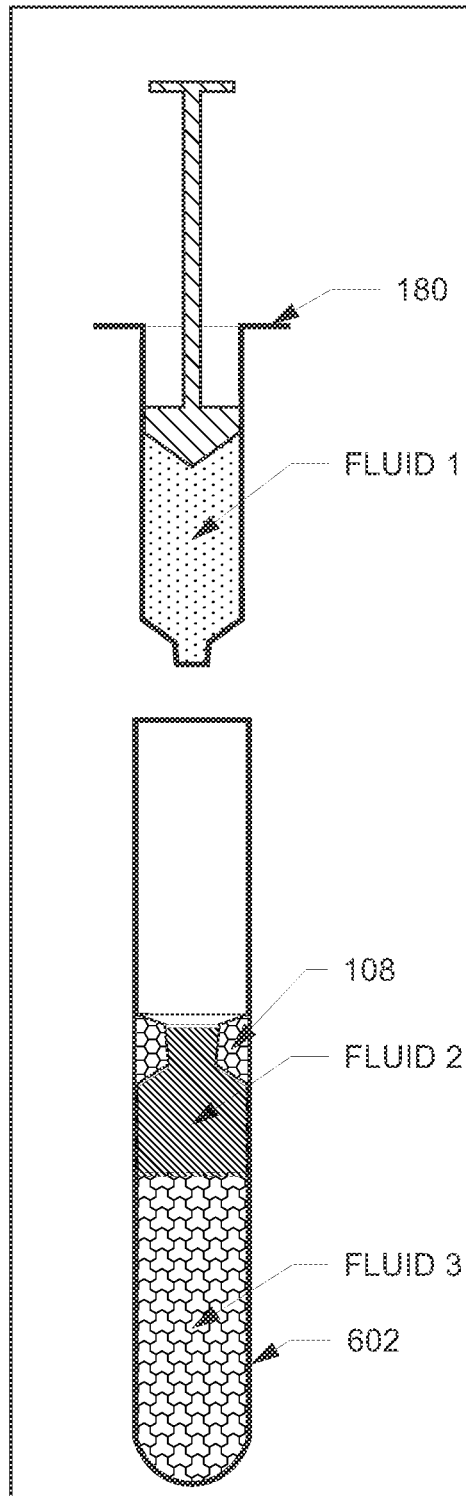

If FIG. 10F, the syringe 180 containing fluid 1 may be removed from the tube seal 108 upon the transfer or displacement of the desired quantity of fluid 1. One of ordinary skill will appreciate that the syringe 180 may be removed from the tube seal 108 and at any time, and a new syringe or syringe-like device 180 may be introduced to transfer desired quantities of the remaining fluids 1, 2, 3.

Example PRP Extraction Using the Tube Seal with Ordinary Syringes (One-Spin)

Turning now to FIGS. 11A-11J, a method for transferring fluid from a fluid collection tube 602 to a syringe 180 utilizing the tube seal 108 will be explained. The example process pertains to the creation of platelet rich plasma but one of ordinary skill in the art will appreciate that the tube seal may be used generally to facilitate fluid transfer.

Figure 11A:
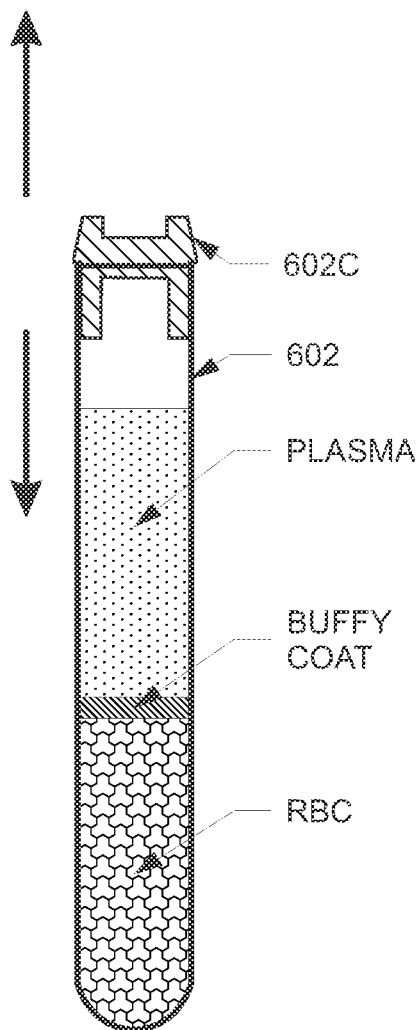

In FIG. 11A, a fluid collection tube 602 containing a specimen of whole blood is centrifuged to separate the whole blood into its constituent components by density: red blood cells (RBC), buffy coat, and plasma.

Figure 11B:
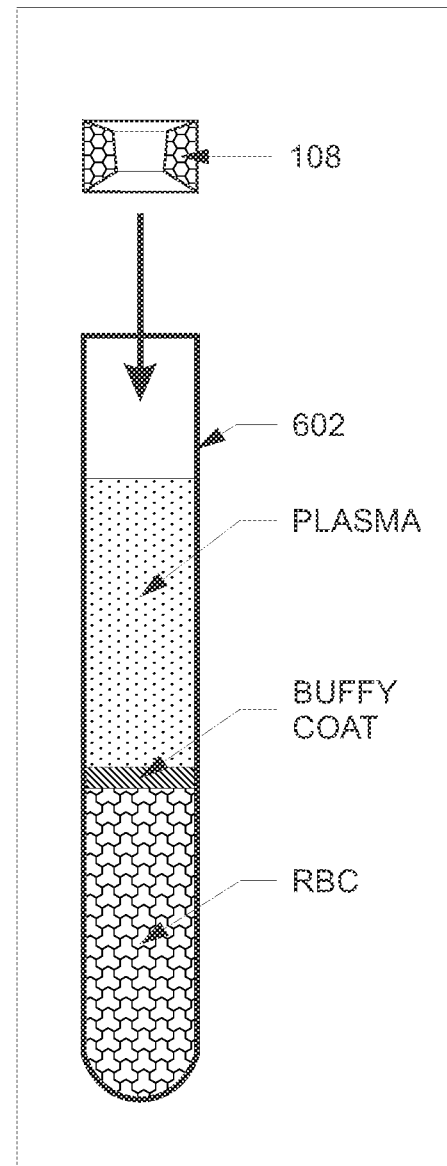

In FIG. 11B, cap 602C is removed from the fluid collection tube 602, and tube seal 108 is inserted into the mouth of the fluid collection tube 602. One of ordinary skill in the art will appreciate that the tube seal 108 may be inserted into the fluid collection tube prior to the centrifuging step illustrated in FIG. 11A. Or the tube may be equipped or supplied with the tube seal already inside the tube prior to fluid collection.

In FIGS. 11C, 11D, a syringe 180 (without a needle) is inserted into the mouth of the fluid collection tube 602 such that the distal tip of the syringe 180 is placed in sealing engagement with the tube seal 108.

Figure 11E:
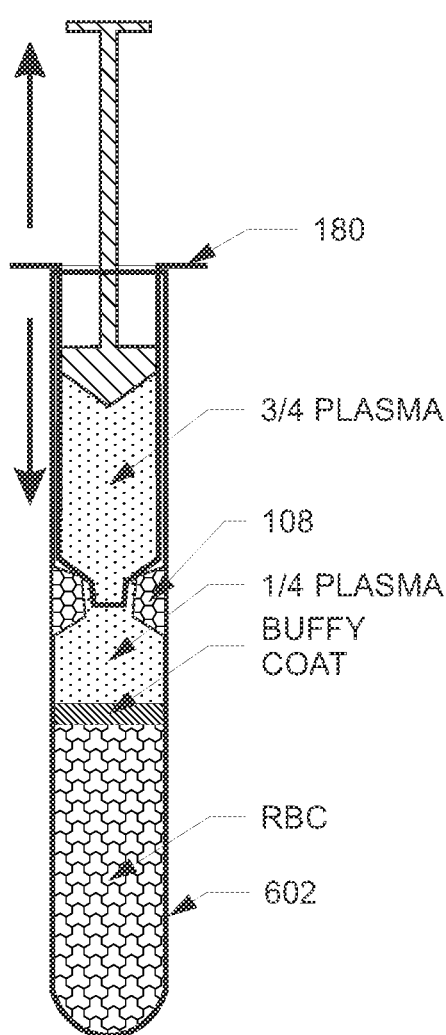

In FIG. 11E, as the syringe 180 is advanced distally into the fluid collection tube 602, plasma is displaced from the fluid collection tube 602 into the syringe 180 until between ⅔ and ¾ (by volume) of the plasma is transferred into the syringe. The tube seal 108 seals the fluid collection tube 602 with the syringe, enabling the transfer of fluid. It should be appreciated that the plunger of the syringe 180 may be retracted instead of or in addition to advancing the syringe 180 distally into the fluid collection tube 602.

Figure 11F:
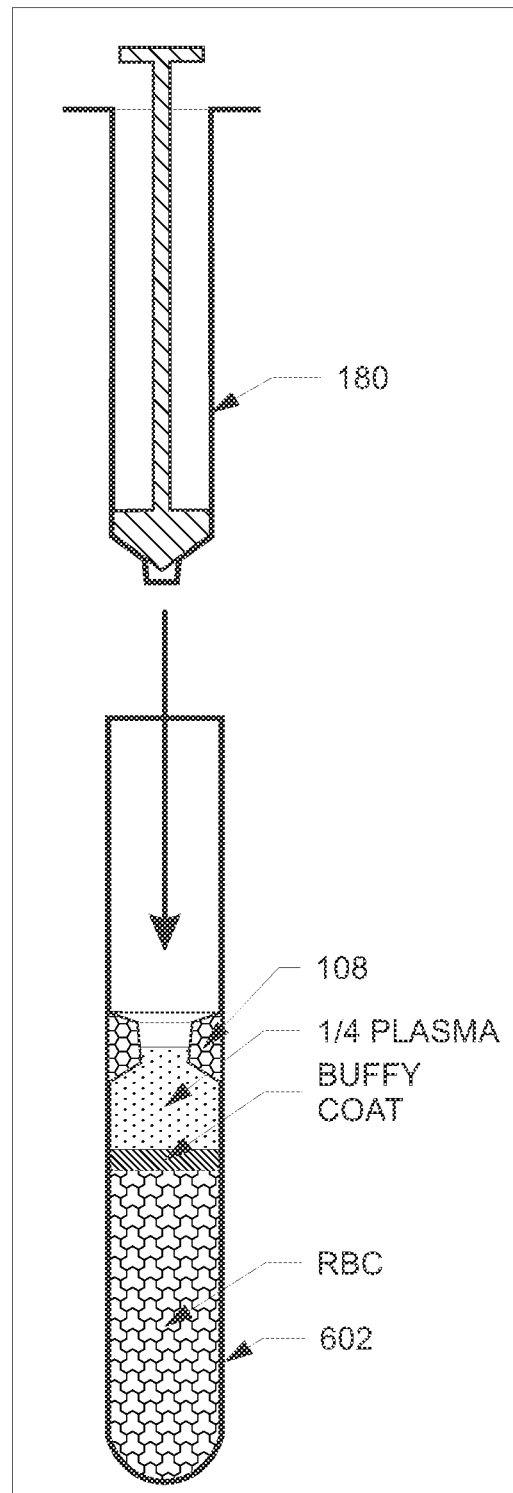

In FIG. 11F, the syringe 180 with the plasma is discarded, and a fresh (empty) syringe 180 is placed into sealing engagement with the tube seal 108.

Figure 11G:
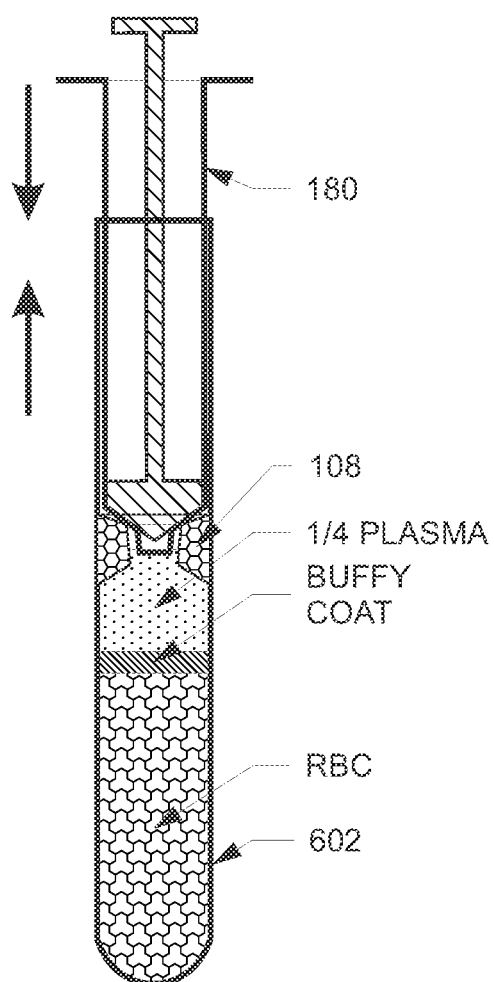
Figure 11H:
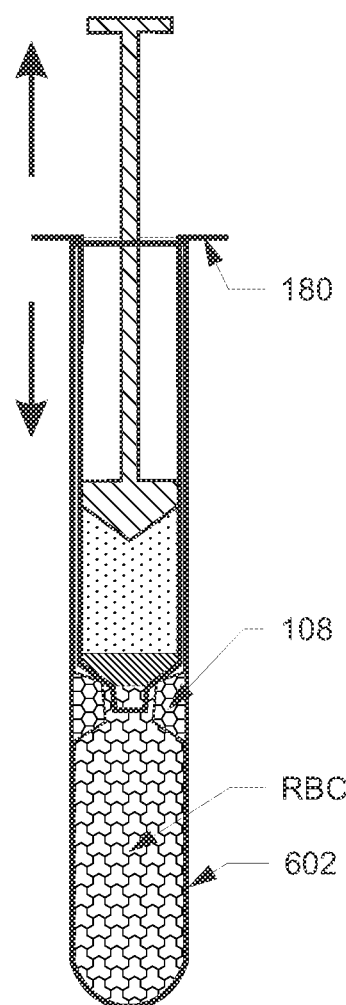

In FIGS. 11G, 11H, the syringe 180 and the tube seal 108 are advanced distally such that the remaining plasma and the buffy coat (collectively PRP) are transferred into the syringe 180. Again, the tube seal 108 seals the fluid collection tube 602 and the syringe 180, enabling the transfer of fluid. Also, the plunger of the syringe 180 may be retracted instead of or in addition to advancing the syringe 180 distally into the fluid collection tube 602.

Figure 11I:
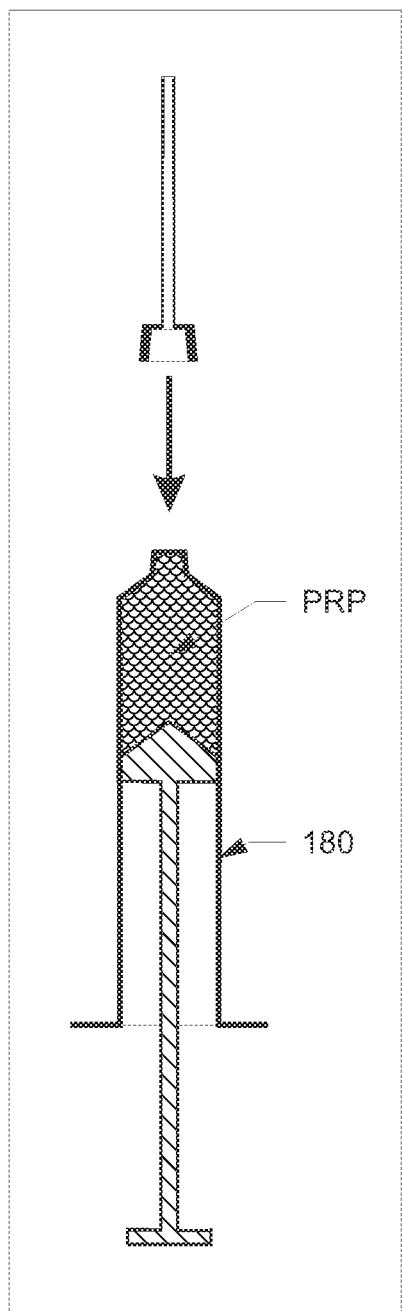
Figure 11J:
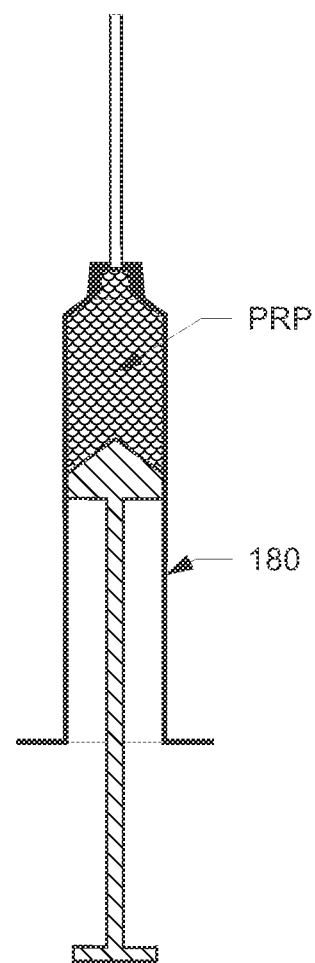

In FIGS. 11I and 11J, the syringe 180 with the PRP is withdrawn from the fluid collection tube 602, and a needle is attached to the syringe.

The aforementioned process using the tube seal 108 is an improvement over the conventional process for creating PRP, because it eliminates the needles, eliminates separating gel, and does not solely rely on aspiration.

Also disclosed is a system and kit for obtaining PRP using the tube seal 108, as well as associated methods for separating platelet rich plasma ("PRP") from whole blood. The system, kit, and associated methods of the present invention addresses several shortcomings of conventional PRP kits in that it reduces the number of components needed, eliminates the need for a separating gel, in some examples enables separation of PRP from the tube after a single centrifuge spin cycle, eliminates the need for needles thereby reducing the risk of accidental needle stick, is simpler to use, and reduces the risk of sample contamination.

The Barrel

As will be explained below, the barrel 106 is a fluid transfer receptacle equipped with a piston-like barrel seal 108. The barrel is sized to fit within the lumen of a standard fluid collection tube. The barrel features a tip, whose outer surface is capable of sealingly engaging with the tube seal, and an inner surface capable of sealingly engaging with a male Luer connector of a syringe. The below mentioned process using the tube seal 108 with the barrel 106, is an improvement over the conventional process for creating PRP, because while the tube seal eliminates the needles and separating gel and does not solely rely on aspiration, the barrel replaces both the transfer syringe and the second-spin tube.

The barrel seal 108 may be formed of an elastomeric material which may be the same material used to form the tube seal.

Figure 12:
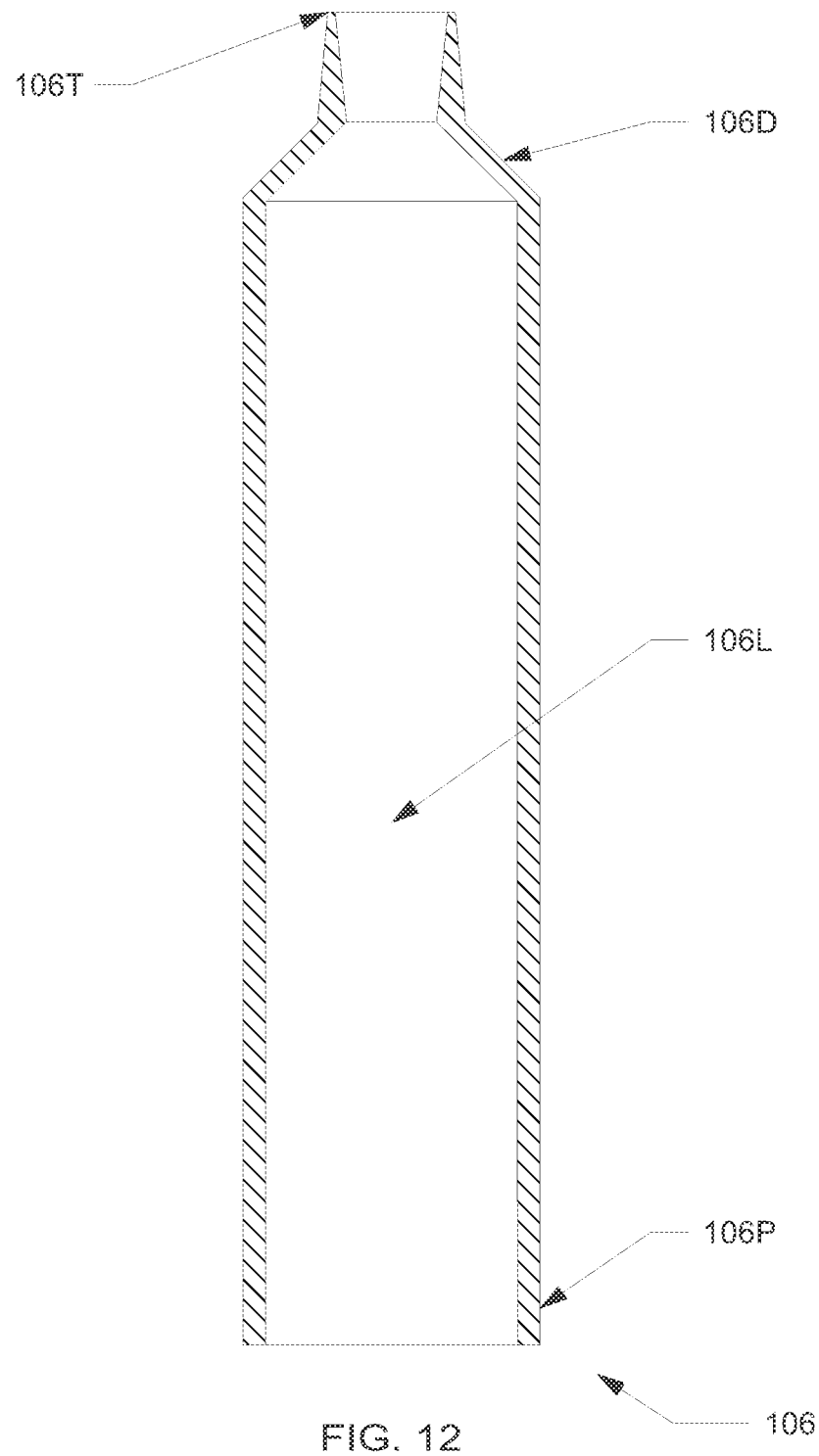
FIG. 12 is an enlarged view of the barrel of device 100.

FIG. 12: The barrel 106 is an elongate hollow tube having sidewalls which surround a central lumen 106L. A proximal end 106P of the barrel is open and communicates with the lumen 106L. A distal portion of the barrel gradually tapers narrower to a kind of Luer tip 106T. In some examples the distal end 106D is conical shaped. The tip 106T tappers narrower. A width of the sidewall of the barrel 106 is less than gap G, and a diameter of lumen 106L is greater than the diameter of the rod 103. The distal end of the rod 103 fits into the proximal end of the barrel 106 and the rod 103 can be loosely inserted into the lumen 106L.

The barrel 106 may have the general appearance of a conventional syringe but in some examples differs from a conventional syringe in several key aspects. One notable difference is that barrel 106 is not meant to be equipped with a needle. The outer side of the tip 106T forms an oversized male to sealingly engage with a tube seal 108, and cannot accommodate a needle. The inner side of the tip 106T forms a female Luer connection configured to sealingly engage with a male Luer connection of a regular syringe. Another notable difference is that the proximal end 106P of the barrel 106 lacks the flanges or gripping portions provided on conventional syringes which are used to assist advancing the plunger. The barrel 106 is never used to inject anything. Lacking a flange and without the plunger rod, the barrel 106 is configured to be securely received within a conventional centrifuge device.

Figure 13:
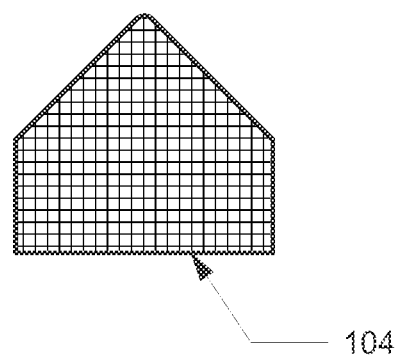
FIG. 13 is an enlarged view of the barrel seal of device 100.

The barrel seal 104 (FIGS. 13, 16) is movably provided within the lumen 106L and will only move when pushed proximally by fluid entering the barrel 106 through the Luer tip 106T or when advanced distally by the rod 103.

Figure 17A:
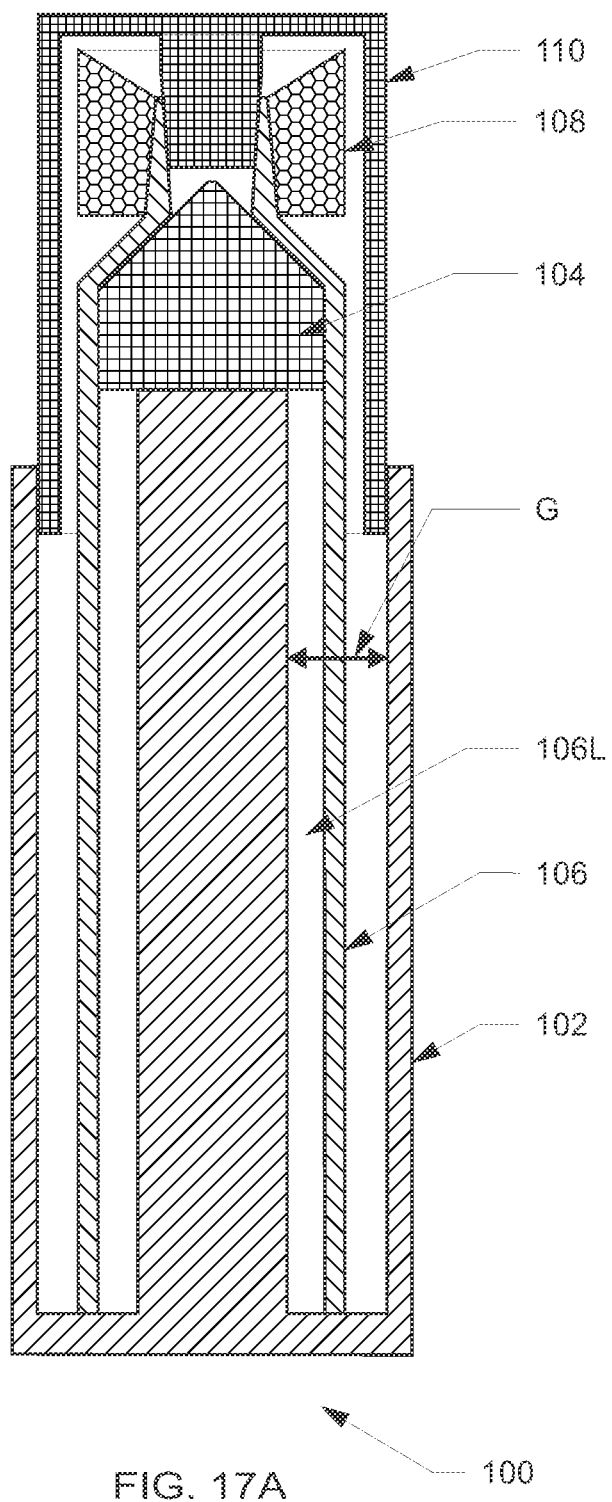
FIGS. 17A-17B are views of the device 100 fully assembled.
Figure 17B:
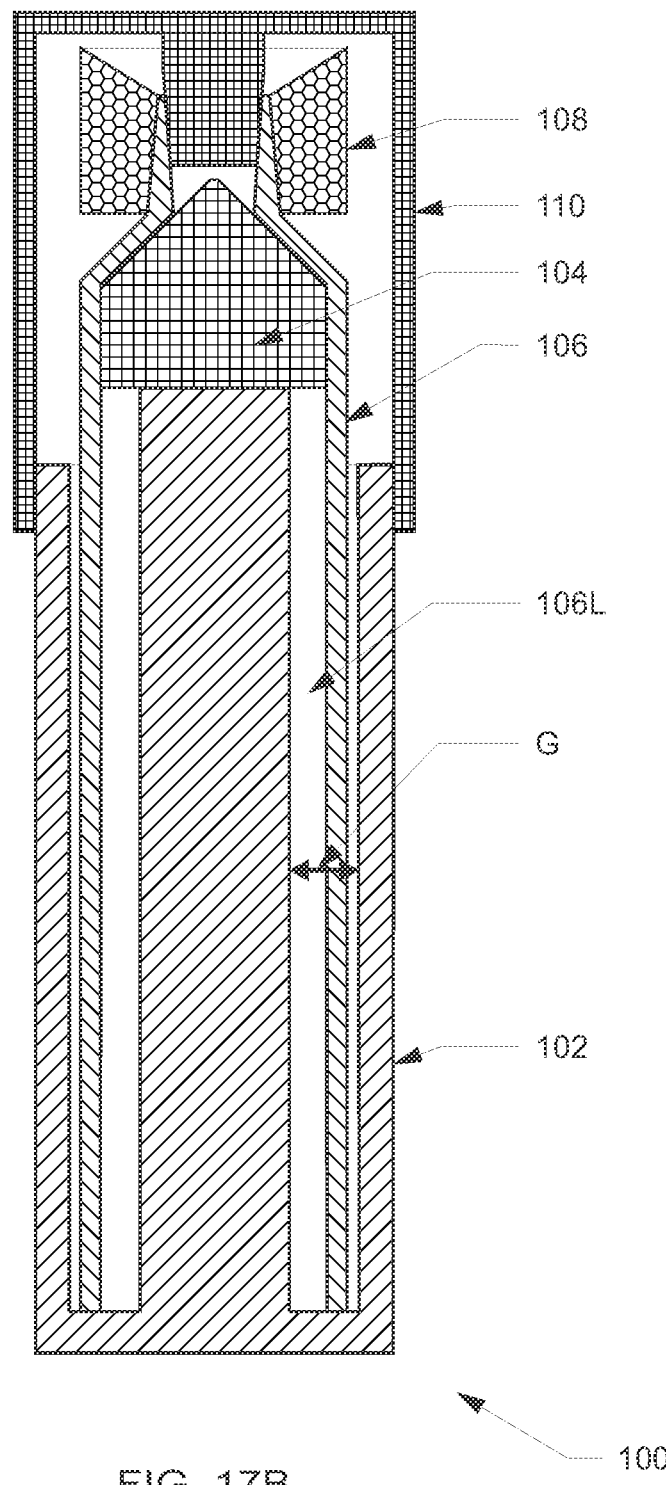

As best seen in FIGS. 17A, 17B the rod 103 fits within lumen 106L while the barrel 106 fits in the gap G between the rod 103 and the barrel 106.

Figure 15B:
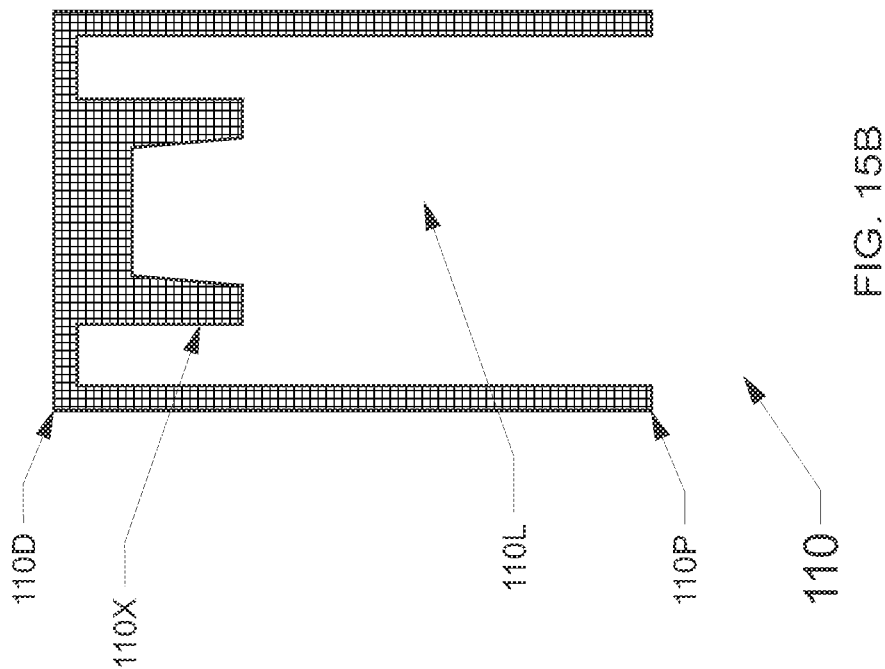
FIGS. 15A-15B are enlarged views of the cap 100.
Figure 15A:
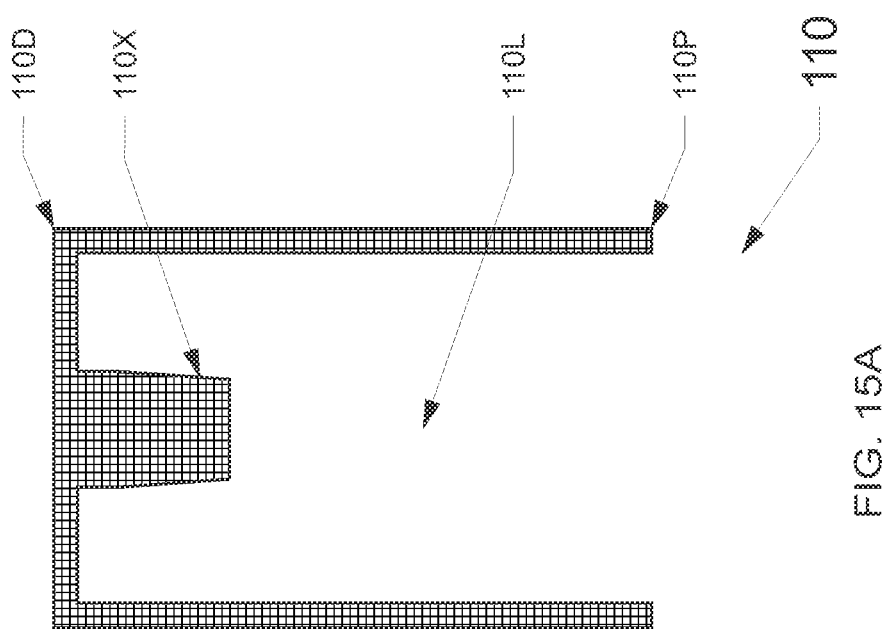

As best seen in FIGS. 15A, 15B, the barrel cap 110 is an elongate hollow tube having a central lumen 110L. In some examples, a proximal end 110P is open and communicates with the lumen 110L, and distal end 110D is closed. In FIG. 15A, the barrel cap 110 includes a male plug 110X attached to an inner surface thereof which is configured to sealingly engage the female aspects of the lumen of the tip 106T. In FIG. 15B, the barrel cap 110 includes a female plug 110X which is configured to sealingly engage the exterior wall of the tip 106T.

FIGS. 17A, 17B show the device 100 fully assembled with the barrel seal 104 within the barrel 106, the barrel 106 coaxially mounted over the rod 103 and received within the casing 102, the tube seal 108 removably mounted on the tip 106T, and the barrel cap 110 mounted over the tube seal 108 and a distal portion of the barrel 106. In FIG. 17A the distal most part of the casing 102 overlaps the barrel cap 110, whereas in FIG. 17B the distal most portion of the cap overlaps the distal most part of the casing 102.

Figure 6:
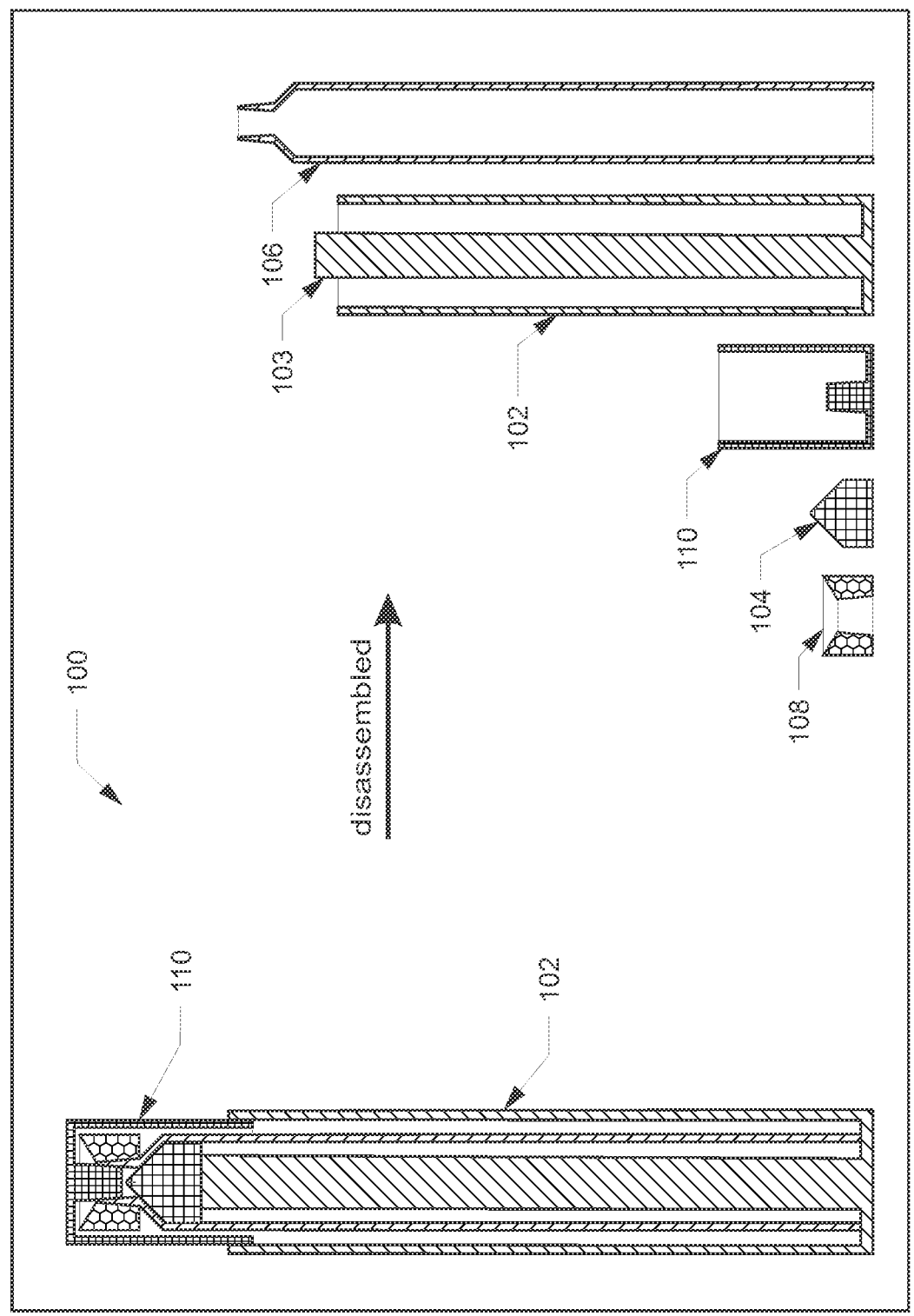
FIG. 6 shows a fully assembled view and an exploded view of device 100.

FIG. 6 shows a fully assembled view and an exploded view of device 100.

It should be noted that the device 100 does not utilize needles to transfer the plasma and buffy coat out of the fluid collection tube 602 and eliminates the need for using a separating gel.

Figure 16:
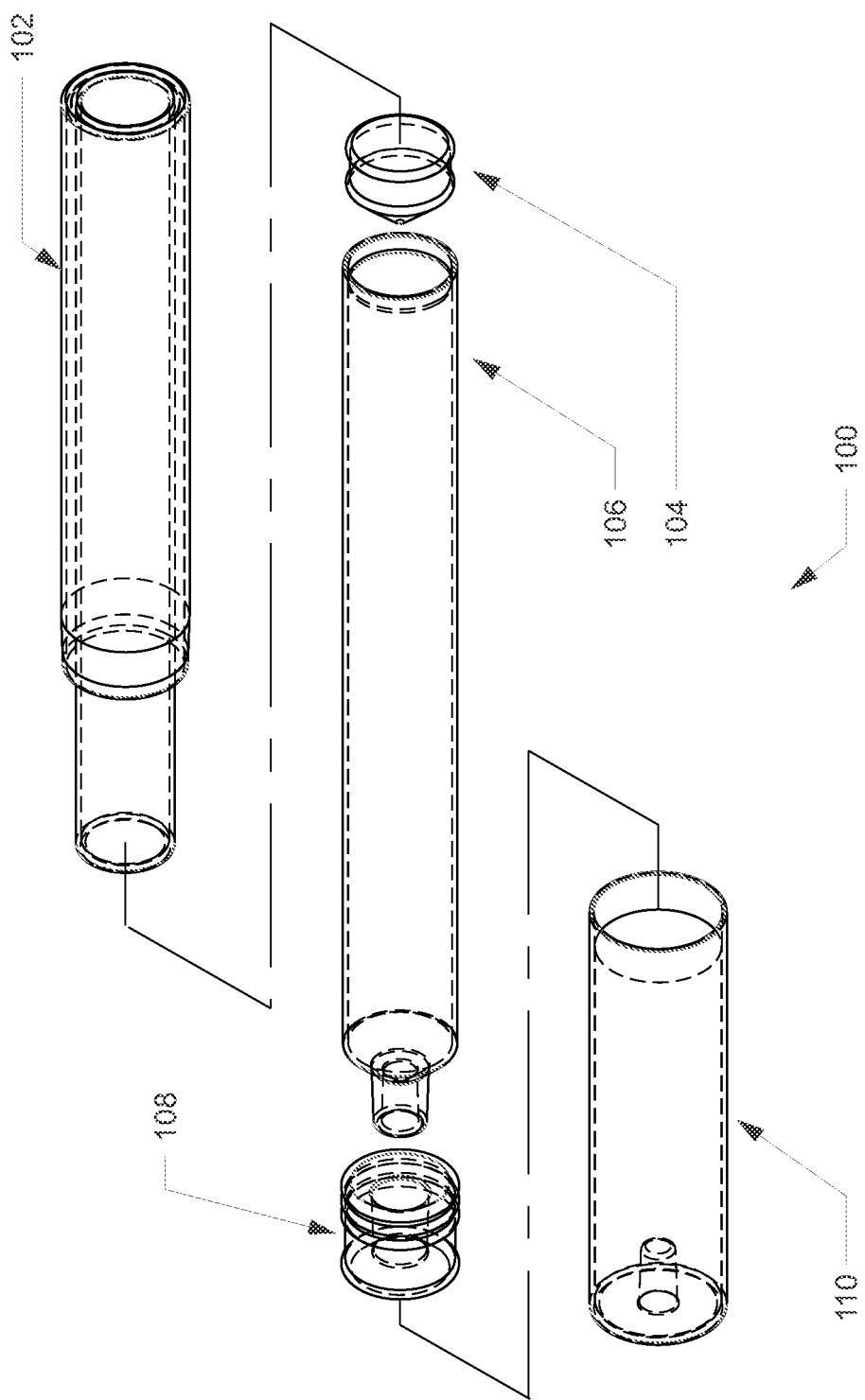
FIG. 16 is an exploded view of an example PRP device 100.

FIG. 16 is an exploded view of an example device 100 which includes a casing 102 (FIGS. 14A, 14B) with its rod 103, a barrel seal 104 (FIG. 13), a barrel 106 (FIG. 12), a tube seal 108 (FIGS. 7A, 7B) and a barrel cap 110 (FIGS. 15A, 15B).

Figure 14A:
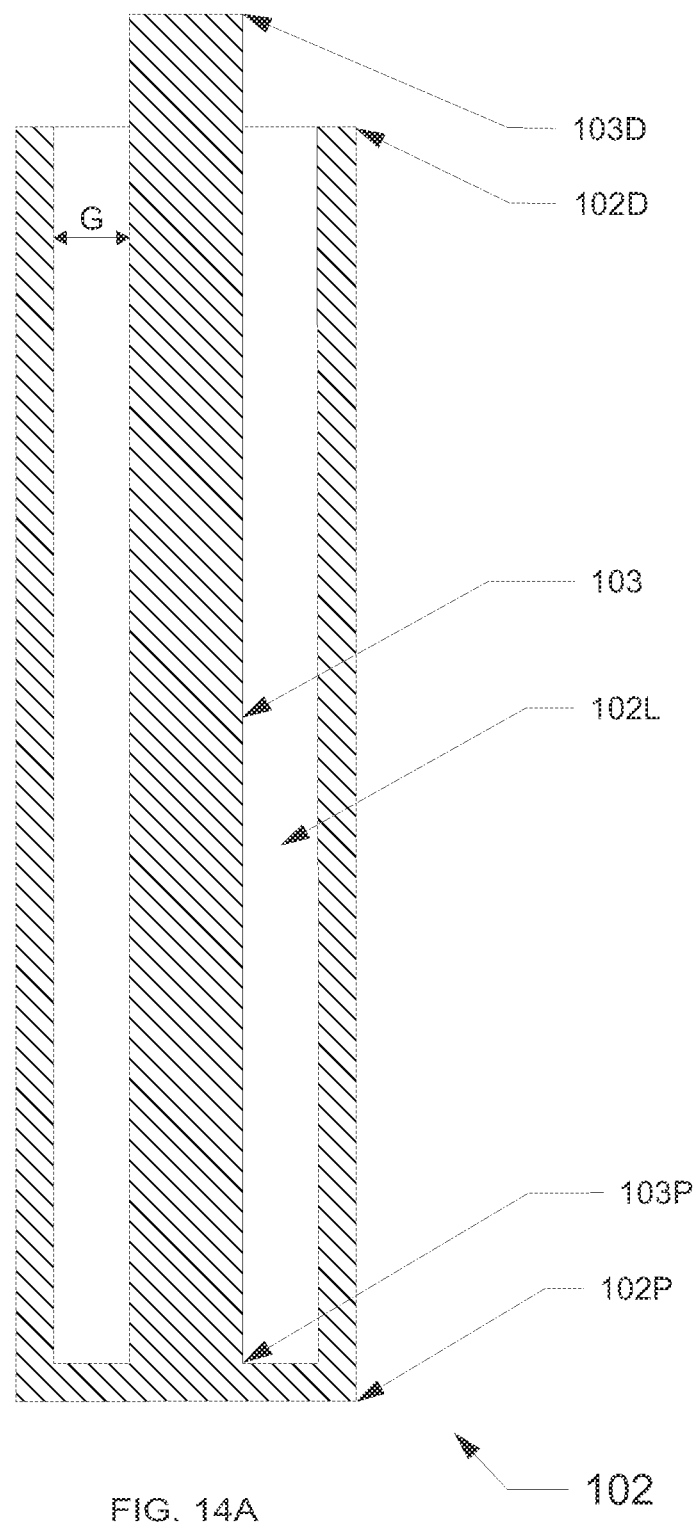
FIGS. 14A-14B are enlarged views of case of device 100.
Figure 14B:
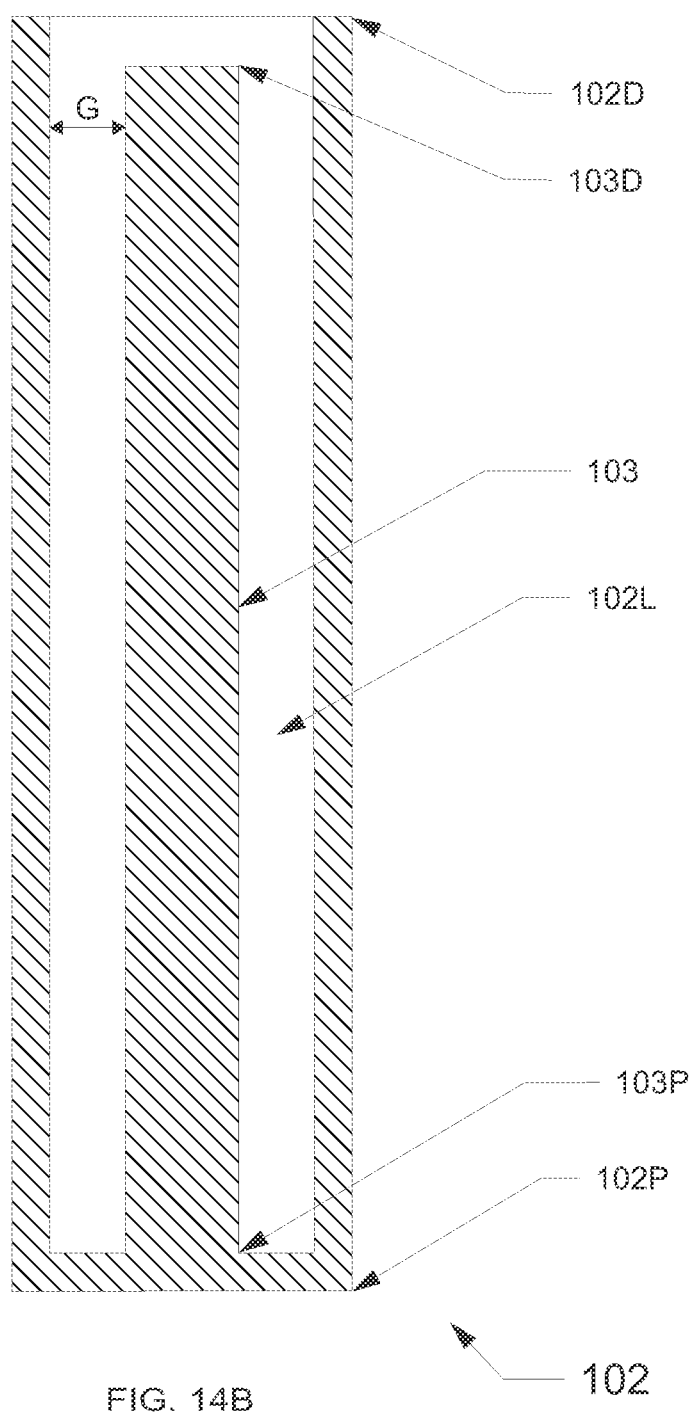

FIGS. 14A, 14B: The casing 102 is an elongate hollow tube with a central lumen 102L. In some examples, proximal end 102P of the casing 102 is closed, and distal end 102D is open and communicates with the central lumen 102L. A rod 103 is partially housed within the central lumen 102L. In FIG. 14A, a distal end 103D extends beyond the distal end 102D of the casing 102. In FIG. 14B, the distal end 102D of the casing extends beyond the distal end 103D of the rod 103. In some examples, the rod 103 is attached to the casing. For example, a proximal end 103P of the rod 103 may be attached to the proximal end 102P of the casing 102. The diameter of the lumen 102L is greater than the diameter of the rod 103 such that a gap G is formed between an external surface of the rod 103 and an interior wall of the casing 102.

The rod 103 may be hollow or solid. The rod 103 serves to advance the barrel seal 104 (FIGS. 13, 16) from a proximal end 106P of the barrel 106 towards the distal end 106D of the barrel. The barrel seal 104 may be formed of an elastomeric material and fluidically seals the inner surface or lumen 106L of the barrel 106. In some examples, the barrel seal 104 abuts but is not attached to the rod 103. In this example, once the rod 103 has advanced the seal 104 distally, retracting the rod 103 proximally will not retract the seal 104. However, in other examples, the seal 104 may be attached to the rod 103.

The rod 103 may have any shape and need not have a circular cross-section. The rod 103 must merely have sufficient structural integrity to advance the barrel seal 104 within the lumen 106L.

Example PRP Extraction Using the Tube Seal with the Barrel (Two-Spin)

FIGS. 18A-18M illustrate steps in a method using device 100. Some of the steps are optional, and the order in which the steps are described are not limiting.

Figure 18A:
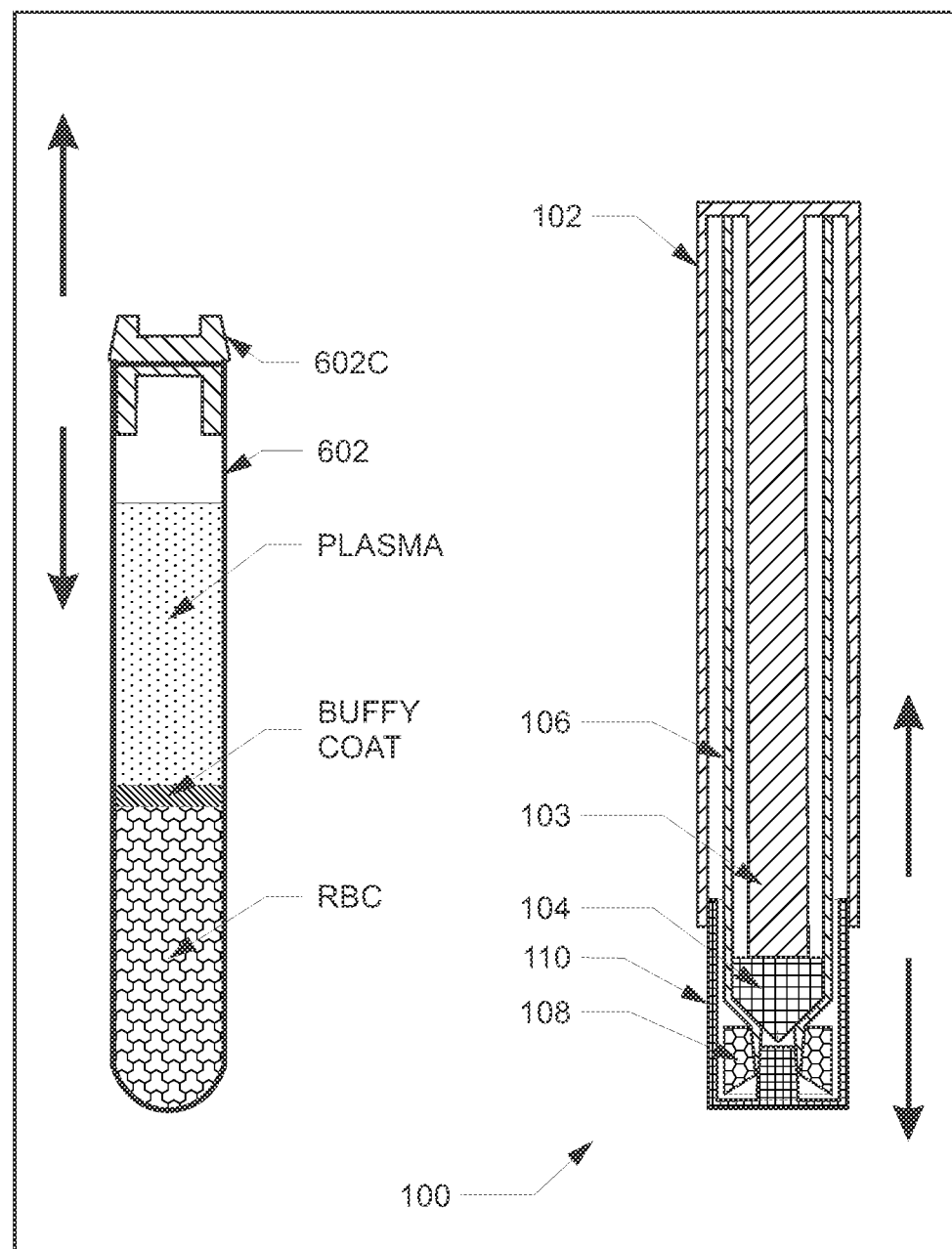

In FIG. 18A, a fluid collection tube 602 containing whole blood which has been centrifuged to separate the whole blood into its constituent parts; namely, red blood cells, buffy coat and plasma.

Figure 18B:
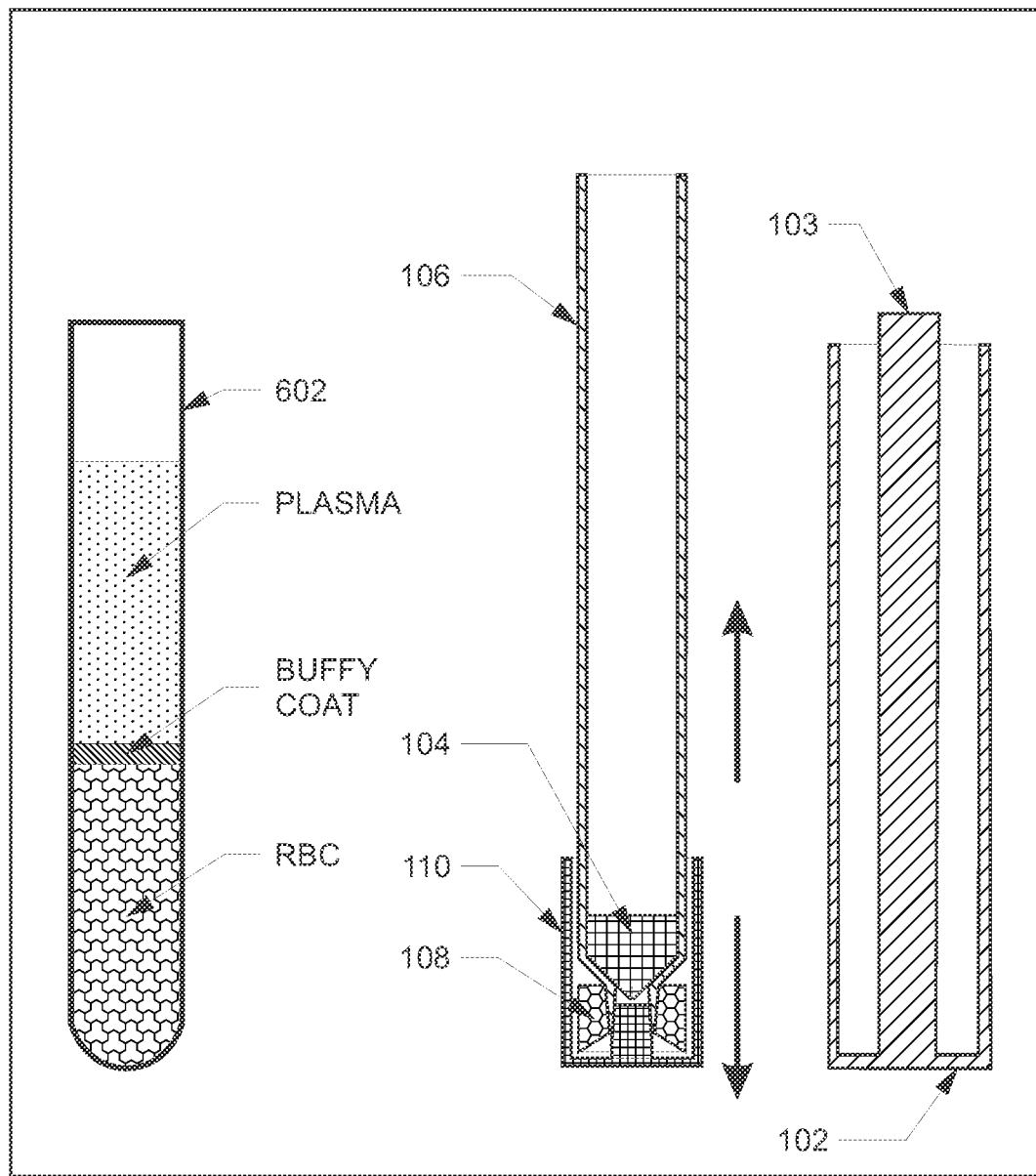

In FIG. 18B, the tube cap 602C is removed from the fluid collection tube 602, and the casing 102 with the rod 103 are removed from the fully-assembled device 100.

Figure 18C:
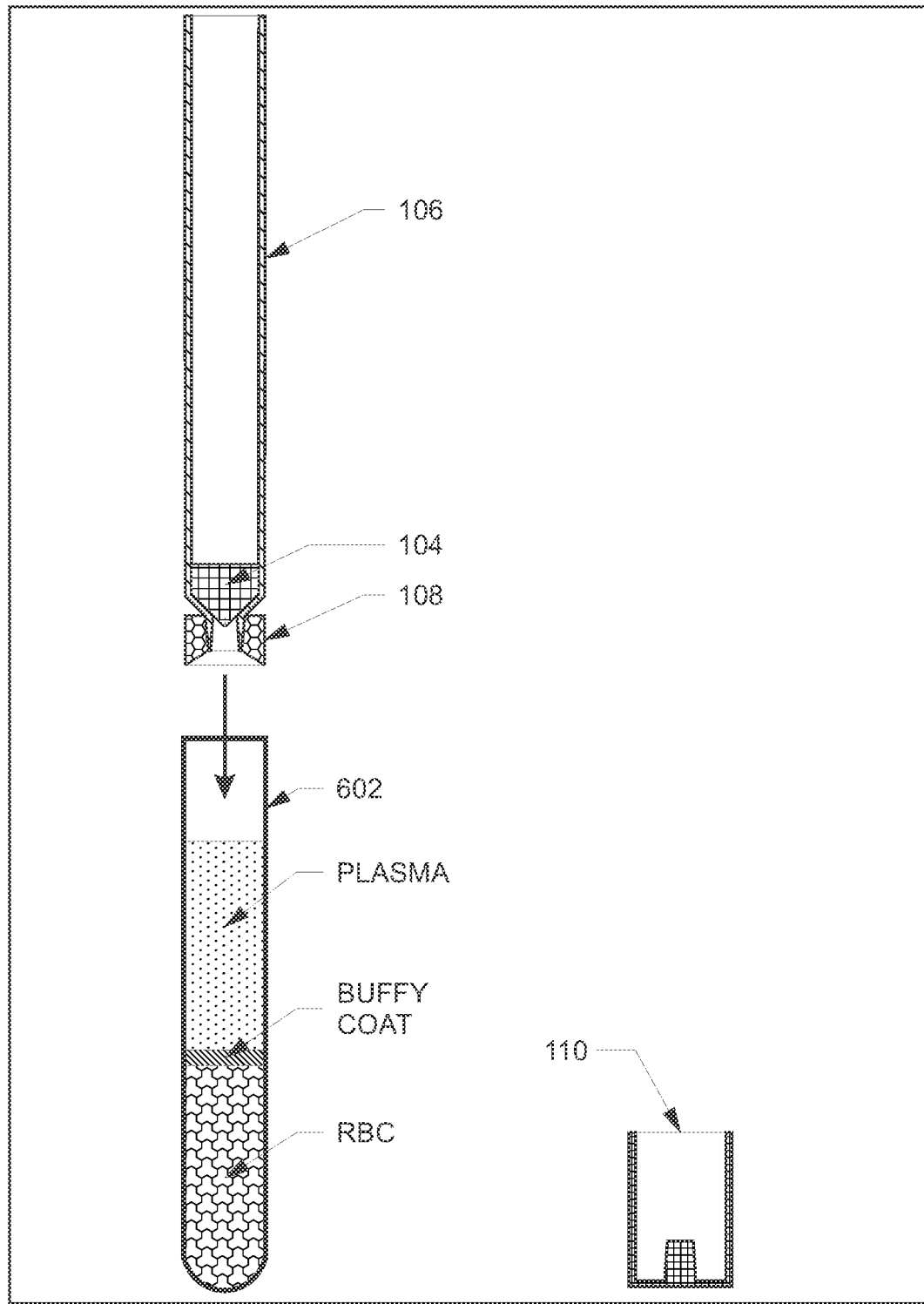

In FIG. 18C, the barrel cap 110 is removed, exposing the tube seal 108 and the distal end of the barrel 106. The distal end 106D of the barrel 106 with the tube seal 108 are inserted into the fluid collection tube 602.

Figure 18D:
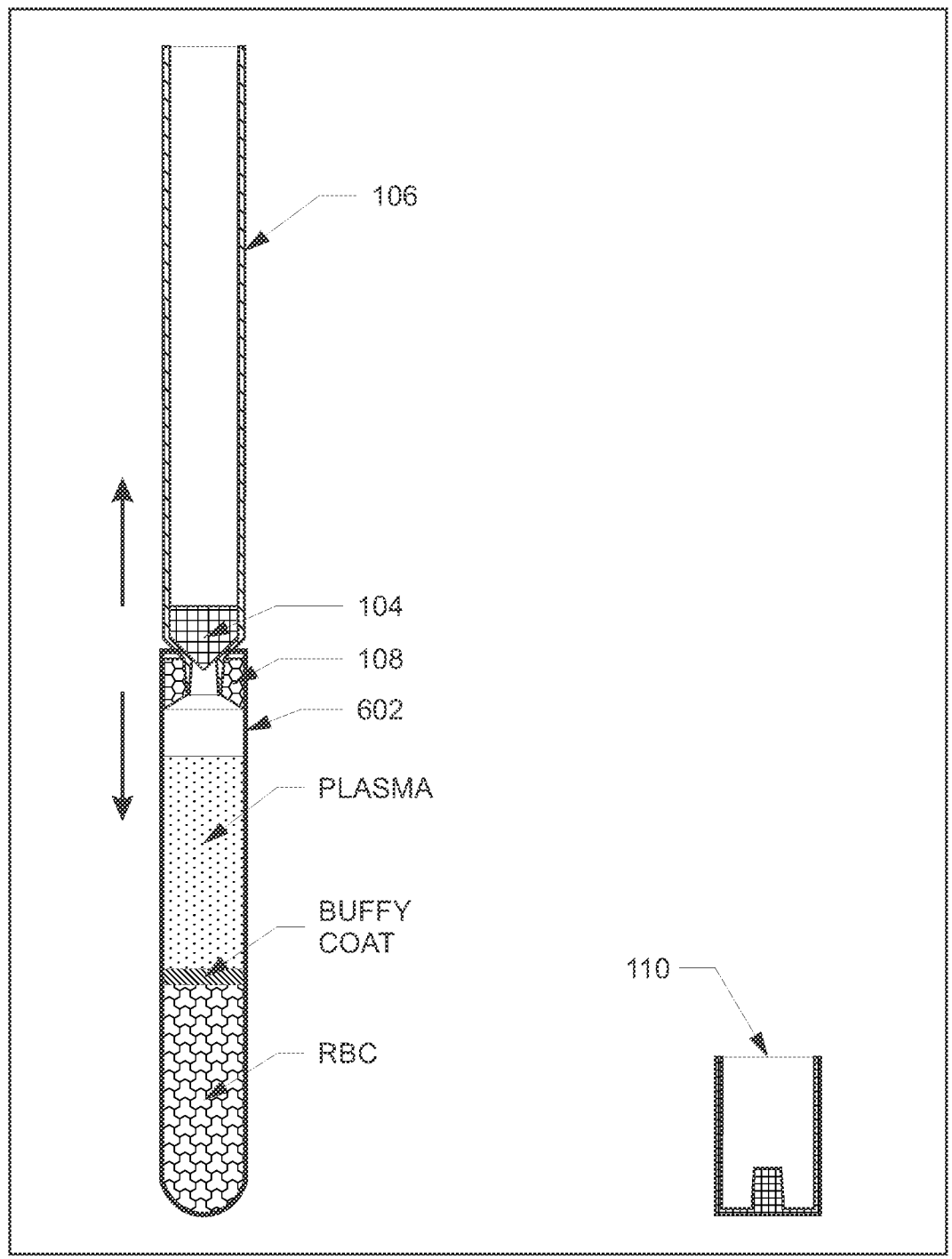

In FIG. 18D (optional), the distal end of the barrel 106 is gently removed with a twisting motion leaving the tube seal 108 engaged with the lumen of the fluid collection tube 602.

Figure 18E:
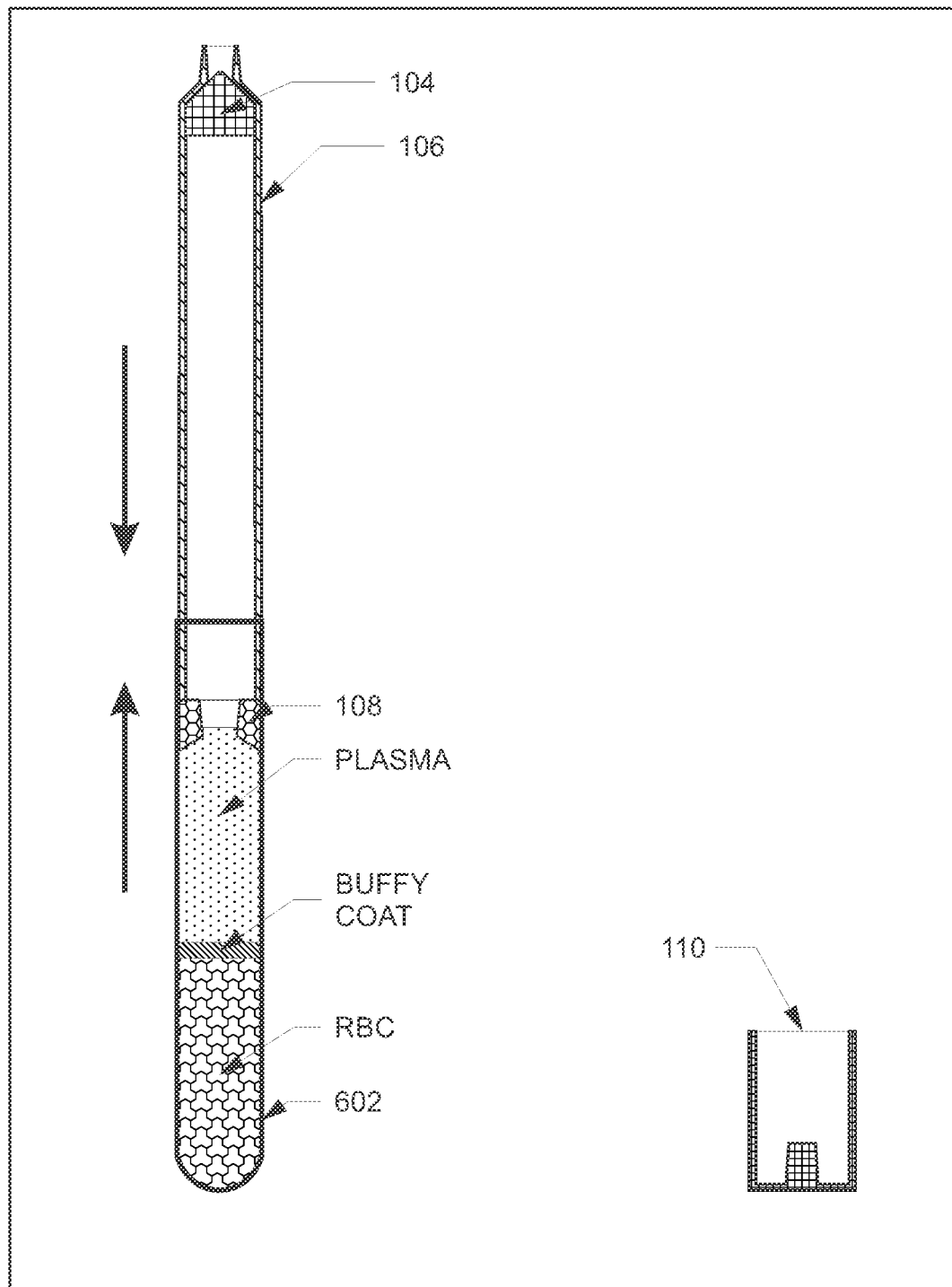

In FIG. 18E (optional), the proximal end of barrel 106 is placed in abutment with the tube seal 108 and is used to push or advance the tube seal 108 within the fluid collection tube until the tube seal just contacts the plasma.

Figure 18F:
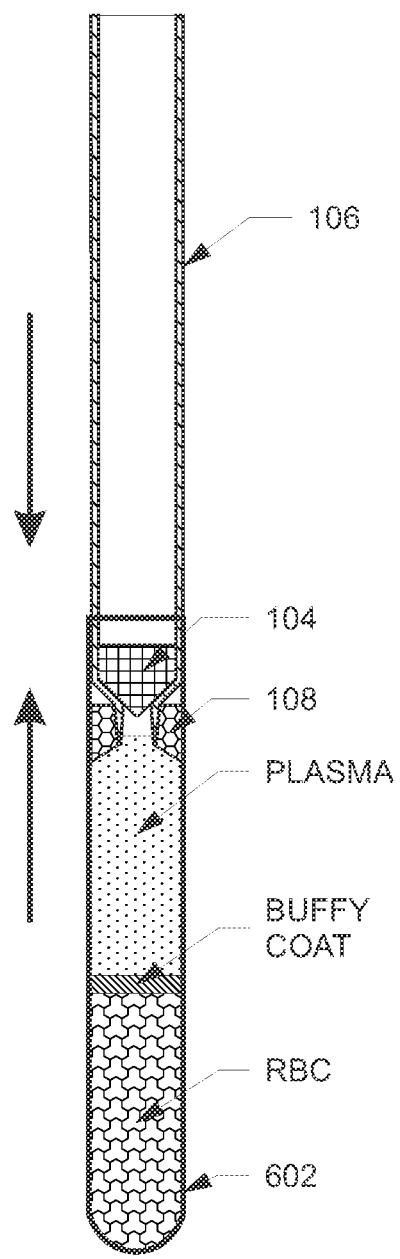

In FIG. 18F (optional), the proximal end 106P of the barrel 106 is withdrawn, the barrel 106 is flipped, and the distal end 106D is placed in sealing engagement with the tube seal 108.

Figure 18G:
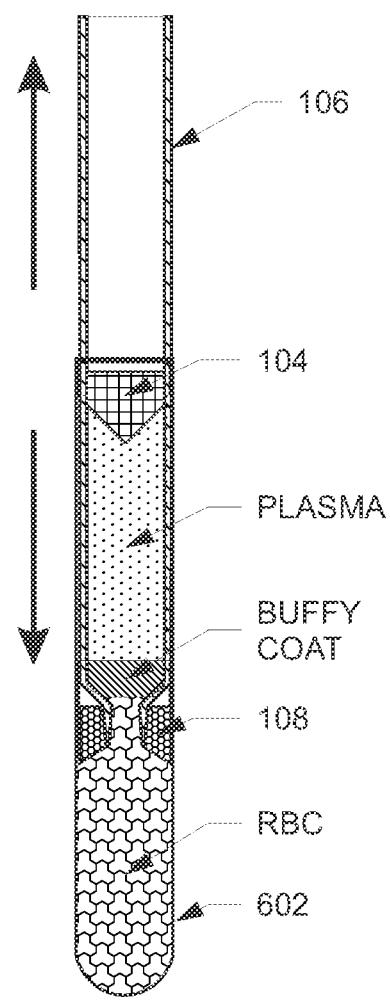

In FIG. 18G, as the barrel 106 and tube seal 108 are advanced distally into the fluid collection tube 602, plasma will flow proximally (in the opposite direction) through lumen 108L into the hollow interior 106H of the barrel 106. The barrel seal 104 is pushed proximally by the fluid flowing into the barrel 106. The barrel 106 should be advanced until red blood cells just start to enter into the barrel. At that point, plasma and the whole buffy coat have been transferred to the barrel 106. The conical shape of the distal end of the tube seal 108 will preferentially move the outer part of the buffy coat to the center of the tube seal 108 before red blood cells start to enter the tip 106T.

Figure 18H:
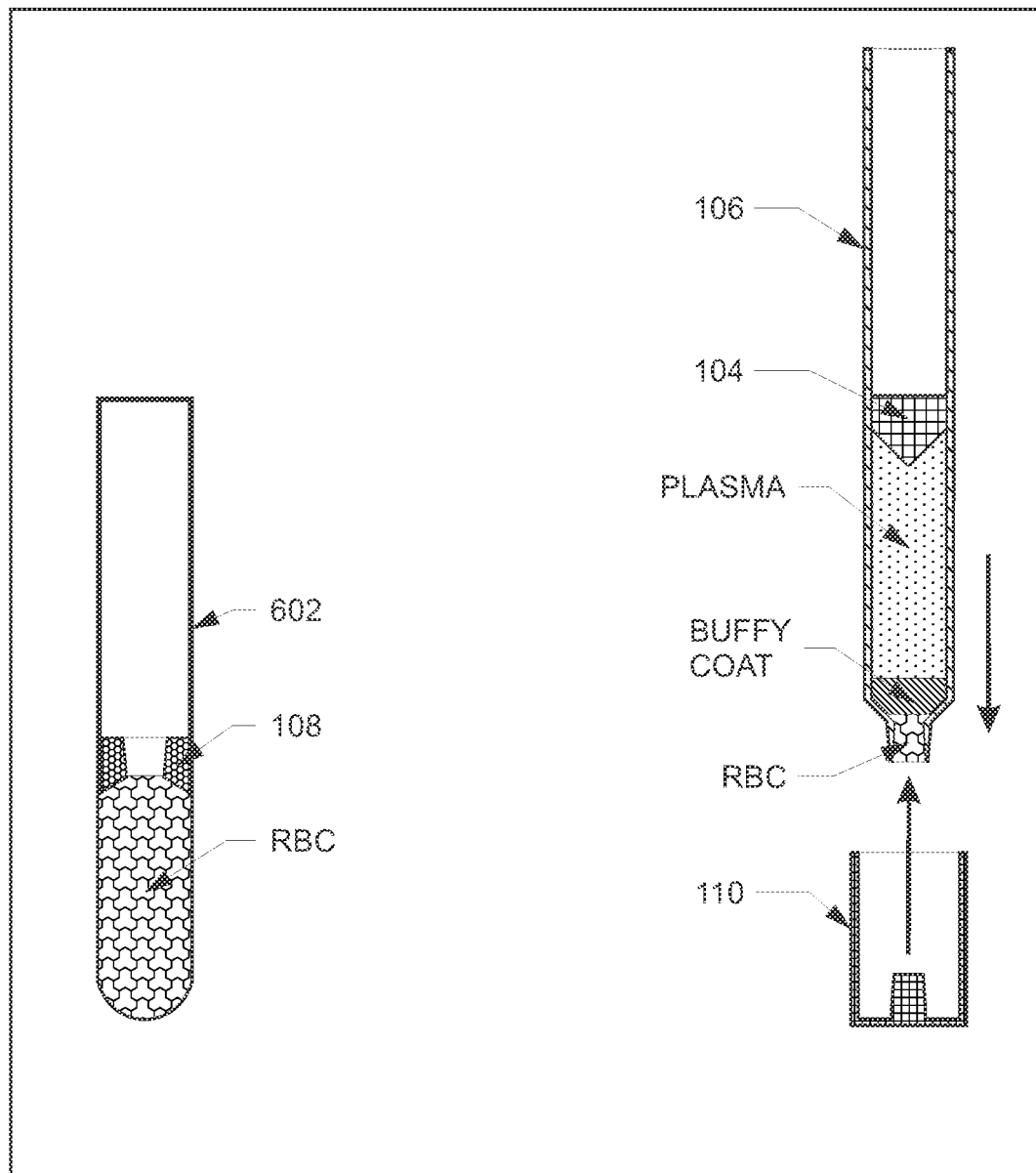

In FIG. 18H, the barrel 106 is withdrawn from the fluid collection tube 602 using a twisting and pulling motion to disengage the tube seal 108 from the barrel 106. In other words, as the barrel 106 is withdrawn, the tube seal 108 remains in the fluid collection tube 602 with the remaining red blood cells. The barrel cap 110 is engaged with the distal end 106D of the barrel 106.

Figures 1, 2, 18I:
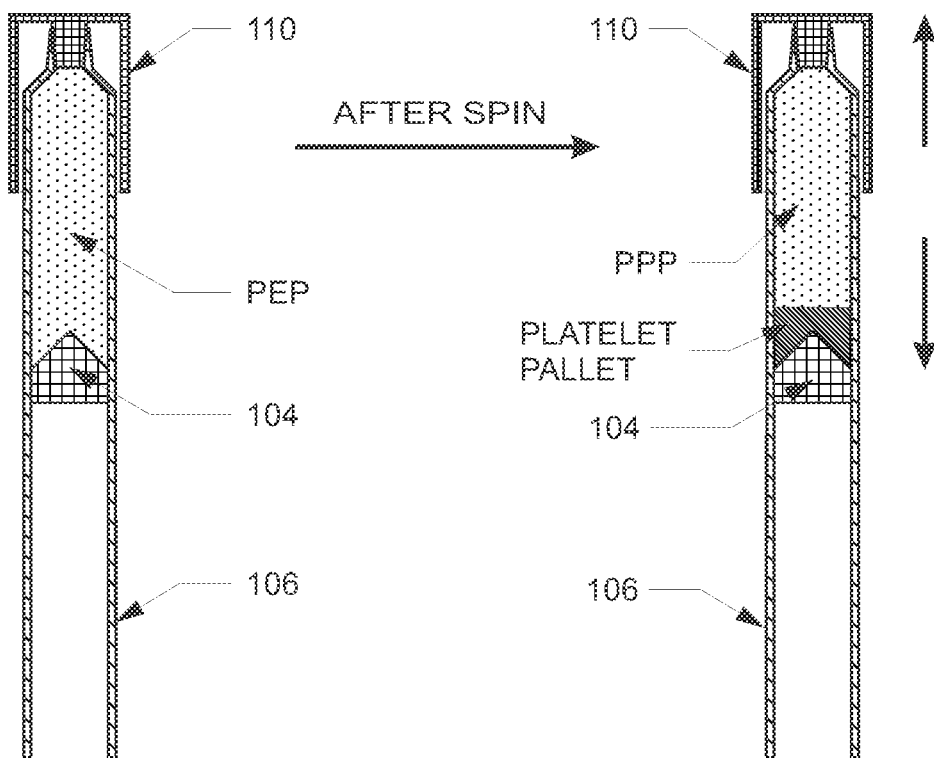

In FIGS. 18I-1 and 18I-2, the barrel 106 containing the plasma and buffy coat (collectively PEP) is capped with device barrel cap 110 and centrifuged (second spin cycle) to separate the PEP into its constituent parts; namely, platelet poor plasma (PPP) on the top and platelet pallet (compacted platelets) proximate the barrel seal 104. The centrifuged sample by volume comprises approximately 9/10 platelet poor plasma and 1/10 platelet pallet. One of ordinary skill in the art will appreciate that when inserting the tubular barrel into the centrifuge, the tip of the barrel should be pointing to the center axis of rotation.

Figures 1, 18J:
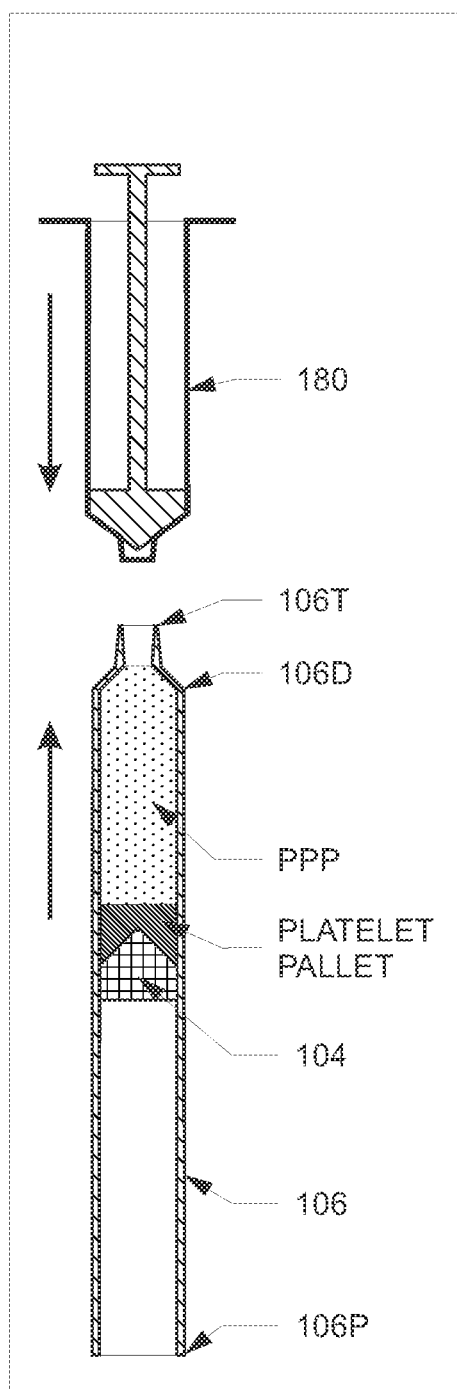
Figures 2, 18J:
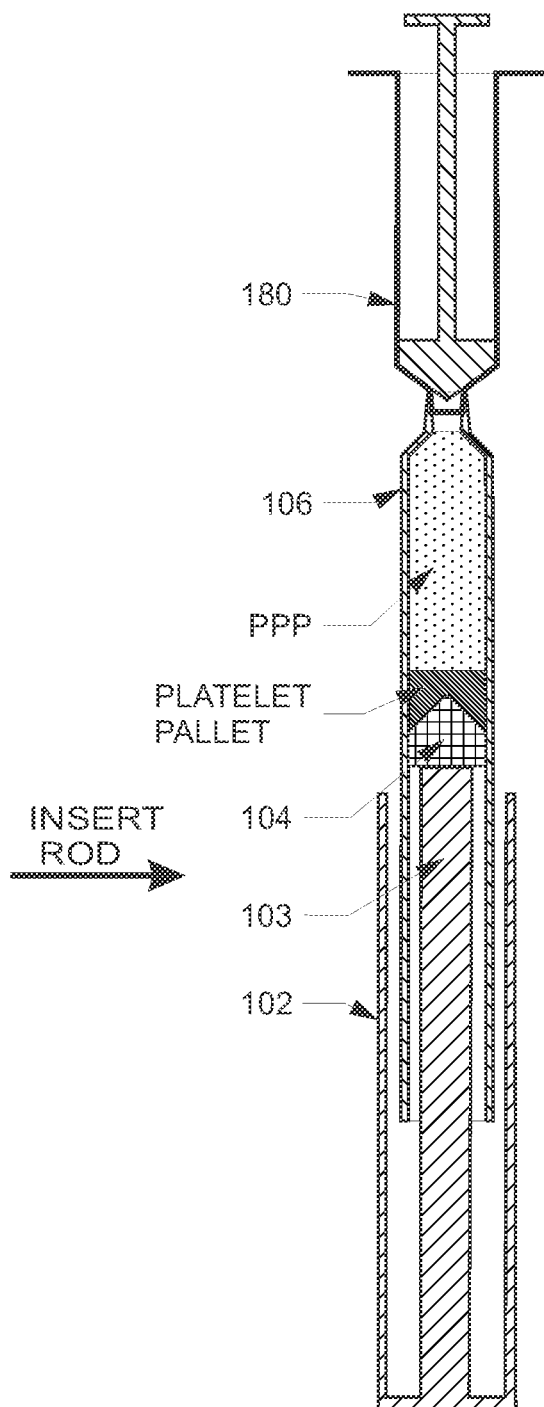
Figure 18M:
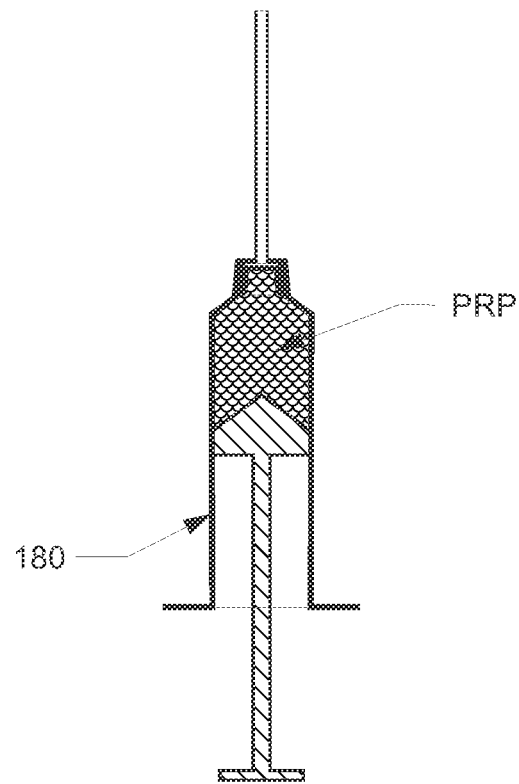

In FIGS. 18J-1 and 18J-2, a conventional syringe 180 is attached to the barrel 106. More particularly, the male aspect of the syringe 180 interfaces with the female aspect of the barrel tip 106T. In some examples, the rod 103 is inserted into the proximal end of the barrel 106.

In FIGS. 18K-1 and 18K-2, the distal end of the rod 103 is advanced distally within the barrel lumen 106L toward the tip 106T pushing the barrel seal 104 distally and expelling any residual air out of the barrel first (ideally), and then transferring 2/3-3/4 of the platelets poor plasma (PPP) to the attached syringe 180. One of ordinary skill in the art will appreciate that instead of (or in addition to) advancing the rod 103, the plunger of the attached conventional syringe 180 may be retracted to affect the transfer of air and PPP. The conventional syringe 180 with air and the platelet poor plasma is disconnected from the barrel tip 106T.

In FIGS. 18L-1 and 18L-2, an empty conventional syringe 180 is attached to the Luer tip 106T. The platelet pallet and remaining plasma are transferred back-and-forth between the barrel 106 and the syringe 180 by alternatingly pushing the rod 103 and the syringe plunger of the conventional syringe 180. This back-and-forth transfer dislodges the platelet pallet and mixes it with remaining plasma thereby creating platelet rich plasma (PRP). See, FIG. 18M. Now the whole PRP is transferred to the conventional syringe 180 and is ready for use.

Example PRP Extraction Using the Barrel with Ordinary Syringes (One-Spin)

FIGS. 20A-20M illustrate an example process for creating PRP. In this example, the barrel 106 is the key feature, because it integrates the functions of both the fluid collection tube and the tube seal.

Figure 20A:
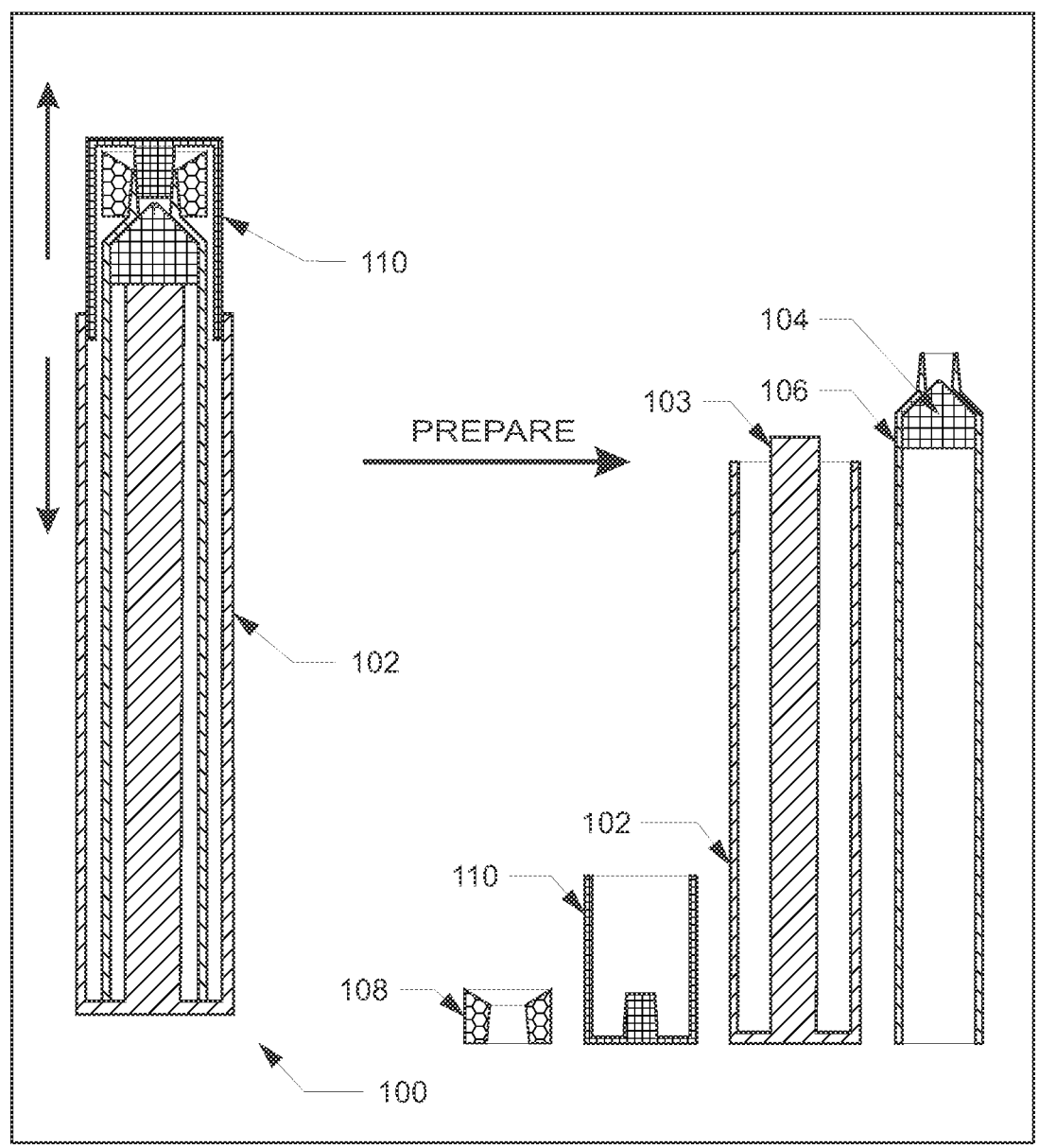

In FIG. 20A the fully assembled device 100 is disassembled by removing the barrel cap 110, the tube seal 108, case 102 and rod 103 from the barrel 106, leaving the barrel seal 104 within the lumen of the tube 106.

In FIGS. 20B-1, 20B-2 and 20B-3 a conventional syringe 180 containing whole blood is attached to the barrel 106, and the blood is transferred from the syringe 180 into the barrel 106 by advancing the plunger within the syringe. The barrel seal 104 is pushed toward the proximal end 106P of the barrel 106 by the blood entering the tube 106.

In FIGS. 20C-1, 20C-2, and 20C-3 the now empty conventional syringe 108 is disengaged from the barrel 106 (and discarded), and the barrel cap 110 is placed in sealing engagement with the tip 106T of the barrel 106.

In FIGS. 20D-1 and 20D-2, the barrel 106 with the blood and the barrel cap 110 is centrifuged, separating the blood into a layer of red blood cells (RBC), buffy coat, and plasma.

In FIGS. 20E-1 and 20E-2, the barrel cap 110 is removed from the barrel 106, and a fresh (empty) conventional syringe 180 having a plunger movably mounted within is placed in engagement with the tip 106T of the barrel 106.

In FIGS. 20E-1 and 20E-2 the plasma and buffy coat (collectively "PEP") are transferred from the barrel 106 into the syringe 180. This may be accomplished either by (a) retracting the plunger within the syringe 180; or (b) by advancing the rod 103 and the barrel seal 104 within the barrel 106. Or both, as is the case with the tube. The red blood cells are not transferred from the barrel 106 into the syringe 180.

In FIGS. 20G-1 and 20G-2, the syringe 180 with the PEP are connected to a fresh barrel 106.

In FIGS. 20H-1 and 20H-2, the PEP is transferred from the syringe 180 into the barrel 106, and barrel cap 110 is placed in sealing engagement with the barrel tip 106T.

Figures 1, 2, 20I:
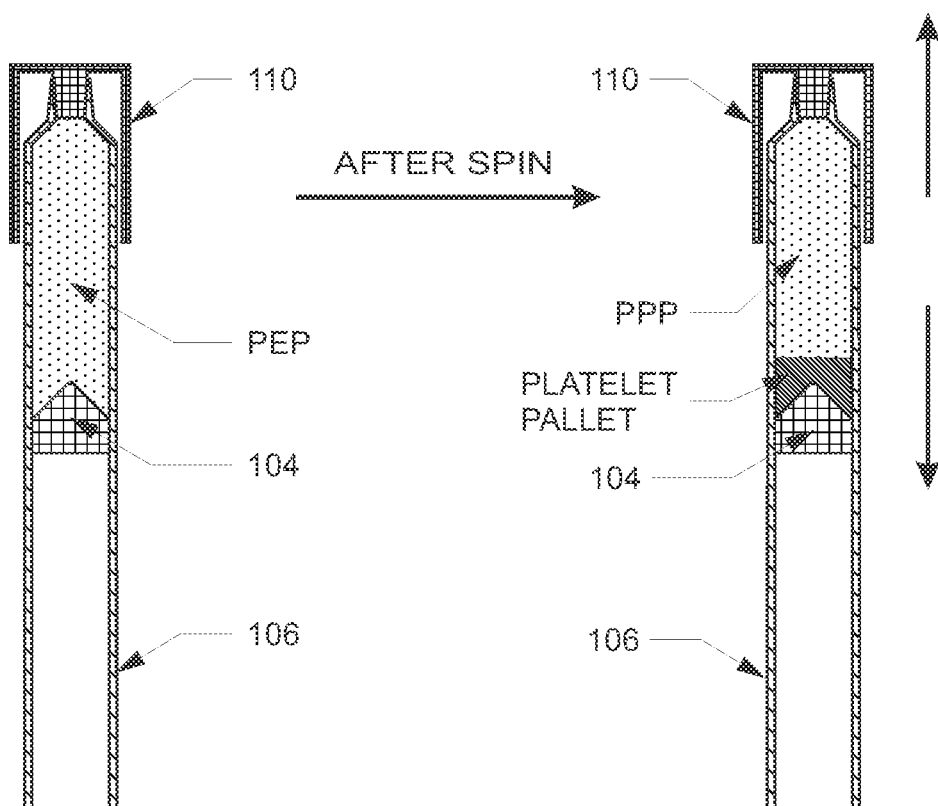
Figure 20M:
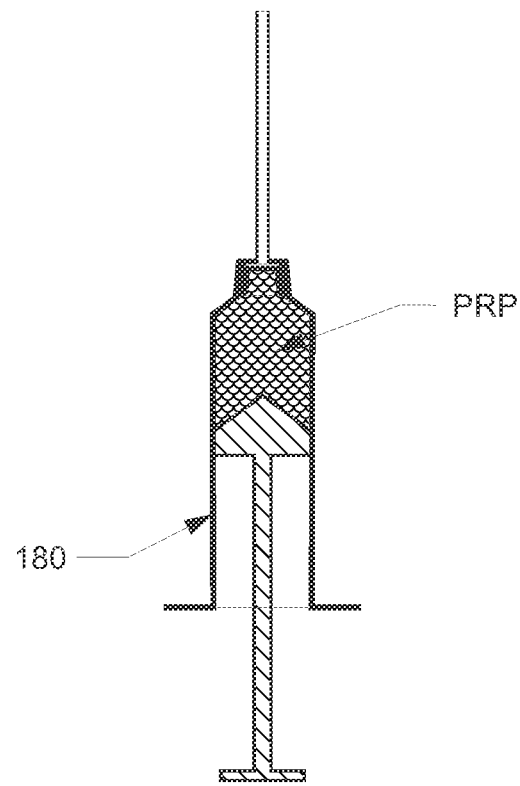

In FIGS. 20I-1 and 20I-2, the capped barrel 106 containing the PEP is centrifuged (second spin cycle) to separate the PEP into its constituent parts; namely, platelet poor plasma (PPP) on the top and platelet pallet (compacted platelets) proximate the barrel seal 104. The centrifuged sample by volume comprises approximately 9/10 platelet poor plasma and 1/10 platelet pallet.

In FIGS. 20J-1 and 20J-2, a conventional syringe 180 is attached to the barrel 106. More particularly, the male aspect of the syringe interfaces with the female aspect of the barrel tip 106T. The rod 103 is inserted into the proximal end of the barrel 106.

In FIGS. 20K-1 and 20K-2, the distal end of the rod 103 is advanced distally within the barrel lumen 106L toward the tip 106T pushing the barrel seal 104 distally and expelling any residual air and 2/3-3/4 of the platelets poor plasma (PPP) to the attached syringe 180. One of ordinary skill in the art will appreciate that instead of (or in addition to) advancing the rod 103, the plunger of the attached conventional syringe 180 may be retracted to affect the transfer of air and PPP. The conventional syringe 180 with air and the platelet poor plasma is disconnected from the barrel tip 106T. One of ordinary skill in the art will appreciate that the residual air could be expelled from the barrel prior to connecting the syringe 180.

In FIGS. 20L-1 and 20L-2, an empty conventional syringe 180 is attached to the Luer tip 106T. The platelet pallet and remaining plasma is transferred back-and-forth between the barrel 106 and the syringe 180 by alternatingly pushing the rod 103 and the syringe plunger of the conventional syringe 180. This back-and-forth transfer is also applicable to the methods with the tube, that also use the barrel. This back-and-forth transfer dislodges platelet pallet and mixes it with remaining plasma thereby creating plasma rich platelets (PRP). See, FIG. 20M. Now the whole PRP is transferred to the conventional syringe 180 and is ready for use.

Example PRP Extraction Using the Tube Seal with the Barrel (Single-Spin)

FIGS. 19A-19I-2 illustrate another example process for creating PRP.

Figure 19A:
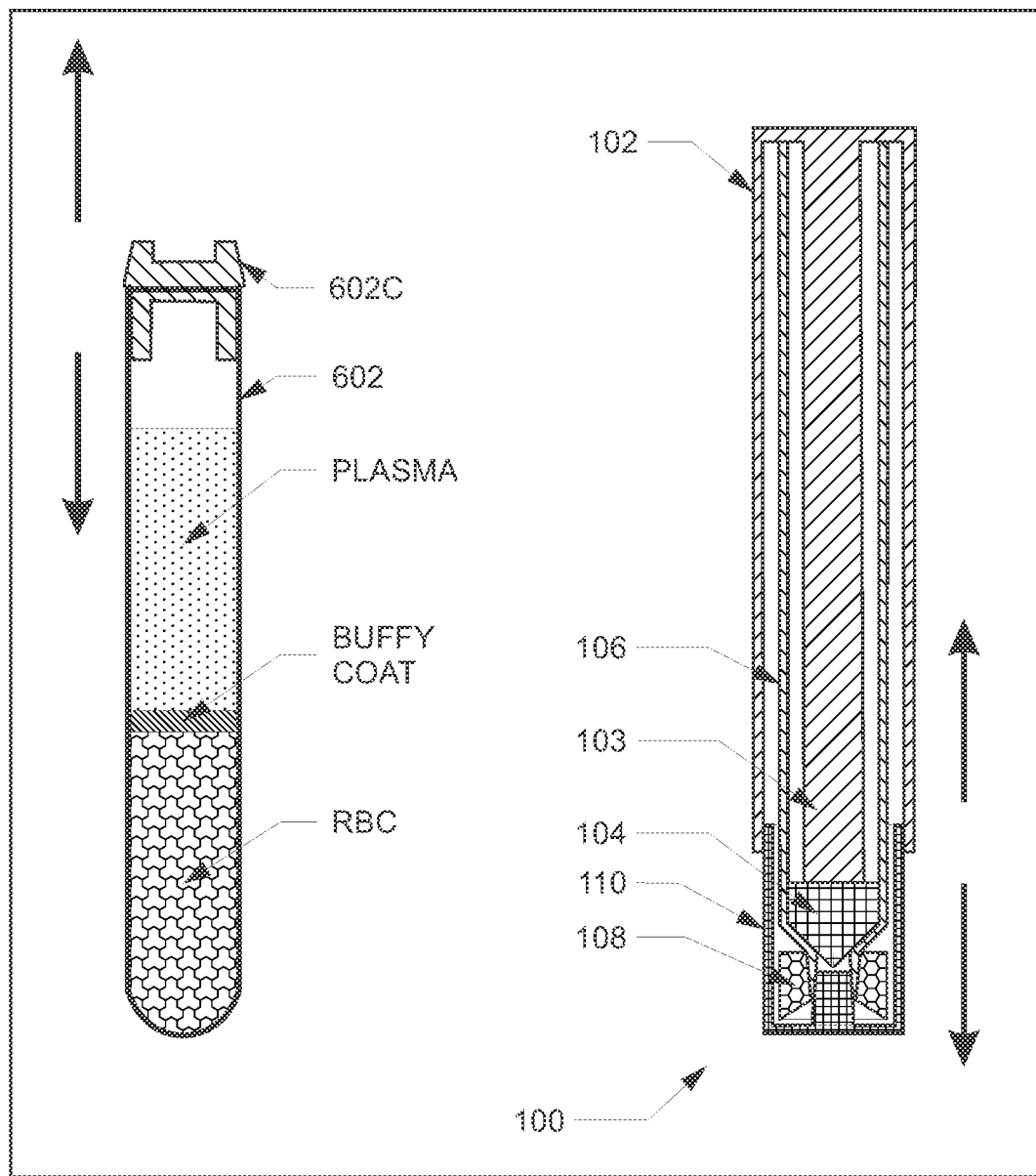

In FIG. 19A, a fluid collection tube containing a sample of whole blood is centrifuged to separate the blood into constituent layers of red blood cells (RBC), buffy coat, and plasma.

Figure 19B:
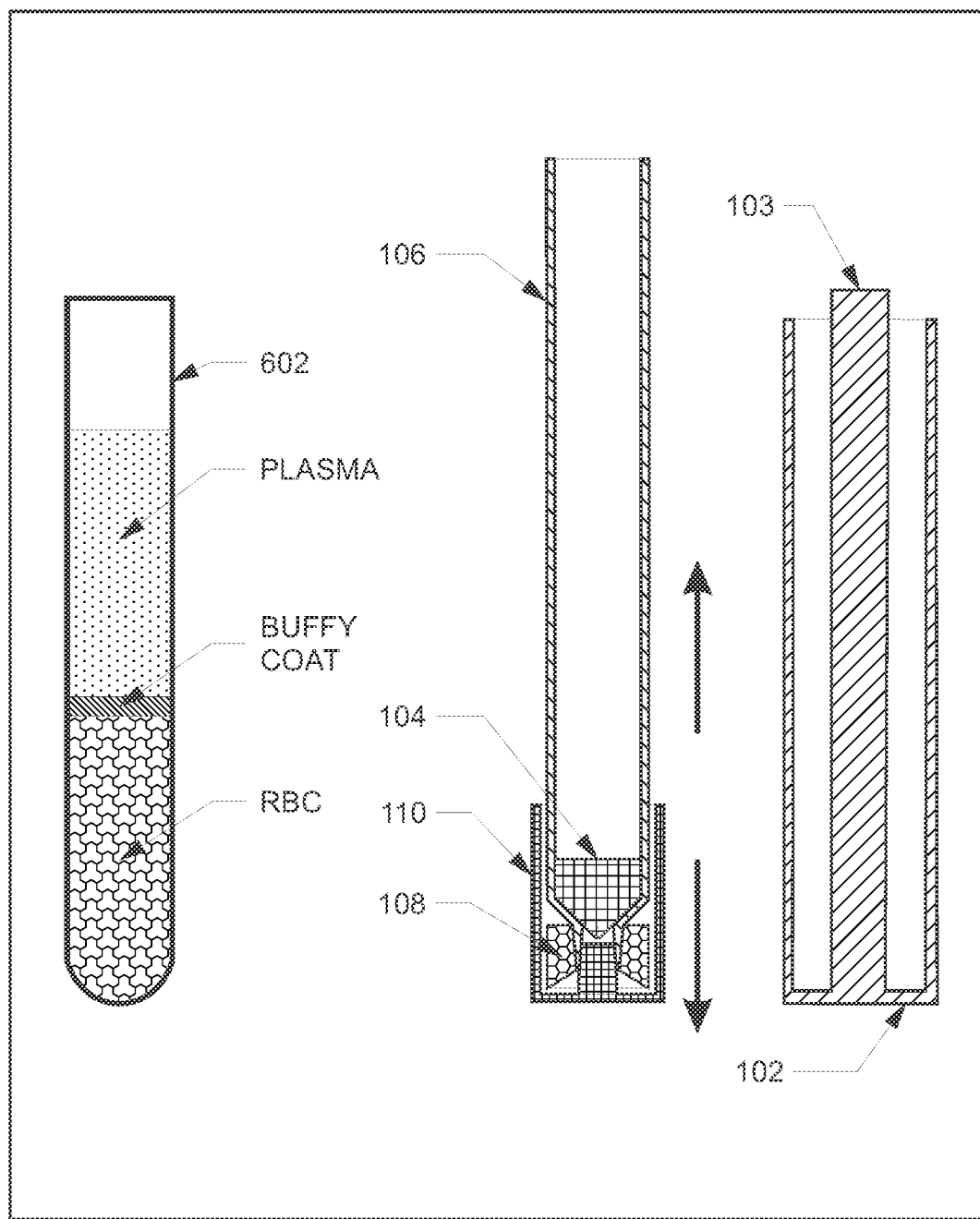

In FIG. 19B, the casing 102 and rod 103 are removed from the barrel 106, and the cap 602C is removed from the fluid collection tube 602.

Figure 19C:
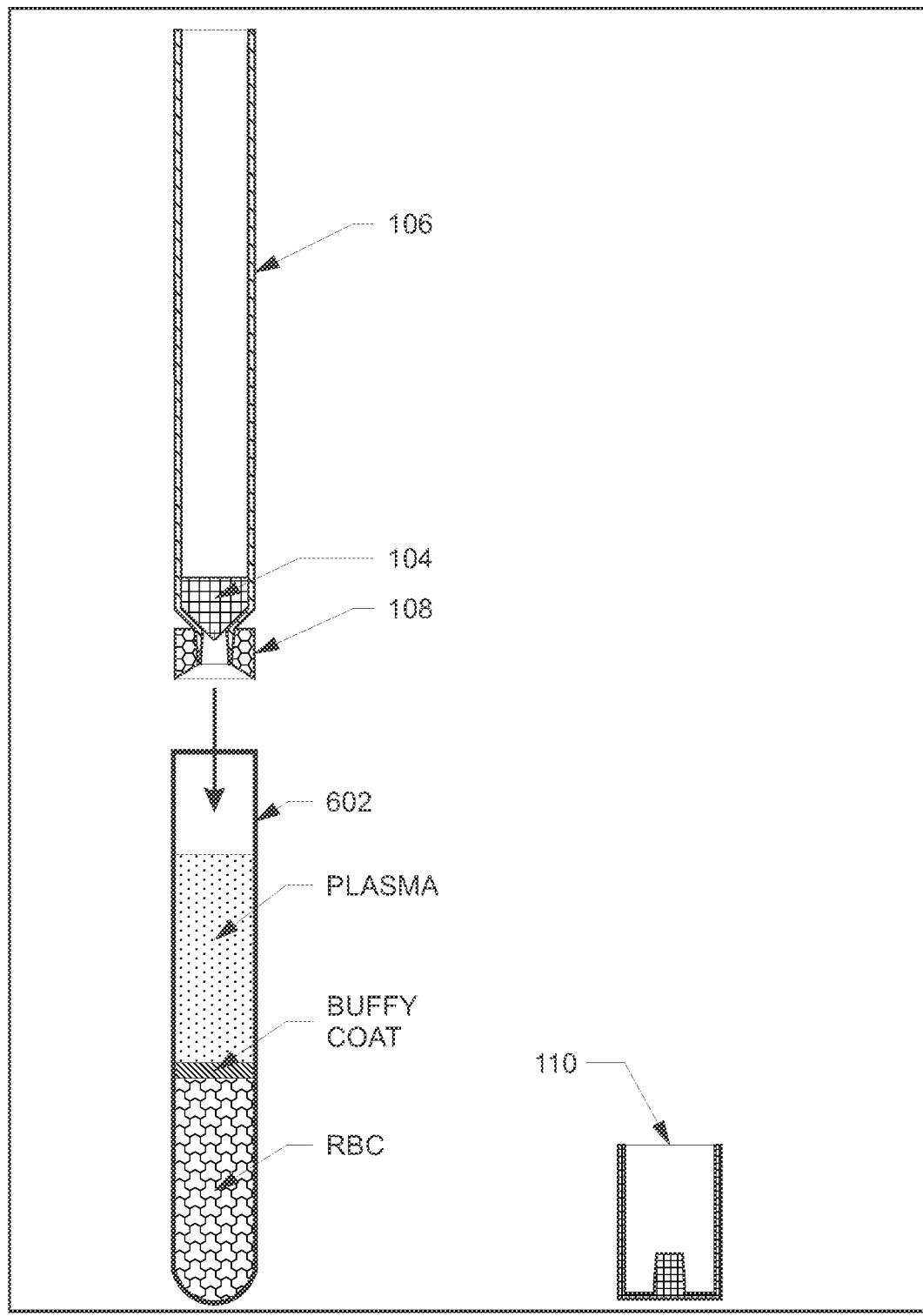

In FIG. 19C, the barrel cap 110 is removed from the barrel 106, and the distal end of the barrel 106 with the barrel seal 104 inside the lumen of the barrel and the tube seal 108 mounted on the tip 106T are inserted into the open mouth of a fluid collection tube 602.

Figure 19D:
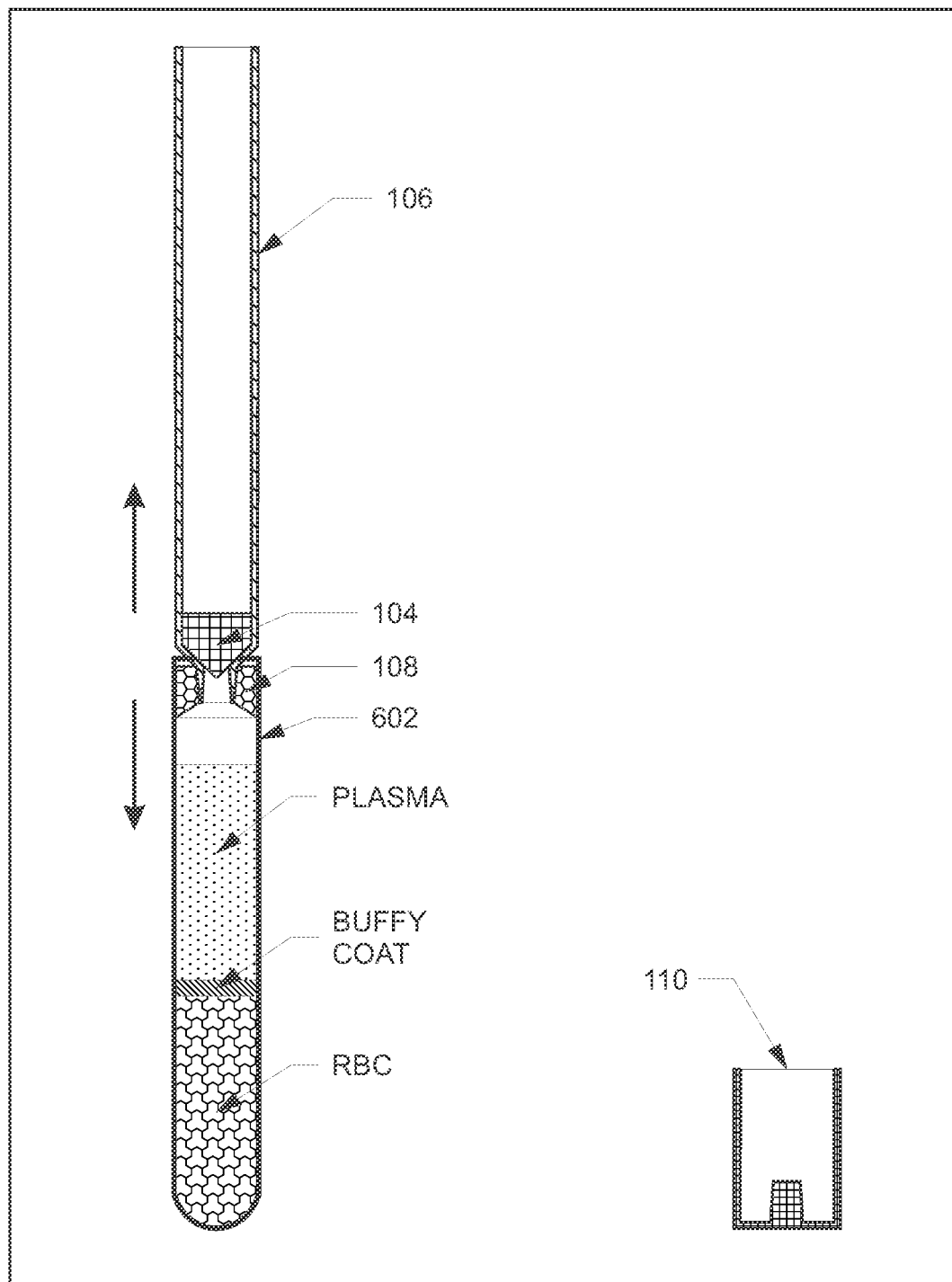

In FIG. 19D (optional), the barrel is removed from the fluid collection tube with a gentle twisting motion to separate the tube seal 108 from the tip 106T of the barrel 106, leaving the tube seal 108 engaged with the inner surface of the fluid collection tube 602.

Figure 19E:
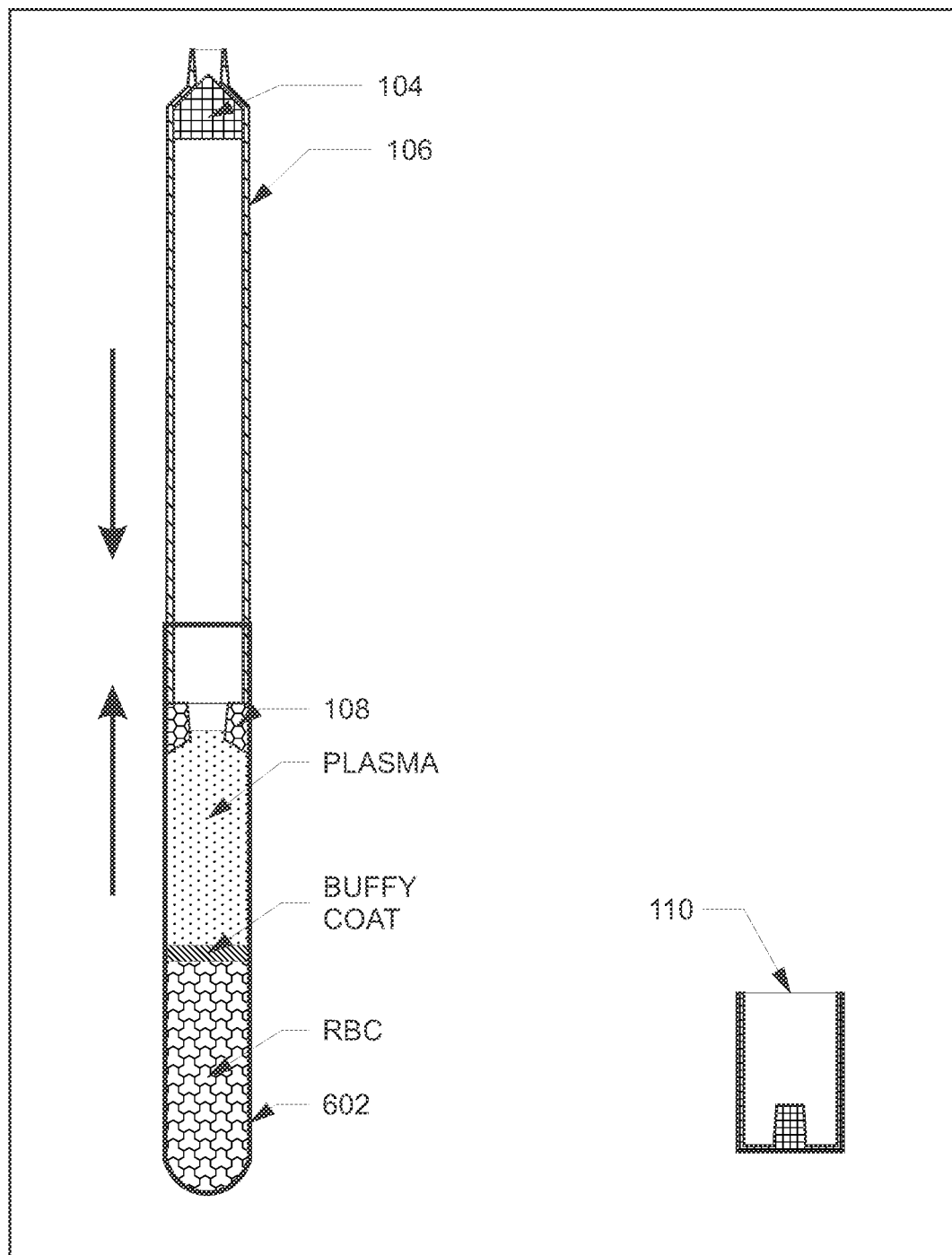

In FIG. 19E (optional), the barrel 106 is flipped and the proximal end 106P is inserted into the fluid collection tube 602 and placed in abutment with the tube seal 108. The barrel 106 is used to push the tube seal distally in the fluid collection tube until it comes in contact with the plasma. The proximal end of the barrel 106 is withdrawn, and the distal end of the barrel 106 is re-inserted into the sealing engagement with the fluid collection tube 602.

In FIGS. 19F-1 and 19F-2 the barrel 106 is used to advance the tube seal 108 within the fluid collection tube 602. As the barrel 106 is advanced distally into the fluid collection tube 602, plasma enters into the barrel and pushes the barrel seal 104 proximally. The barrel 106 is advanced until between 2/3 and 3/4 of the plasma has been transferred into the barrel 106, leaving the red blood cells, buffy coat, and 1/4 of the plasma. The barrel with the plasma is disengaged from the fluid collection tube 602 and discarded.

In FIGS. 19G-1 and 19G-2, an empty barrel 106 is attached to the fluid collection tube 602 containing red blood cells, buffy coat, and remaining plasma. The barrel 106 is advanced into the fluid collection tube 602 until all of the plasma and the buffy coat are transferred into the barrel 106, leaving the red blood cells.

In FIGS. 19H-1 and 19H-2 a fresh conventional syringe 180 is placed in sealing engagement with the tip 106T of the barrel 106 containing the plasma and the buffy coat (collectively PRP).

Figures 1, 2, 19I:
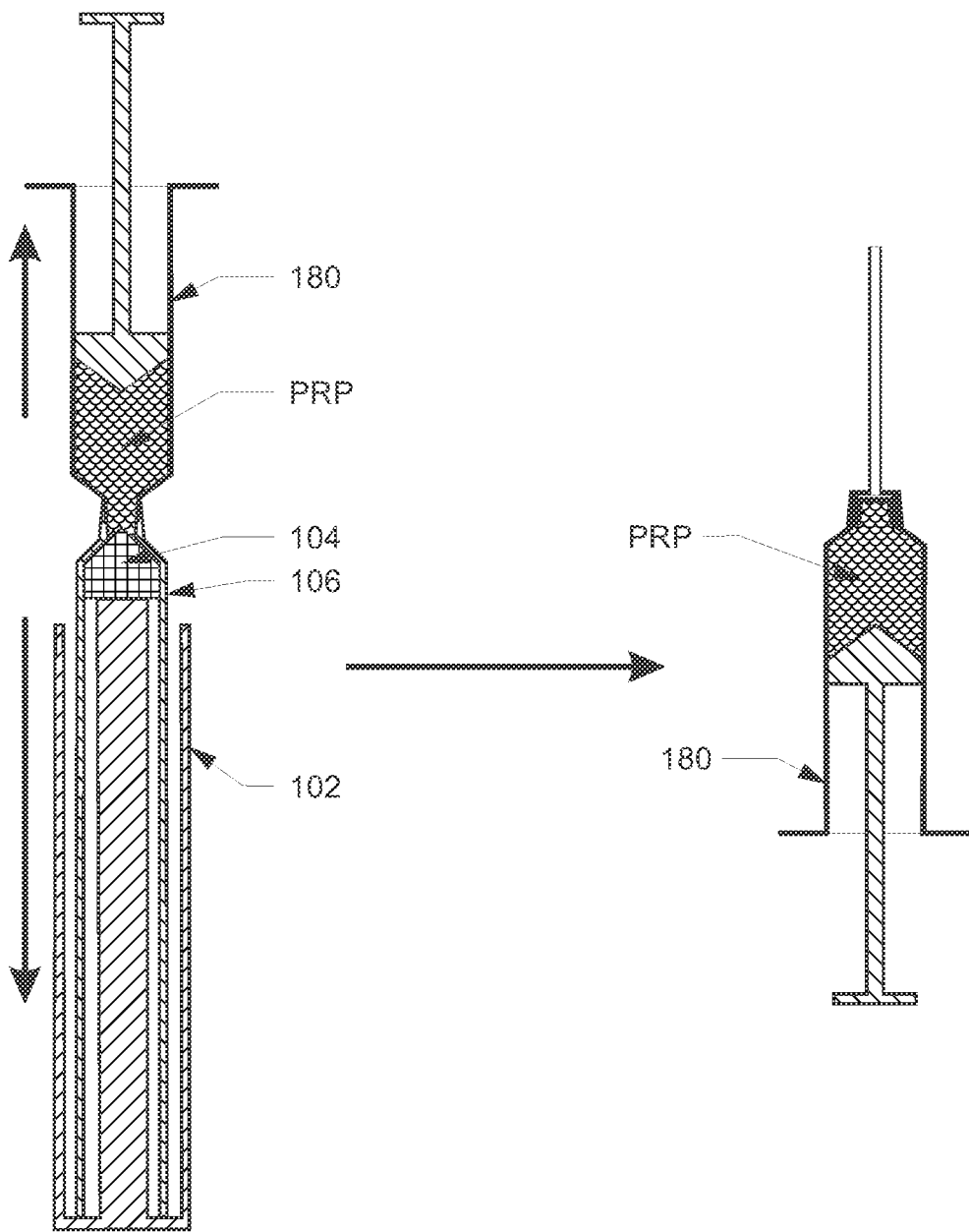

In FIGS. 19I-1 and 19I-2, the plasma and buffy coat (PRP) are transferred from the barrel into the syringe by either (a) retracting the plunger within the syringe 180; or (b) by advancing the rod 103 and the barrel seal 104 within the barrel 106. The barrel 106 is disconnected from the syringe and discarded, and a needle is attached to the syringe.

While the exemplary embodiments have been described in some detail, by way of example and for clarity of understanding, those of skill in the art will recognize that a variety of modification, adaptations, and changes may be employed. The scope of the present invention may be limited solely by the appending claims.

The invention claimed is:

1. A device for extracting plasma from a fluid collection tube containing a sample of whole blood which has been centrifuged to form a red blood cell layer, a buffy coat layer and a plasma layer, the device comprising:
   a tubular barrel having sidewall surrounding a lumen which extends between proximal and distal ends thereof, the tubular barrel forming a tip at a distal end;
   a barrel seal movingly seated within the lumen of the tubular barrel, the barrel seal closing and sealing the proximal end of the tubular barrel;
   a tube seal having a proximal end, a distal end, and a lumen extending therebetween, the proximal end having a frustoconical or chamfered face, the tube seal having an outer diameter sized to sealingly engage with an inner surface of the fluid collection tube, and a diameter of the lumen sized to sealingly engage with an outer surface of the tip of the tubular barrel, the tube seal mounted on the tubular barrel such that the tip of the tubular barrel extends into the tube seal lumen;
   wherein as the tubular barrel is advanced into the fluid collection tube, the tube seal sealingly engages with inner walls of the fluid collection tube and the outer surface of the tip of the tubular barrel, and the barrel seal is pushed proximally by plasma flowing from the fluid collection tube into the lumen of the tubular barrel.

2. The tube seal of claim 1, wherein the tube seal is an elastomeric member having at least one raised sealing ring provided on the exterior surface thereof.

3. The device of claim 1, further comprising an elongate rod having an outer diameter which is smaller than a diameter of the lumen of the tubular barrel, the rod being removably inserted into the lumen of the tubular barrel.

4. The device of claim 1, further comprising a barrel cap configured to sealingly engage with the tip of the tubular barrel and engaging an exterior surface of the tip and/or having a plug which fits into the lumen of the tip.

5. A device for extracting plasma from a fluid collection tube containing a sample of whole blood which has been centrifuged to form a red blood cell layer, a buffy coat layer and a plasma layer, the device comprising:
- a tubular barrel having sidewall surrounding a lumen which extends between proximal and distal ends thereof, the tubular barrel forming a tip at a distal end;
- a barrel seal movingly seated within the lumen of the tubular barrel, the barrel seal closing and sealing the proximal end of the tubular barrel;
- a tube seal having a proximal end, a distal end, and a lumen extending therebetween, the proximal end having a frustoconical or chamfered face, the tube seal having an outer diameter sized to sealingly engage with an inner surface of the fluid collection tube, and an inner diameter sized to sealingly engage with an outer surface of the tip of the tubular barrel, the tube seal mounted on the tubular barrel such that the tip of the tubular barrel extends into the tube seal lumen;
- wherein as the tubular barrel is advanced into the fluid collection tube, the tube seal engages with inner walls of the fluid collection tube and the outer surface of the tip of the tubular barrel, and the barrel seal is pushed proximally by plasma flowing from the fluid collection tube into the lumen of the tubular barrel;
- an elongate rod having an outer diameter which is smaller than a diameter of the lumen of the tubular barrel, the rod being removably inserted into the lumen of the tubular barrel;
- a tubular casing having a closed proximal end and an open distal end and a lumen extending between the closed proximal end and the open distal end;
- a diameter of the rod being less than a diameter of the lumen of the tubular casing;
- at least a portion of the rod coaxially received within the tubular casing, with a gap G defined between an inner surface of the tubular casing and an exterior surface of the rod; and
- a portion of the tubular barrel sidewall being coaxially received in the gap G.

6. A kit for extracting plasma from a fluid collection tube containing a centrifuged sample of whole blood which has been centrifuged to form a red blood cell layer, a buffy coat layer and a plasma layer, the kit comprising:
- a tube seal having a lumen therethrough and a concave face, the tube seal sized to movably engage with an inner surface of the fluid collection tube, the lumen of tube seal being sized to sealingly engage with a tip of a tubular barrel;
- a tubular barrel having sidewall surrounding a lumen which extends between proximal and distal ends thereof, the tubular barrel forming a tip at a distal end; and
- a barrel seal movingly seated within the lumen of the tubular barrel, the barrel seal closing and sealing the proximal end of the tubular barrel;
- wherein the tip of the tubular barrel sized to snugly fit into and sealingly engage with the lumen of the tube seal;
- wherein as the tubular barrel is advanced into the fluid collection tube, the tube seal engages with the inner surface of the fluid collection tube and engages with an outer surface of the tip of the tubular barrel, and the barrel seal is pushed proximally by plasma flowing from the fluid collection tube into the lumen of the tubular barrel.

7. The kit of claim 6, comprising an elongate rod having an outer diameter which is smaller than a diameter of the lumen of the tubular barrel, the elongate rod being removably inserted into the lumen of the tubular barrel.

8. The kit of claim 7, further comprising a tubular casing having a closed proximal end and an open distal end and a lumen extending between the closed proximal end and the open distal end.

9. The kit of claim 6, wherein the tube seal is removably mounted to the tip of the tubular barrel.

10. The kit of claim 9, further comprising a barrel cap configured to sealingly engage with the tip of the tubular barrel and engaging an exterior surface of the tip and/or having a plug which fits into the lumen of the tip.

* * * * *